US008239217B2

(12) United States Patent
Helmus et al.

(10) Patent No.: US 8,239,217 B2
(45) Date of Patent: Aug. 7, 2012

(54) PRESCRIPTION MANAGEMENT SYSTEM

(75) Inventors: Scott M. Helmus, Succasunna, NJ (US);
Donna L. Rosen, Kinnelon, NJ (US);
Leo H. Bressman, Livingston, NJ (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 0 days.

(21) Appl. No.: 12/372,310

(22) Filed: Feb. 17, 2009

(65) Prior Publication Data
US 2009/0164244 A1 Jun. 25, 2009

Related U.S. Application Data

(62) Division of application No. 10/134,638, filed on Apr. 30, 2002, now Pat. No. 7,493,263.

(51) Int. Cl.
*G06Q 50/00* (2012.01)
(52) U.S. Cl. .................. 705/3; 705/2; 600/300
(58) Field of Classification Search .......... 705/2, 3, 705/8; 715/700; 645/418
See application file for complete search history.

(56) References Cited

U.S. PATENT DOCUMENTS

| | | | |
|---|---|---|---|
| 5,208,762 A | 5/1993 | Charhut et al. | |
| 5,597,995 A * | 1/1997 | Williams et al. | 235/375 |
| 5,602,936 A | 2/1997 | Green et al. | |
| 5,671,282 A | 9/1997 | Wolff et al. | |
| 5,737,539 A | 4/1998 | Edelson et al. | |
| 5,771,657 A | 6/1998 | Lasher et al. | |
| 5,883,370 A | 3/1999 | Walker et al. | |
| 5,963,453 A | 10/1999 | East | |
| 6,202,923 B1 | 3/2001 | Boyer et al. | |
| 6,330,491 B1 | 12/2001 | Lion | |
| 2003/0149599 A1* | 8/2003 | Goodall et al. | 705/2 |

OTHER PUBLICATIONS

Dec. 10, 2002. International Search Report from PCT/US02/13508.
Drug Company Banks on Automated Pharmacy, Schwad David, Newshouse News Services; Washington; Nov. 13, 2001.
May 11, 2004. International Preliminary Examination Report from PCT/US02/13508.
Muirhead, Greg, "Rx Scan," Drug Topics. Nov. 7, 1994. vol. 138, No. 21, p. 70.
Schwab David, "Drug Company Banks on Automated Pharmacy," Newhouse News Service. Nov. 13, 2001. 3 pages.

* cited by examiner

*Primary Examiner* — David Rines
(74) *Attorney, Agent, or Firm* — Husch Blackwell LLP

(57) ABSTRACT

An imaging and workflow method, system, computer readable medium and user interface for processing information efficiently for the processing of medical prescription orders. The system includes support for document scanning, automated rules-based order processing, statistical reporting, document generation and document storage and retrieval. The present invention takes advantage of imaging technology to assist the user in scanning information into the system and software modules to improve the processing of orders. The present invention also includes database tables that identify to application processing logic the types and sequences of actions to be implemented for orders.

30 Claims, 64 Drawing Sheets

MASTER PROTOCOL LIST (SORTED ALPHABETICALLY)

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| P | #RXWG | #RXS MISMATCH (*N1IO/*N2IO) | | | |
| P | $CHCK | RX COST *N1I2; CHECK CODING | X | | |
| S/A | ?CA1 | CUSTOMER ADDRESS PENDED LINE #1 | CUSTOMER SERVICE-CUSTOMER DATA | | |
| P | ?CA2 | CUSTOMER ADDRESS PENDED LINE #2 | X | | |
| S/A | ?CCT | CUSTOMER CITY PENDED | CUSTOMER SERVICE-CUSTOMER DATA | | |
| A | ?CFN | CUSTOMER FIRST NAME PENDED | CUSTOMER SERVICE-CUSTOMER DATA | | |
| A | ?CLN | CUSTOMER LAST NAME PENDED | CUSTOMER SERVICE-CUSTOMER DATA | | |
| A | ?COB | COB PENDED | CUSTOMER SERVICE-CUSTOMER DATA | | |
| A | ?CPH | CUSTOMER PHONE NUMBER PENDED | CUSTOMER SERVICE-CUSTOMER DATA | | |
| A | ?CST | CUSTOMER STATE PENDED | CUSTOMER SERVICE-CUSTOMER DATA | | |
| A | ?CZ4 | CUSTOMER ZIP CODE +4 PENDED | CUSTOMER SERVICE-CUSTOMER DATA | | |
| S/A | ?CZP | CUSTOMER ZIP CODE PENDED | CUSTOMER SERVICE-CUSTOMER DATA | | |
| P | ?DAD | DOCTOR ADDRESS PENDED | X | | |
| P | ?DCT | DOCTOR CITY PENDED | X | | |
| P | ?DDY | DOSES-DAY PENDED | | | |
| P | ?DEA | DOCTOR DEA NUMBER PENDED | X | | |
| P | ?DFN | DOCTOR FIRST NAME PENDED | X | | |
| P | ?DLN | DOCTOR LAST NAME PENDED | X | | |
| P | ?DPH | DOCTOR PHONE NUMBER PENDED | | | |
| P | ?DRG | DRNO PENDED | X | | |
| P | ?DRGI | NO DESCRIPTION | | | |
| P | ?DRUG | VERIFY/CLARIFY DRUG | | | |
| S | ?DSF | DOCTOR DEA SUFFIX PENDED | X | | |
| P | ?DST | DOCTOR STATE PENDED | X | | |
| P | ?DYS | DAYS SUPPLY PENDED | | | |
| P | ?EXP | EXP/PRN DAYS PENDED | X | | |
| A | ?GPR | GROUP-REQ PENDED | ELIG-OTHER | | |
| P | ?IDT | ISSUE DATE PENDED | X | | |
| A | ?MBN | MEDICARE B NUMBER PENDED | ELIG-OTHER | | |
| P | ?MDW | DOCTOR DAW PENDED | | | |
| P | ?MSG | MESSAGE PENDED | | | |
| A | ?PAG | PATIENT AGE PENDED | NON-PENDABLE | | |

FIG. 24

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| A | ?PBD | PATIENT BIRTH DATE PENDED | ELIGIBILITY-PATIENT DATA | | |
| A | ?PCD | PATIENT CLNT-DEPNO PENDED | ELIGIBILITY-PATIENT DATA | | |
| A | ?PCL | PATIENT CLASS PENDED | ELIGIBILITY-PATIENT DATA | | |
| A | ?PDP | PATIENT DEPENNO PENDED | ELIGIBILITY-PATIENT DATA | | |
| P | ?PDW | PATIENT DAW PENDED | X | | |
| P | ?PFN | PATIENT FIRST NAME PENDED | X | | |
| P | ?PLN | PATIENT LAST NAME PENDED | X | | |
| P | ?POV | PRICE OVERRIDE PENDED | | | |
| A | ?PSX | PATIENT SEX PENDED | ELIGIBILITY-PATIENT DATA | | |
| P | ?QAC | QUANTITY ACTUAL PENDED | | | |
| P | ?QOR | QUANTITY ORIGINAL PENDED | | | |
| P | ?RAC | REFILLS ACTUAL PENDED | | | |
| P | ?RCD | NO DESCRIPTION | | | |
| A | ?RDT | RECEIVED DATE PENDED | NON-PENDABLE | | |
| P | ?ROR | REFILLS ORIGINAL PENDED | X | | |
| P | ?SIG | DIRECTIONS PENDED | X | | |
| P | ?TFM | TRIPLICATE FORM PENDED | | | |
| P | 2RX'S | MULTIPLE RX'S ON MASS BLANK | | | |
| A | ABDIS | AUTO BILL DISCONTINUED | AR-CREDIT CARDS | | |
| A | ABREQ | AUTO BILL REQUEST | AR-CREDIT CARDS | | |
| P | ADDHT | NO DESCRIPTION | | | |
| A | ADDR | ADPAY NAME/ADDRESS INCORRECT | DE-OTHER | | |
| P | AGLET | ATTORNEY GENERAL LETTER REQUIRED | X | | |
| P | APPET | APPETITE SUPPRESSANT; MASS MD | | | |
| A | APPNC | APPLIANCE NOT COVERED | PLAN RULES-COVERAGE | | |
| A | AR104 | INVALID COUPON AMOUNT FOR THIS G | AR-COUPONS | | |
| A | AR106 | PAY AMOUNT TOO LARGE. SENT TO A/ | AR-OTHER | | |
| A | AR108 | WRONG COUPON VALUE | AR-COUPONS | | |
| A | AR110 | NO COPAY REQUIRED FOR MED B | NON-PENDABLE | | |
| A | AR111 | NO COPAY REQUIRED, ELNM NO-COPAY | NON-PENDABLE | | |
| A | AR121 | INVOICE ALREADY INVOICED | NON-PENDABLE | | |
| A | AR122 | ELNM DATA MISSING | ELIG-OTHER | | |
| A | AR123 | 'NC' PMT TYPE INVALID FOR REPL | NON-PENDABLE | | |
| A | AR125 | DUPLICATE "BB" COUPON NOT | NON-PENDABLE | | |

FIG. 25

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| | | ALLOWED | | | |
| A | AR202 | YOU CANNOT UPDATE AR HERE | NON-PENDABLE | | |
| A | AR203 | *CAN'T UPDATE THIS PAY TYPE HERE | NON-PENDABLE | | |
| A | AR206 | COUPONS NOT ISSUED BY THIS GROUP | AR-COUPONS | | |
| A | AR207 | MEMBER COUPON LIMIT SURPASSED | AR-COUPONS | | |
| p | AR209 | ENTER DRUG (DRUG REC NOTFOUND) | | | |
| A | AR210 | NOT GENERIC DRUG - CAN NOT USE C | AR-COUPONS | | |
| A | AR211 | INVALID ENROLL CODE | ELIG-OTHER | | |
| A | AR212 | "CC" ALLOWED FOR CMS GROUP ONLY | AR-CREDIT CARDS | | |
| A | AR213 | "C1" ALLOWED FOR CMS GROUP ONLY | AR-CREDIT CARDS | | |
| A | AR214 | "C3" ALLOWED FOR CMS GROUP ONLY | AR-CREDIT CARDS | | |
| A | AR215 | TYPE "C1" NOT ALLOWED FOR GRP/SU | AR-CREDIT CARDS | | |
| A | AR216 | TYPE "C3" NOT ALLOWED FOR GRP/SU | AR-CREDIT CARDS | | |
| A | AR217 | TYPE "CC" NOT ALLOWED FOR GRP/SU | AR-CREDIT CARDS | | |
| A | AR218 | CREDIT CARD NOT ON FILE | AR-CREDIT CARDS | | |
| A | AR219 | CREDIT CARD EXPIRED | AR-CREDIT CARDS | | |
| A | AR221 | NRXRGN REC NOT FOUND | AR-CREDIT CARDS | | |
| A | AR222 | PRENATAL DRUGS ONLY FOR "CX" TYPE | AR-COUPONS | | |
| A | AR223 | CX COUPONS NOT ISSUED BY THIS GR | AR-COUPONS | | |
| A | AR224 | PC COUPONS NOT ISSUED BY THIS GR | AR-COUPONS | | |
| A | AR225 | CV COUPONS NOT ISSUED BY THIS GR | AR-COUPONS | | |
| A | AR226 | CE COUPONS NOT ISSUED BY THIS GR | AR-COUPONS | | |
| A | AR227 | "CY" TYPE ALREADY ENTERED | AR-COUPONS | | |
| A | AR228 | PHARMACY (TS-QUE) IS NOT CC AUTO | AR-OTHER | | |
| A | AR229 | NRXCTL REC IS NOT CC AUTO | AR-OTHER | | |
| A | AR230 | CC AUTH WILL BE HANDLED BY EOP | AR-CREDIT CARDS | | |
| A | AR231 | MEMBER NOT SETUP FOR INSTALLMENT | AR-OTHER | | |
| A | AR232 | INSTALLMENTS PAID IN FULL | AR-OTHER | | |

FIG. 26

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| A | AR233 | RX REC NOT FOUND | AR-OTHER | | |
| A | AR402 | INVOICE RECORD NOTFOUND | AR-OTHER | | |
| A | AR404 | CC ALREADY AUTHORIZED | AR-CREDIT CARDS | | |
| A | AR501 | ENTER MED-B (ELIG REC NOTFOUND) | ELIG-OTHER | | |
| A | AR502 | "Y" OR "N" REQUIRED IN MED-B-N | ELIG-OTHER | | |
| A | AR503 | ENTER MED-B (ELIG MED-B IND NOT | ELIG-OTHER | | |
| A | AR504 | ELIG MED-B CAN NOT USE COUPON | AR-COUPON | | |
| A | AR505 | VERIFY MED-B NUMBER | X | | |
| A | ARH01 | *N1I2 > FLOOR LIMIT | A/R-LIMITS | | |
| A | ARH02 | *N1I2 > PAST DUE | A/R-LIMITS | | |
| A | ARH03 | *N1I2 > COURTESY LIMIT | A/R-LIMITS | | |
| A | ARH04 | CAP EXCEEDED | AR-OTHER | | |
| A | ARH05 | GENERIC AVAILABLE | AR-OTHER | | |
| A | ARH06 | AUTHORIZATION DENIED | AR-OTHER | | |
| A | ARH07 | BILLING DENIED | AR-CREDIT CARDS | | |
| A | ARH08 | INSTALLMENT HOLD | AR-OTHER | | |
| A | ARH11 | FLOOR LIMIT | AR-LIMITS | | |
| A | ARH12 | MAX PAST DUE | MAX PAST DUE | | |
| A | ARH13 | COURTESY LIMIT | A/R-LIMITS | | |
| A | ARH14 | COPAY EXCEEDED | AR-OTHER | | |
| A | ARH15 | GENERIC AVAILABLE | AR-OTHER | | |
| A | ARH16 | BOUNCED CHECK | X | | |
| A | ARH17 | CUSTOMER SERVICE | X | | |
| A | ARH18 | LOST IN PHARMACY | CUSTOMER SERVICE-CUSTOMER DATA | | |
| A | ARH19 | NOT CUSTOMER SERVICE | X | | |
| A | ARH20 | COLLECTION AGENCY | X | | |
| A | ARH21 | GAP APPROVED | AR-OTHER | | |
| A | ARH22 | CREDIT CARD DENIED | AR-CREDIT CARDS | | |
| A | ARH23 | WIP BEFORE TRANSFER | AR-OTHER | | |
| A | ARH24 | CUST HAS COB | X | | |
| A | ARH30 | VERIFY CUSTOMER DATA | AR-OTHER | | |
| A | ARLMT | $ LIMIT EXCEEDED (*N1I2) | HIGH COST RECVIEW | | |
| A | ARMIS | MISCELLANEOUS FOR ACCOUNT REC | AR-OTHER | | |
| A | ARRTE | SEND TO ACCOUNTS RECEIVABLE | AR-OTHER | | |
| P | ASLET | ACCELERATED SUBSTITUION LETTER REQUIRED | X | | |
| P | ASLEX | NO DESCRIPTION | | | |

FIG. 27

| TEAM | REASON | PROTOCOL DESCRIPTION | CLUMPED | INTO: EXISTING (NAME)? GENERIC? SINGULAR? NONE (NOT IN ALPHA)? |
|---|---|---|---|---|
| P | AVONX | AVONEX; ATN C/S PHARMACIST | | |
| P | BBGRF | MULTISOURCE DRUG-GRANDFATHER | | |
| P | BBILG | BRAD RX ISSUED MORE THAN ONCE | X | |
| P | BEDNL | NO DESCRIPTION | | |
| P | BEDUN | DRUG UNAVAILABLE/DISCONTIUED | X | |
| A | BELLS | PATIENT DID NOT SIGN CLAIM FORM | CUSTOMER SERVICE-CUSTOMER DATA | |
| P | BEOTH | NO DESCRIPTION | | |
| P | BEQA2 | MISC BEQA2 NEVADA | | |
| P | BETAS | BETASERON; ATTN C/S PHARMACIST | | |
| P | BLSTR | BLISTER PACK REQUIRED | | |
| P | BLUCD | NO DESCRIPTION | | |
| P | BRAIL | BRAILLE LABEL REQUIRED | | |
| P | BRNDB | MULTISOURCE DRUG (BRAND B) | X | |
| P | BSC | NO DESCRIPTION | | |
| P | C2ALT | ALTERED C2 RX | | |
| P | C2DAT | C2 WITHOUT DATE | | |
| P | C2NON | NONCONTIGUOUS CII | | |
| P | C2QES | UNCLEAR C2 RX | | |
| P | C2RTE | NO DESCRIPTION | | |
| P | C2VER | CII VERIFICATION | | |
| A | CALPT | CALL PATIENT | CUSTOMER SERVICE-CUSTOMER DATA | |
| A | CCPAY | CHECK ENVELOP FOR CREDIT CARD | X | |
| P | CDRCH | CALL HELP DESK -DUR INCOMPLETE | | |
| P | CDRDA | DRUG ALLERGY ALERT | | |
| P | CDRMC | DRUG DISEASE PRECAUTION | | |
| P | CDRPA | DRUG AGE PRECAUTION | | |
| A | CHADD | | CUSTOMER SERVICE-CUSTOMER DATA | |
| P | CHDIR | | | |
| P | CHDRN | DRG NAME VER; LOOK/SOUND ALIKE | | |
| P | CHDRS | | | |
| P | CHGRX | RXCHG; NO MD CONTACT NO SOBA | | |
| P | CHIEF | SEND TO CHEIF RPH TO VERIFY | | |
| P | CHPNM | | | |
| P | CHRFL | | | |
| A | CMORF | CHECK MORF FOR PAYMENT INFORMATION | X | |
| P | CMPD | NO DESCRIPTION | | |

FIG. 28

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| P | CMPDS | CMPD RX;RTE COPY TO CMPD AREA | | | |
| P | CMPRX | COMPOUND RX CLARIFICATION | | | |
| P | CNTRL | CONTROL RX TAKE UD OR PRN | X | | |
| A | CPDRU | CALL PATIENT-DRUG UNAVAILABLE | CUSTOMER SERVICE-CUSTOMER DATA | | |
| A | CPMDU | CALL PATIENT-MD UNAVAILABLE | CUSTOMER SERVICE-CUSTOMER DATA | | |
| A | CPOOS | CALL PATIENT-DRUG OUT OF STOCK | CUSTOMER SERVICE-CUSTOMER DATA | | |
| A | CPTCH | CENTRAL PA TEAMSTERS-CHANGE | ELIG-OTHER | | |
| A | CPTCX | CENTRAL PA TEAMSTERS-CANCEL | ELIG-OTHER | | |
| A | CPTRX | CENTRAL PA TEAMSTERS-RX | ELIG-OTHER | | |
| P | CRIXI | CRIXIVAN: ATN C/S PHARMACIST | | | |
| A | CRIXR | CRIXIVAN ENROLL. REJECT | ELIG-OTHER | | |
| A | CRIXS | CRIXIVAN ENROLL. SERVER ERROR | ELIG-OTHER | | |
| P | CRXQA | CRIXIVAN SPECIAL HANDLING | | | |
| A | CSAAB | CS ADD AUTO BILL FLAG | AR-CREDIT CARDS | | |
| A | CSC11 | NONCONTIGUOUS CII | CUSTOMER SERVICE-CUSTOMER DATA | | |
| A | CSCAN | DRUG DISC/UNAVAIL; CUST SERVICE | X | | |
| A | CSDAB | CS DIC. AUTO BILL FLAG | AR-CREDIT CARDS | | |
| A | CSDEX | DEXEDRINE UNAVAILABLE; C/S | CUSTOMER SERVICE-CUSTOMER DATA | | |
| A | CSGEH | G.E.H.A. ROUTE TO CUSTOMER SERV | CUSTOMER SERVICE-CUSTOMER DATA | | |
| A | CSIMI | C/S IMITREX RX | CUSTOMER SERVICE-CUSTOMER DATA | | |
| A | CSMIS | MISCELLANEOUS FOR CUSTOMER SERV | CUSTOMER SERVICE-CUSTOMER DATA | | |
| A | CSRTE | ROUTE TO CUSTOMER SERVICE | CUSTOMER SERVICE-CUSTOMER DATA | | |
| A | CSRTL | RETAIL PHARMACY RX; ROUTE TO C/S | CUSTOMER SERVICE-CUSTOMER DATA | | |
| A | CSUNA | DRUG UNAVAILABLE; CUST SERVICE | CUSTOMER SERVICE-CUSTOMER DATA | | |
| P | CSVAC | NO DESCRIPTION | | | |
| A | CXERJ | NO NEW ENROLLMENT REJECT | AR-OTHER | | |
| P | CXLAL | NO DESCRIPTION | | | |
| P | DCANT | D/C; ANTIBIOTIC RECONSTITUTION | | | |
| P | DCDIG | DOCTOR CALL FOR DIAGNOSIS | | | |
| P | DCLMT | MIN/MAX DAYS SUPPLY ERROR | | | |

FIG. 29

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| P | DCMIS | MISCELLANEOUS FOR DOCTOR CALL | | | |
| P | DCPBD | VERIFY PATIENT DATE OF BIRTH | | | |
| P | DCPFN | VERIFY PATIENT FIRST NAME | | | |
| P | DCPPT | RETURN TO D/C; PER PATIENT | | | |
| P | DCRTE | ROUTE TO DOCTOR CALL | | | |
| P | DCSSN | D/C-NEED SSN FOR PRESCRIBER | X | | |
| P | DDMR | ORDER ENTRY REVIEW REQ. (DDDE) | | | |
| P | DDPBD | VERIFY PATIENT DATE OF BIRTH | | | |
| P | DDPFN | VERIFY PATIENT FIRST NAME | | | |
| A | DELIV | C/S ARRANGE FOR DELIVERY | CUSTOMER SERVICE-CUSTOMER DATA | | |
| P | DEMIS | MISCELLANEOUS FOR DATA ENTRY | | | |
| P | DETRN | NO DESCRIPTION | | | |
| P | DIABS | DIABETIC SUPPLY: CLARIF. REQUIRED | | | |
| P | DIFPT | 2 DIFFERENT PTS ON SAME RX | | | |
| P | DIRET | DIRECTION VERIFICATION | | | |
| P | DISCD | MAX DOSAGE EXCEEDED (*N215) | | | |
| P | DOD30 | MODIFY RX: 30 DAY COURTESY FILL | X | | |
| P | DODRF | DOD REPLACEMENT; USED NEXT FILL | | | |
| P | DODRP | DOD REPLACEMENT; 'Y' ON RFL SCR. | | | |
| P | DRG30 | DRUG UNAVAILABLE IN PHARMACY | X | | |
| M | DRG31 | PRUDENT PRESCR TARGET DRUG | | | |
| M | DRG32 | PRUDENT PRESCR PROACTIVE CALL | | | |
| P | DRG34 | GENERIC NOW AVAIL.; ACCEL SUBSTIT | | | |
| P | DRG38 | CHANGE TO MDD/REFORM OF PROD | | | |
| P | DRG39 | PRESCRIPTION ITEM NOW OTC | | | |
| P | DRG40 | CHANGE OF MANUFACTURER | | | |
| P | DRG41 | DRUG/PACKAGE REFORMULATED NO DC | | | |
| P | DRG42 | DRUG RECALL REPLACEMENT | X | | |
| P | DRG43 | NDP-ADS DRUG CHANGED TO MDS | | | |
| P | DRG44 | NO DESCRIPTION | | | |
| P | DRG52 | DISCONTINUED DRUGS | X | | |

FIG. 30

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| P | DRG53 | MANUFACTURE RECALL | X | | |
| P | DRG55 | NO DESCRIPTION | | | |
| P | DRG57 | NO DESCRIPTION | | | |
| P | DRG59 | P DRUG CHECK QUANTITY | | | |
| P | DRG63 | DUR REVIEW | | | |
| P | DRG64 | DUR REVIEW | | | |
| P | DRG72 | DOD NEW DRUG; NOT YET COVERED | X | | |
| P | DRG77 | NO DESCRIPTION | | | |
| P | DRGFL | DRUG NOT ON DRUG FILE | | | |
| P | DRGFR | DRUG FORM VERIFICATION | X | | |
| P | DRGNM | DRG NAME VER: LOOK/SOUND ALIKE | X | | |
| P | DRGST | DRUG STRENGTH VERIFICATION | X | | |
| P | DSMIS | MISCELLANEOUS FOR DRUG SPECIFIC | | | |
| P | DSRTE | ROUTE TO DRUG SPECIFIC | | | |
| P | DUR99 | NO DESCRIPTION | | | |
| P | DURDD | DRUG INTERACTION | | | |
| P | DURER | REFILL TOO SOON | | | |
| P | DURHD | MAX DOSAGE EXCEEDED (*N215) | X | | |
| P | DURTD | CONCOMMITANT/DUPLICATE THERAPY | | | |
| M | DYAZI | DYAZIDE RX; PRUDENT PRESCRIBING | | | |
| P | ECODE | CODING LEVEL 1 ERROR | | | |
| P | ED001 | DRUG NOT FOUND | | | |
| P | ED002 | INVOICE RECORD NOT FOUND | | | |
| P | ED004 | THIS DRUG CANNOT BE RENEWED | X | | |
| P | ED005 | COMPOUND PRICE MUST BE ENTERED | | | |
| A | ED007 | DISCONTINUED GRP | ELIG-OTHER | | |
| A | ED009 | SUBGRP NOT ACTIVE AT THIS PHARM | ELIG-OTHER | | |
| P | ED010 | REFILLS ONLY AT THIS PHARMACY | | | |
| P | ED011 | CONTROL RXS ONLY AT THIS PHARM | | | |
| P | ED012 | CNTRL RFLLS ONLY AT THIS PHARM | | | |
| A | ED013 | UNKNOWN PHARM-IND (SUBF1) | ELIG-OTHER | | |
| P | ED014 | DEA NUMBER REQUIRED | X | | |
| S | ED015 | DEA NUMBER INVALID | X | | |
| P | ED016 | DEA NO NOT FOUND ON DEA | | | |

FIG. 31

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| | | TABLE | | | |
| P | ED017 | DEA REQUIRED...(LEVEL B EDIT) | X | | |
| P | ED018 | NO PREVIOUS RX FOUND | | | |
| P | ED019 | PREVIOUS RX NOT FOUND | | | |
| P | ED021 | GROUP REQUIRES DEA NUMBER | | | |
| P | ED022 | MD NOT FOUND FOR LICENSE # | | | |
| P | ED023 | MD DEA NOT ON APPROVED LIST | | | |
| S | ED025 | DOCTOR ZIP CODE REQUIRED | X | | |
| P | ED026 | PAT-LST-NM NOT = CUST-LST-NM | X | | |
| A | ED027 | BC OF MASS NAME MISMATCH | ELIG-OTHER | | |
| P | ED028 | IF STAP ENTER 'STAP' OR 'MAP' | | | |
| P | ED030 | MSG REQ: 'AO' ON DUTY: 'FO' OTHER | | | |
| P | ED031 | WORK DAYS AGO CALC ERROR | | | |
| P | ED032 | LATE RX...REFER TO SUPERVISOR | | | |
| P | ED033 | LATE REASON CODE REQUIRED | | | |
| P | ED034 | MESSAGE FIELD ON NRX NOT VALID | | | |
| P | ED035 | MESSAGE FIELD ON NRX NOT VALID | | | |
| A | ED036 | CLAIM NO. INVALID/NOT FOUND | ELIGIBILITY-TERMED | | |
| A | ED037 | CLAIM BEGIN DATE > TODAYS DATE | ELIGIBILITY-TERMED | | |
| A | ED038 | CLAIM END-DATE < TODAYS DATE | ELIGIBILITY-TERMED | | |
| A | ED039 | MD LST-NM NOT VALID FOR CLAIM | ELIGIBILITY-TERMED | | |
| P | ED040 | REQUESTED RX NOT FOUND | | | |
| P | ED045 | MUST ENTER RESOLUTION | | | |
| P | ED049 | RESOLUTION IS INVALID | | | |
| P | ED053 | RX ALREADY PCOPY'ED | | | |
| P | ED055 | RX HAS BEEN PREVIOUSLY RENEWED | | | |
| P | ED057 | SUBRX ERR...RX ALREADY CHECKED | | | |
| P | ED058 | SUBRX ERR...RX NOT BRAND B | | | |
| P | ED060 | REQUESTED RX CMT IS TOO LARGE | | | |
| P | ED061 | LINK TO IESP3000 ERR: CALL MIS | | | |
| P | ED063 | GENERIC DRNO NOT FOUND | | | |
| M | ED064 | PRESC CHC DRUG...RSLTN REQ. | | | |
| A | ED065 | REC-DATE > ELIG TRANS DATE (EU) | ELIGIBILITY-TERMED | | |
| A | ED066 | CUSTOMER IS VOIDED | ELIGIBILITY-TERMED | | |
| P | ED068 | RX RECORD NOT FOUND | | | |

FIG. 32

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| P | ED069 | REFILL RECORD NOT FOUND | | | |
| A | ED071 | "Y" OR "N" REQ IN MED-B-NO | AR-OTHER | | |
| P | ED077 | RX NOT FOR THIS CUSTOMER | | | |
| P | ED079 | RX IS VOIDED | | | |
| P | ED080 | RX IS STOPPED | | | |
| P | ED081 | CONNECT CODE IS INVALID | | | |
| P | ED082 | CONTACT FIRST NAME REQUIRED | | | |
| P | ED084 | DUMMY DEA# CANNOT BE ENTERED | | | |
| P | ED087 | CANNOT CHG/CANCEL & REENTER | | | |
| P | ED089 | CTL RECORD NOT FOUND | | | |
| A | ED098 | INTERNAL CUSTNO INVALID BCBSNJ | ELIG-OTHER | | |
| A | ED108 | NO DESCRIPTION | ELIG-OTHER | | |
| A | ED110 | NO DESCRIPTION | ELIG-OTHER | | |
| P | ED112 | NO DESCRIPTION | | | |
| P | ED300 | ORIGINAL REFILL REC NOT FOUND | | | |
| P | ED301 | ORIG KEYP DATE CONVERT ERROR | | | |
| P | ED302 | CAN'T REFILL RX NOT YET CHECKED | | | |
| A | ED0303 | MUST REFILL IN ORIG PHARMACY | ROUTE TO PHARMACY-RULES | | |
| P | ED304 | CANNOT REFILL TOO MANY REFILLS | | | |
| A | ED306 | GROUP IS NOT EFFECTIVE | ELIGIBILITY-TERMED | | |
| A | ED307 | ISSUE DATE CONVERT ERROR | ELIG-OTHER | | |
| A | ED313 | CANNOT REFILL IN THIS PHARMACY | ROUTE TO PHARMACY-RULES | | |
| A | ED314 | NOT PRIMARY DISP LOC FOR CUST | ROUTE TO PHARMACY-RULES | | |
| A | ED315 | NOT DISPENSING LOC FOR NEW RX | ROUTE TO PHARMACY-RULES | | |
| P | ED318 | CANNOT FILL ANOREXIC IN OHIO | | | |
| P | ED319 | CAN'T FILL ANAB STER IN PHARM 12 | | | |
| P | ED320 | RX LOCKED AFTER ORDER REVIEW | | | |
| P | ED323 | RX STP 34; ACCEL; SUBSTITUTION | | | |
| A | ED324 | CUST HAS PREFERRED CARRIER | UPGRADE SHIPPING | | |
| A | ED325 | CUST HAS PREFERRED LVL OF SERV | UPGRADE SHIPPING | | |
| P | ED326 | DOCTOR CALL REQUIRED | | | |
| P | ED327 | ROUTE FOR RESOLUTION | | | |

FIG. 33

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| | | PROCESS | | | |
| A | ED328 | NON-MATCHED ELIGIBILITY | ELIGIBILITY-TERMED | | |
| A | ED329 | GROUP NO NOT ON CLIENT PROFILE | ELIGIBILITY-TERMED | | |
| A | ED330 | INV RQST TO RULE SRVR-CALL MIS | ROUTE TO PHARMACY-RULES | | |
| A | ED331 | RULE SERVER ERROR-CALL MIS | ROUTE TO PHARMACY-RULES | | |
| P | ED332 | RULE ENTRY LOC NOT = FILL NO | | | |
| P | ED333 | LONG DIRECTIONS PENDING | | | |
| P | ED334 | DIRECTIONS SHORT CODE INVALID | | | |
| P | ED335 | DIRECTIONS TOO LONG | | | |
| P | ED336 | DIRECT. TOO LONG; INV SHORT CD | | | |
| P | ED337 | DIRECTIONS INVALID | | | |
| A | ED338 | AUTOBILL = Y BUT CR CARD EXPIRED | AR-CREDIT CARDS | | |
| P | ED339 | RULES SVR RETURNED ZERO DISP-NO | ROUTE TO PHARMACY-RULES | | |
| P | ED340 | ROUTE TO CHIEF PHARMACIST | | | |
| P | ED344 | ROUTE TO CHIEF PHARMACIST | | | |
| P | ED350 | NO DESCRIPTION | | | |
| P | ED351 | NO DESCRIPTION | | | |
| P | ED353 | NO DESCRIPTION | | | |
| P | ED354 | NO DESCRIPTION | | | |
| P | ED355 | NO DESCRIPTION | | | |
| P | ED356 | NO DESCRIPTION | | | |
| P | ED357 | CA MD REQUIRES DUPLICATE | X | | |
| P | ED358 | DOD PT DAW = Y | X | | |
| P | EFINV | NO DESCRIPTION | | | |
| O | EHCDR | NO DESCRIPTION | | | |
| O | EHPHR | NO DESCRIPTION | | | |
| O | EHVND | NO DESCRIPTION | | | |
| O | EHWSS | NO DESCRIPTION | | | |
| O | EIFIX | NO DESCRIPTION | | | |
| A | EL001 | FUND DATA NOT FOUND | ELIG-OTHER | | |
| A | EL002 | DISCONTINUED GROUP | ELIGIBILITY-TERMED | | |
| A | EL003 | SUBFUND DATA NOT FOUND | ELIGIBILITY-TERMED | | |
| A | EL004 | TODAY IS BEFORE EFF DATE | ELIGIBILITY-GROUP DATA | | |
| A | EL010 | CANNOT OVERRIDE ELIGIBILITY | ELIG-OTHER | | |
| A | EL011 | NOT ELIGIBLE...AFTER CANCEL DA | ELIGIBILITY-TERMED | | |
| A | EL012 | COVERAGE SUSPENDED | ELIGIBILITY-TERMED | | |

FIG. 34

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| A | EL013 | CUSTOMER NOT ON ELIGIBILITY | ELIGIBILITY-NOT FOUND | | |
| A | EL014 | NO MEMBER/DEPENDENT RECORD | ELIGIBILITY-TERMED | | |
| A | EL015 | CLASS/MEMBER MISMATCH | ELIGIBILITY-TERMED | | |
| A | EL016 | CLASS/SPOUSE MISMATCH | ELIGIBILITY-TERMED | | |
| A | EL017 | CLASS DEPENDENT MISMATCH | ELIGIBILITY-TERMED | | |
| A | EL018 | MEMBER NOT ELIG (DATE) | ELIGIBILITY-TERMED | | |
| A | EL019 | POSITIVE COVERAGE REC NOT FOUN | ELIGIBILITY-NOT FOUND | | |
| A | EL020 | MEMBER NOT ELIGIBLE | ELIGIBILITY-TERMED | | |
| A | EL021 | SPOUSE NOT ELIGIBLE | ELIGIBILITY-TERMED | | |
| A | EL022 | DEPENDENT NOT ELIGIBLE | ELIGIBILITY-TERMED | | |
| A | EL023 | DEPENDENT IS OVER AGE | ELIGIBILITY-TERMED | | |
| A | EL024 | POSITIVE: MEMBER NOT ELIGIBLE | ELIGIBILITY-TERMED | | |
| A | EL025 | POSITIVE: SPOUSE NOT ELIGIBLE | ELIGIBILITY-TERMED | | |
| A | EL026 | POSITIVE: DEPENDENT NOT ELIGIB | ELIGIBILITY-TERMED | | |
| A | EL027 | EU BIRTH YY NOT ENTERED (POLICY | ELIGIBILITY-TERMED | | |
| A | EL028 | EU PAT NAME NOT ENTERED (POLICY | ELIG-OTHER | | |
| A | EL029 | EU BIRTH/PAT BIRTH YY MISMATCH | ELIGIBILITY-TERMED | | |
| A | EL030 | EU NAME / PAT NAME MISMATCH | ELIGIBILITY-TERMED | | |
| A | EL031 | BIRTH YY NOT = EEUNH BIRTH YY | ELIGIBILITY-TERMED | | |
| A | EL032 | SEX/REL MISMATCH CHK SEX/CLASS | ELIGIBILITY-TERMED | | |
| A | EL033 | DISP-DATE NOT WITHIN EFF-DATES | ELIGIBILITY-TERMED | | |
| A | EL034 | CUST DOES NOT HAVE FAM-COVERAG | ELIGIBILITY-TERMED | | |
| A | EL035 | PATIENT LAST NAME MISMATCH | ELIG-OTHER | | |
| A | EL036 | NOT ELIGIBLE...BEFORE EFF DATE | ELIGIBILITY-TERMED | | |
| A | EL037 | ADDRESS RELEASE REQUIRED | CUSTOMER SERVICE-CUSTOMER DATA | | |
| A | EL038 | CUSTOMER NUMBER UNKNOWN | ELIG-OTHER | | |
| A | EL039 | REC DATE > 21 DAYS AGO | NON-PENDABLE | | |
| A | EL040 | PATIENT VOIDED; CORRECT IN ELIG | ELIGIBILITY-TERMED | | |
| A | EL041 | MULT. GRP/SUBGRPS FOR CUSTNO | ELIGIBILITY-GROUP DATA | | |
| A | EL042 | ELIGIBLE IN MULT. GRP/SUBGRPS | ELIGIBILITY-GROUP DATA | | |
| P | EL043 | NAME/ADDR CHG'D AT DE; CHECK ID# | X | | |

FIG. 35

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| A | EL044 | CODE1 PRGM CAN'T COMPARE ADDRESS | ELIG-OTHER | | |
| A | EL045 | ELIG AND SPM ADDRESSES DIFFER | ELIG-OTHER | | |
| A | EL046 | ELIG DID NOT PROVDE AN ADDRESS | ELIG-OTHER | | |
| P | EL047 | DEPENDENT NO ON ELIGIBILITY FILE | ELIGIBILITY-NOT FOUND | | |
| A | ELAGE | AGE LIMITATION; ELIGIBILITY | ELIGIBILITY-TERMED | | |
| A | ELFWD | FORWARD TO ELIG; SEE COMMENTS | ELIG-OTHER | | |
| A | ELMIS | MISCELLANEOUS FOR ELIGIBILITY | ELIG-OTHER | | |
| A | ELMNF | POS; MEMBER NOT FOUND | ELIGIBILITY-TERMED | | |
| A | ELPAR | PRIOR AUTH REQ'D : ELIGIBILITY | PLAN RULES-COVERAGE | | |
| A | ELPNF | POS; PERSON NUMBER NOT FOUND | ELIGIBILITY-TERMED | | |
| A | ELPOA | POS; PATIENT OVERAGE | ELIGIBILITY-TERMED | | |
| A | ELPRA | PRIOR AUTH REQ'D: ROUTE TO ELIG | PLAN RULES-COVERAGE | | |
| A | ELRTE | ROUTE TO ELIGIBILITY | ELIG-OTHER | | |
| O | EMCAN | NO DESCRIPTION | | | |
| A | EMERG | EMERGENCY ORDER | CUSTOMER SERVICE-CUSTOMER DATA | | |
| O | EMINV | NO DESCRIPTION | | | |
| P | ES | NO DESCRIPTION | | | |
| O | ESVPT | NO DESCRIPTION | | | |
| A | EUCLR | ELIGIBILITY CLARIFICATION | ELIG-OTHER | | |
| A | EXPED | EXPEDITE SHIP (*T105 / *N112) | UPGRADE SHIPPING | | |
| P | FAXRN | NO DESCRIPTION | | | |
| P | FEPAT | FEP; RX APPEARS ALTERED | | | |
| P | FEPCX | FEP CANCELS FOR CORRECT SOBA | | | |
| P | FEPDN | FEP; DRUG NOT AVAIL. >72H | | | |
| P | FETAT | NO DESCRIPTION | | | |
| P | FFMIS | MISCELLANEOUS FOR FRONT PHARMACY | | | |
| P | FHAPP | FAX PROCESS ERROR/DOCTOR CALL | | | |
| P | FHC2D | C2 DRUG NOT FAXABLE | | | |
| P | FHCDR | COMPANY RULES PROHIBIT FAXING | | | |
| P | FHER1 | FX SVC UNAVAILABLE/DOCTOR CALL | | | |
| P | FHER2 | FX SVC UNAVAILABLE/DOCTOR CALL | | | |

FIG. 36

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| P | FHER3 | FX SVC UNAVAILABLE/DOCTOR CALL | | | |
| P | FHER6 | FX SVC UNAVAILABLE/DOCTOR CALL | | | |
| P | FHNOS | FAX NUMBER VERIFIED UNSECURE | | | |
| O | FHNVR | NO DESCRIPTION | | | |
| P | FHPHR | PHARMACY NOT FAXABLE | | | |
| P | FHPLN | PLAN DOES NOT ALLOW FAXING | | | |
| P | FHSTD | STATE PROHIBITS FAXING | | | |
| P | FHSYS | FAX PROCESS ERROR/DOCTOR CALL | | | |
| P | FHWSS | WRONG SOURCE SYSTEM: NOT FAXABLE | | | |
| O | FIDCR | NOT FAXABLE/DOCTOR CALL REQUIRED | | | |
| O | FIFIX | INV MAY BE FAXABLE/UPDATE DATA | | | |
| O | FIINV | INVOICE CONTENTS WILL BE FAXED | | | |
| O | FIUNV | FAX SERVICE UNAVAILABLE | | | |
| P | FRIDG | CANNOT SHIP - REFRIGERATION | | | |
| O | FSAPP | APPLIC. ERROR/CHECK FAX PROCESS | | | |
| O | FSNO# | NO FAX NUMBER ON FILE | | | |
| O | FSOLD | OLD FAX NUMBER | | | |
| P | FSUNS | UNSECURE FAX NUMBER | X | | |
| P | FSVDG | VERIFY DRUG INFORMATION | | | |
| P | FSVMB | VERIFY MEMBER INFORMATION | | | |
| P | FSVMD | VERIFY PRESCRIBER INFORMATION | X | | |
| P | FSVPT | VERIFY PATIENT INFORMATION | X | | |
| A | FV001 | CUSTOMER LST NM MUST BE ENTERED | NON-PENDABLE | | |
| A | FV002 | CUSTOMER FST NM MUST ENTERED | NON-PENDABLE | | |
| A | FV003 | CUSTOMER CITY MUST BE ENTERED | NON-PENDABLE | | |
| A | FV004 | CUSTOMER STATE MUST BE ENTERED | NON-PENDABLE | | |
| A | FV005 | CUSTOMER ZIP CODE INVALID | NON-PENDABLE | | |
| P | FV008 | MD FIRST NAME MUST BE ENTERED | | | |
| P | FV011 | MD ZIP CODE INVALID | X | | |
| P | FV022 | DRNO IS INVALID | | | |
| P | FV031 | NO DESCRIPTION | | | |

FIG. 37

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| P | FV032 | NO DESCRIPTION | | | |
| P | FV033 | NO DESCRIPTION | | | |
| P | FV040 | NO DESCRIPTION | | | |
| A | FV101 | INVALID CIN NUMBER (CUSTNO) | ELIG-OTHER | | |
| A | FV103 | CAMPBELLS DEPENNO MISSING | ELIG-OTHER | | |
| P | FV105 | ENTER BOTH CLASS AND DEPENNO | | | |
| A | FV106 | CLASS MUST BE "M" OR "S" | ELIG-OTHER | | |
| A | FV107 | CHECK CLASS AND/OR DEPENNO | NON-PENDABLE | | |
| P | FV109 | NO DESCRIPTION | | | |
| P | FV112 | DRNO CHECK DIGIT IS INVALID | | | |
| P | FV113 | ISSUE-DATE > TODAYS DATE | | | |
| P | FV115 | ISSUE DATE > RECEIVE DATE | | | |
| P | FV116 | RE-SCREEN FOR 180 DAY PLAN | | | |
| A | FV117 | ILG FUND MUST BE 001-998 | ELIG-OTHER | | |
| A | FV120 | ILG STATUS INVALID | ELIG-OTHER | | |
| A | FV121 | ILG LOCAL MUST BE 0001-9998 | ELIG-OTHER | | |
| P | FV122 | DIRECTIONS SHORT CODE INVALID | | | |
| P | FV123 | DIRECTIONS TOO LONG | | | |
| P | FV124 | DIRECT. TOO LONG;INV SHORT CD | | | |
| P | FV125 | DIRECTIONS INVALID | | | |
| P | FV300 | DAY SUPPLY OVERRIDE IS INVALID | | | |
| P | FV303 | REPLACEMENT QTY IS INVALID | | | |
| A | FV304 | MEMBER ADDRESS EQUAL SPACES | NON-PENDABLE | | |
| P | FV335 | DIRECTIONS TOO LONG | | | |
| O | FXCAN | FAX CANDIDATE | | | |
| P | GEHUN | GEHA ATTACHED RENEWAL | X | | |
| A | GHPRA | GROWTH HORMONE PRIOR AUTH | PLAN RULES-COVERAGE | | |
| P | GLYNA | GLYNASE; VERIFY NO SUBSTITUTION | | | |
| P | HCAMC | UNKNOWN ERROR | | | |
| P | HDRVF | FAXHEADER MUST BE VERIFIED | | | |
| P | HEP<3 | HEP VACC < 3 DOSES - ST OF MAINE | | | |
| A | HEPAT | HEPATITIS VACC COPAY FOR MAINE | AR-OTHER | | |
| P | HICRX | HIGH COST PRESCRIPTION | | | |
| P | HOLD | HOLD; AVAIL. <72H | | | |
| P | HTYPE | HAND TYPE: LONG SIG/CMPD ETC. | | | |
| P | HUMHB | NO DESCRIPTION | | | |

FIG. 38

| TEAM | REASON | PROTOCOL DESCRIPTION | CLUMPED | INTO: EXISTING (NAME)? GENERIC? SINGULAR? NONE (NOT IN ALPHA)? |
|---|---|---|---|---|
| P | IGIL | IGI LETTER REQUIRED | | |
| P | ILLEG | ILLEGAL RXS (BLANK) | X | |
| P | IMITX | IMITREX: KIT OR PREFILLED SYRIN | | |
| P | LACR1 | LACRISERT; UNAVAILABLE | | |
| P | LEVL2 | LEVEL 2 DRUG VERIFICATION TEXAS | X | |
| P | LGPRT | LARGE PRINT LABEL REQUIRED | | |
| P | LGSIG | DIRECTIONS GREATER THAN 144 CH | | |
| P | LSTML | NO DESCRIPTION | | |
| P | MACPR | ZERO MAC PRICE ON NDC FILE | | |
| M | MCLET | MANAGED CARE LETTER REQUIRED | X | |
| P | MD002 | ENTER PHYSICIAN FIRST NAME | X | |
| P | MD004 | ENTER PHONE NUMBER | X | |
| P | MD005 | ADDITIONAL MD INFO REQUIRED | | |
| P | MDDEF | MD DEFAULT (DOCTOR NOT ON FILE) | X | |
| P | MDDUP | MD DEFAULT DUPLICATE MD ON FILE | | |
| P | MDSIG | DOCTOR SIGNATURE MISSING | X | |
| P | MDSSN | SSN FOR PRESCRIBER REQ'D | X | |
| P | MDVER | DOCTOR CALL FOR VERIFICATION | X | |
| P | MDWCB | DOCTOR WILL CALL BACK | | |
| A | MEMAD | VERIFY MEMBER ADDRESS | CUSTOMER SERVICE-CUSTOMER DATA | |
| P | MEMCT | VERIFY MEMBER CITY | X | |
| A | MEMFN | VERIFY MEMBER FIRST NAME | CUSTOMER SERVICE-CUSTOMER DATA | |
| A | MEMLN | VERIFY MEMBER LAST NAME | CUSTOMER SERVICE-CUSTOMER DATA | |
| A | MMNM | NAME IS WRONG; CXL ALL; RE-ENTER | ELIG-OTHER | |
| P | MEMSS | VERIFY MEMBER SS # | X | |
| P | MEMST | VERIFY MEMBER STATE | X | |
| A | MEMZP | VERIFY MEMBER ZIP CODE | CUSTOMER SERVICE-CUSTOMER DATA | |
| P | MIRL | NO DESCRIPTION | | |
| P | MLSRX | NO DESCRIPTION | | |
| P | MUSTA | MUSTARGEN; REQUIRES CASE NUMBER | | |
| P | N | NO DESCRIPTION | | |
| P | NDPBC | NO DESCRIPTION | | |
| P | NDPCN | NDP; BACKEND CANCEL | | |
| P | NDPSP | NDP; BACKEND SPLIT ORDER | | |

FIG. 39

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| P | NFDNA | NON FEP; DRUG NOT AVAIL. >72H | | | |
| P | NJRXF | CHECK RX FOR NJ REQ'D FORMAT | | | |
| P | NONSF | NO DESCRIPTION | | | |
| A | NOPAY | PAYMENT NOT INDICATED | AR-OTHER | | |
| P | NOTMS | NON SUITABLE FOR MAIL SERVICE | | | |
| P | NOTRX | NOT A PRESCRIPTION | | | |
| P | NRXNO | DRUG NOT DISPENSED BY NRX | | | |
| P | OER | ORDER ENTRY REVIEW REQUIRED | | | |
| P | OER2 | ORDER ENTRY REVIEW REQUIRED(2) | | | |
| P | OERIP | ORDER REVIEW IN PROCESS | | | |
| P | OERNB | ORDER ENTRY REVIEW REQUIRED(NB) | | | |
| P | OERSP | ORDER ENTRY REVIEW REQUIRED(SP) | | | |
| P | OFS00 | IN STOCK;OBTAINED RX;NO CONTAC | | | |
| P | OFS01 | CXL; MD REQ RX RETURN S022 | | | |
| P | OFS02 | RXCHG;MD CHANGED RX | | | |
| P | OFS03 | CXL;MD CHANGED RX | | | |
| P | OFS04 | CXL;RETURNED RX | | | |
| P | OFS05 | MD REQ. PT TO WAIT | | | |
| P | OFS06 | PT REQ. WAIT | | | |
| P | OFS07 | CXL. CAN'T REACH PT/MD | | | |
| A | OFS09 | PT TO CALL; CS CALL PT | CUSTOMER SERVICE- CUSTOMER DATA | | |
| A | OHPRA | POS; PRIOR AUTH REQUIRED | PLAN RULES- COVERAGE | | |
| P | OHTRF | PT REQUEST WAIT>72H;CXL&HOLD | | | |
| A | OOSNF | OUT OF STOCK NON-FEP;CALL PT | CUSTOMER SERVICE- CUSTOMER DATA | | |
| P | OOSTK | OUT OF STOCK | X | | |
| P | OPTOM | TX OPTOMETRIST DRUG VERIFICATION | | | |
| A | ORFL? | REFILL FROM OLD VENDOR; RETURN | CUSTOMER SERVICE- CUSTOMER DATA | | |
| P | ORNCR | ORDER REVIEW NONCONFORMANCE; QA2 | | | |
| P | OSTMY | OSTOMY PRODUCT | | | |
| P | OTCNC | OTC NOT COVERED | PLAN RULES- COVERAGE | | |
| P | PITRF | HARRISBURG TRANSFER; TWIP | | | |

FIG. 40

| TEAM | REASON | PROTOCOL DESCRIPTION | CLUMPED | INTO: EXISTING (NAME)? GENERIC? SINGULAR? NONE (NOT IN ALPHA)? |
|---|---|---|---|---|
| P | PANNE | NO DESCRIPTION | | |
| A | PATNM | VERIFY PATIENT NAME | CUSTOMER SERVICE-CUSTOMER DATA | |
| A | PAYCC | CHECK FOR PAYMENT WITH THE ORDER | X | |
| A | PAYMT | ORDER PAYMENTS INCORRECT | X | |
| A | PHARM | SEND TO CORRECT PHARMACY | CUSTOMER SERVICE-CUSTOMER DATA | |
| P | PHOTO | PHOTOCOPIED RX | | |
| A | PIKUP | C/S ARRANGE FOR PICK UP | CUSTOMER SERVICE-CUSTOMER DATA | |
| P | PIRF | PHONE IN REFILL | | |
| P | PL001 | GRP DOES NOT COVER C OR N DRUGS | | |
| P | PL002 | GRP DOES NOT COVER "N" DRUGS | | |
| P | PL003 | GRP DOES NOT COVER "C" DRUGS | | |
| P | PL004 | GRP DOES NOT COVER DRUG(EXCL) | | |
| P | PL005 | BRAND FOR GENERIC DRUGS EXCL. | | |
| P | PL006 | ENTER FEP CONTROLS AT TAMPA II | | |
| P | PL007 | GRP DOES NOT COVER BRAND B DRGS | | |
| M | PL008 | ILG NON-FORM., SEND TO PRU PRESC | | |
| P | PL009 | DRUG DRNO NOT COVERED(EXCL) | | |
| P | PL010 | DRUG NDC-NO NOT COVERED(EXCL) | | |
| P | PL011 | PRIOR AUTH:CAN'T OVRD RULES | | |
| P | PL012 | DRUG NOT FOUND | | |
| A | PL013 | NSRULE BAD STATUS FLAG FOR GRP | PLAN RULES-COVERAGE | |
| P | PL014 | DRUG NOT INCLUDED IN COVERAGE | | |
| P | PL015 | DRUG CATEGORY = ZERO | | |
| P | PL016 | DRUG CATEGORY NOT COVERED | | |
| A | PL017 | DRUG NOT COVERED (PRIOR AUTH) | PLAN RULES-COVERAGE | |
| P | PL018 | SUBFUND NOT FOUND | | |
| S | PL019 | PLAN RULES DATE > TODAY | PLAN RULES-COVERAGE | |
| P | PL022 | QTY-ACT MUST BE 1 | | |
| P | PL023 | DOSES-DAY MUST BE 99.9 | | |
| P | PL024 | CALCULATED DOSES-DAY IS 0 | | |

FIG. 41

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| P | PL025 | QTY-ORIG CALCULATION ERROR | | | |
| P | PL026 | DAYS-SPLY *N110<PLN MIN *N210 | PLAN RULES-LIMITS | | |
| P | PL029 | PREPACK DRUG QTY > 9 | | | |
| P | PL030 | QTY-ACT MUST BE > 0 | | | |
| P | PL031 | QTY-ACT > QTY-ORIG | | | |
| P | PL032 | NOT A P-DRUG;CHECK QTY | | | |
| P | PL033 | QTY-ACT > NARCOTIC LIMIT | | | |
| P | PL034 | QTY-ACT > CONTROLS LIMIT | | | |
| P | PL035 | QTY CANNOT EXCEED 300 (CAT 03) | | | |
| P | PL036 | 5 RFLLS ALLOWED; CALL MD FOR CHG | | | |
| P | PL037 | CALCULATED DAYS SUPPLY < 1 | | | |
| P | PL038 | REFILLS ACT EXCEEDS LIMIT | | | |
| P | PL039 | GRP ALLOWS UP TO 5 REFILLS | | | |
| P | PL041 | REFILLS MUST BE < 6 (CONTROLS) | | | |
| P | PL043 | ISSUE-DATE MORE THAN YEAR AGO | X | | |
| P | PL044 | ISSUE-DATE MORE THAN 6 MO AGO | X | | |
| P | PL045 | PRN NOT DEFINED FOR YOUR PHARM | | | |
| P | PL046 | CAN'T ENTER BOTH PRN + # RFLLS | | | |
| P | PL047 | EXP DAYS UP TO 182 ALLOWED | | | |
| P | PL048 | EXP DAYS UP TO 365 ALLOWED | | | |
| P | PL049 | RX EXPIRED BASE ON ISSUE/EXP | X | | |
| P | PL050 | ISSUE-DATE > 19 DAYS AGO | | | |
| P | PL051 | ILG ALLOWS 30 DYS FOR HALCION | | | |
| P | PL052 | PRN # REFILS EXCEEDED | | | |
| A | PL053 | PRIOR AUTH # REFILS EXCEEDED | PLAN RULES-COVERAGE | | |
| A | PL054 | PRIOR AUTH DOES NOT ALLOW RFLLS | PLAN RULES-COVERAGE | | |
| P | PL055 | NARCOTIC DAYS SUPPLY > 30 | | | |
| P | PL056 | NARCOTIC DAYS SUPPLY > 60 | | | |
| P | PL057 | NARCOTIC DAYS SUPPLY > 90 | | | |
| P | PL058 | NARCOTIC DYS > 180 - STEROIDS | | | |
| P | PL059 | CONTROL DAYS SUPPLY > 100 | | | |
| P | PL060 | CIII DAYS SUPPLY > 30 | | | |
| P | PL061 | NOT MEETING MIN DYS/RFL REQ. | | | |

FIG. 42

| TEAM | REASON | PROTOCOL DESCRIPTION | CLUMPED | INTO: EXISTING (NAME)? GENERIC? SINGULAR? NONE (NOT IN ALPHA)? |
|---|---|---|---|---|
| P | PL062 | QTY > 100 AND DAYS SUPPLY > 60 | | |
| P | PL063 | QTY > 270 AND DAYS SUPPLY > 90 | | |
| P | PL064 | QTY AND DYS EXCEED GRP LIMITS | | |
| P | PL065 | NOT METTING MIN DYS/RFLL REQ. | | |
| P | PL066 | QTY > PLAN ALLOWS | PLAN RULES-LIMITS | |
| P | PL067 | CONTROL DRUG DYS > LIMIT | | |
| P | PL068 | DAYS-SPLY *N1IO > PLN MAX *N2IO | PLAN RULES-LIMITS | |
| P | PL069 | DAYS-SPLY *N1IO < PLN MIN *N2IO | PLAN RULES-LIMITS | |
| P | PL070 | REFILLS EXCEED CONTROL LIMIT | | |
| P | PL071 | NEEDLES/SYRINGE DYS > 180 | | |
| P | PL072 | PRN DAYS SUPPLY EXCEEDED | | |
| P | PL073 | EXP DAYS SUPPLY EXCEEDED | | |
| P | PL074 | RFLS > PLAN MAX RFL DAYS | | |
| P | PL075 | DRUG NOT COVERED FOR FEMALES | | |
| P | PL077 | HOME LIFE HIGH COST DRUG | | |
| P | PL078 | HIGH COST RX; CALL FOR APPROVAL | | |
| A | PL079 | CII RX;EUNH REC NOT CURRENT | PLAN RULES-LIMITS | |
| A | PL080 | CII RX;EUNH SS# NOT PRESENT | PLAN RULES-LIMITS | |
| P | PL081 | REGULATORY LATE CD: C DRUG | X | |
| P | PL082 | REGULATORY LATE CD: N DRUG | X | |
| P | PL083 | INVALID MD STATE FOR CII DRUG | | |
| P | PL084 | INVALID MD ZIP FOR CII DRUG | | |
| P | PL085 | CII DRUG NOT FROM TX DOCTOR | | |
| P | PL086 | CII DRUG: NEED TRIPLICATE FORM | | |
| P | PL087 | CONTROL DRUG, ISSUE DATE TOO OLD | X | |
| P | PL088 | > MAX DOSE; MUST ALSO OVR RULES | | |
| P | PL089 | >MAX DOSE; (DOR)(POR)(SOR) REQ. | | |
| P | PL090 | >MAX DOSE...CALL SUPERVISOR | | |
| P | PL091 | DEXEDRINE SPLY > 30 | | |
| P | PL092 | DEXEDRINE SPLY > 60 | | |
| P | PL093 | DEXEDRINE SPLY > 90 | | |
| P | PL094 | DEXEDRINE SPLY > 30 ADD/NARC | | |
| P | PL095 | QTY-ACT DEXEDRINE-ABUSE | | |
| P | PL096 | MD STATE REQ. TRIPLICATE/ BENZO | X | |
| P | PL097 | CIII ISSUE DATE > LIMIT | X | |
| P | PL098 | SC DOCTOR; QTY > 120 OR D/S> | | |

FIG. 43

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| | | 30 | | | |
| P | PL099 | CIII DRUG; ISSUE DAT > 30 DAYS | X | | |
| P | PL101 | ISSUE-DATE MORE THAN 6 MO AGO | X | | |
| P | PL102 | MD CALC DAYS EXCESSIVE(*N110) | | | |
| P | PL104 | CAN THIS BE D/D? (DOD) | X | | |
| P | PL300 | REFILLS NOT ALLOWED | | | |
| A | PL301 | CNTRL RXS ONLY AT THIS PHARMACY | ROUTE TO PHARMACY-RULES | | |
| A | PL302 | NO REFILLS FOR N-CONTROL DRUGS | PLAN RULES-LIMITS | | |
| A | PL303 | CANNOT REPLACE C OR N DRUGS | NON-PENDABLE | | |
| P | PL304 | CONTROL/NARCOTICS NOT COVERED | | | |
| A | PL305 | CNTRL DRUG REFILLS IN ORIG PHARM | ROUTE TO PHARMACY-RULES | | |
| P | PL306 | ORIG RX NOT ON FILE FOR 5 DAYS | | | |
| P | PL307 | GRP ONLY ALLOWS 180 DAYS/RX | | | |
| P | PL308 | OVER 180 DAY SINCE ORIG KEYP-DT | | | |
| P | PL309 | RX CHECKED WITHIN PAST 5 DAYS | | | |
| P | PL310 | SUPLY LEFT ALL FILLS > PLAN MAX | | | |
| P | PL311 | DYS-SUPPLY > PLAN MAX. USE PULLC | | | |
| P | PL312 | ORIG KEYP DATE CONVERT ERROR | | | |
| P | PL313 | ISSUE DATE CONVERT ERROR | | | |
| P | PL315 | RX IN FORCE OVER PLAN LIMIT | | | |
| P | PL316 | RITALIN DYS SPLY > 30 DYS | | | |
| P | PL318 | MD STATE REQ. DUPLICATE FORM | X | | |
| P | PL319 | NEEDLE/SYR. NEED DUPLICATE FORM | | | |
| P | PL320 | MD STATE REQ. TRIPLICATE FORM | | | |
| P | PL321 | SIG IS 'UD' DOCTOR CALL REQUIRED | | | |
| P | PL325 | OHIO ANOREXIANT EXCEEDS LIMIT | | | |
| P | PL326 | DELAWARE MD; QTY ACT > 100 | X | | |
| P | PL327 | NJ MD REQUIRES 'J' IN TRIP FIELD | X | | |
| A | PL800 | DRUG NOT COVERED BY PLAN | PLAN RULES-COVERAGE | | |

FIG. 44

| TEAM | REASON | PROTOCOL DESCRIPTION | CLUMPED | INTO: EXISTING (NAME)? GENERIC? SINGULAR? NONE (NOT IN ALPHA)? |
|---|---|---|---|---|
| P | PL801 | NDC NOT FOUND ON NDC MASTER | | |
| A | PL802 | PRIOR AUTHORIZATION REQUIRED | PLAN RULES-COVERAGE | |
| A | PL803 | PLAN SERVER COVERAGE IND ERROR | PLAN RULES-COVERAGE | |
| P | PL804 | DRUG NOT COVERED; SEX LIMITATION | PLAN RULES-COVERAGE | |
| A | PL805 | DRUG REQUIRES DRUG OVERRIDE | PLAN RULES-COVERAGE | |
| P | PL807 | NO DESCRIPTION | | |
| P | PL808 | NO DESCRIPTION | | |
| P | PL809 | NO DESCRIPTION | | |
| P | PL810 | NO DESCRIPTION | | |
| A | POS00 | SEE POSRS RECORD | POS-OTHER | |
| A | POS01 | (*T110*T210) | POS-OTHER | |
| A | POS02 | (*T110*T210) | POS-OTHER | |
| A | POS03 | (*T110*T210) | POS-OTHER | |
| A | POS04 | (*T110*T210) | POS-OTHER | |
| A | POS05 | PRVDR NOT FOUND | POS-OTHER | |
| A | POS06 | (*T110*T210) | POS-OTHER | |
| A | POS07 | INVLD CARD # | POS-OTHER | |
| A | POS08 | (*T110*T210) | POS-OTHER | |
| A | POS09 | INVLD DOB | ELIGIBILITY-TERMED | |
| A | POS10 | (*T110*T210) | POS-OTHER | |
| A | POS11 | INVLD RELATION | ELIGIBILITY TERMED | |
| A | POS12 | (*T110*T210) | POS-OTHER | |
| A | POS13 | (*T110*T210) | POS-OTHER | |
| A | POS14 | (*T110*T210) | POS-OTHER | |
| A | POS15 | (*T110*T210) | POS-OTHER | |
| A | POS16 | (*T110*T210) | POS-OTHER | |
| A | POS17 | (*T110*T210) | POS-OTHER | |
| A | POS18 | INVLD QUANTITY | POS EDITS | |
| A | POS19 | INVLD DAYS SPLY | POS EDITS | |
| A | POS20 | (*T110*T210) | POS-OTHER | |
| A | POS21 | NDC# NOTFOUND | POS EDITS | |
| A | POS22 | (*T110*T210) | POS-OTHER | |
| A | POS23 | INVLD ING COST | POS EDITS | |
| A | POS24 | (*T110*T210) | POS-OTHER | |
| A | POS25 | INV PRESCRIBER ID | POS-OTHER | |
| A | POS26 | (*T110*T210) | POS-OTHER | |
| A | POS27 | (*T110*T210) | POS-OTHER | |
| A | POS28 | (*T110*T210) | POS-OTHER | |

FIG. 45

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| A | POS29 | (*T110*T210) | POS-OTHER | | |
| A | POS30 | INVLD PRIOR AUTH | POS-OTHER | | |
| A | POS31 | (*T110*T210) | POS-OTHER | | |
| A | POS32 | (*T110*T210) | POS-OTHER | | |
| A | POS33 | (*T110*T210) | POS-OTHER | | |
| A | POS34 | (*T110*T210) | POS-OTHER | | |
| A | POS35 | (*T110*T210) | POS-OTHER | | |
| A | POS36 | (*T110*T210) | POS-OTHER | | |
| A | POS37 | (*T110*T210) | POS-OTHER | | |
| A | POS38 | (*T110*T210) | POS-OTHER | | |
| A | POS39 | (*T110*T210) | POS-OTHER | | |
| A | POS40 | PROVIDER NOT ON FILE | POS-OTHER | | |
| A | POS41 | MISC TPA ERROR MESSAGE | POS-OTHER | | |
| A | POS50 | PRVDR NOT FOUND | POS EDITS | | |
| A | POS51 | GROUP NOT FOUND | ELIGIBILITY-TERMED | | |
| A | POS52 | MEMBER NOT FOUND | ELIGIBILITY-NOT FOUND | | |
| A | POS53 | PERSON # NOT FOUND | ELIGIBILITY-TERMED | | |
| A | POS54 | NDC# NOTFOUND | POS-OTHER | | |
| A | POS55 | (*T110*T210) | POS-OTHER | | |
| A | POS56 | (*T110*T210) | POS-OTHER | | |
| A | POS57 | (*T110*T210) | POS-OTHER | | |
| A | POS58 | (*T110*T210) | POS-OTHER | | |
| A | POS59 | (*T110*T210) | POS-OTHER | | |
| A | POS60 | MISC TPA ERROR MESSAGE | POS-OTHER | | |
| A | POS61 | MISC TPA ERROR MESSAGE | POS-OTHER | | |
| A | POS62 | MISC TPA ERROR MESSAGE | POS-OTHER | | |
| A | POS64 | MISC TPA ERROR MESSAGE | POS-OTHER | | |
| A | POS65 | MEMBER INELIG | ELIGIBILITY-TERMED | | |
| A | POS66 | PNT OVERAGE | PLAN RULES-COVERAGE | | |
| A | POS67 | MEMBER INELIG | ELIGIBILITY-TERMED | | |
| A | POS68 | MEMBER INELIG | ELIGIBILITY-TERMED | | |
| A | POS69 | MEMBER INELIG | ELIGIBILITY-TERMED | | |
| A | POS70 | NDC# NOTCOVERED | PLAN RULES-COVERAGE | | |
| A | POS71 | (*T110*T210) | POS-OTHER | | |
| A | POS72 | (*T110*T210) | POS-OTHER | | |
| A | POS73 | (*T110*T210) | POS-OTHER | | |
| A | POS74 | (*T110*T210) | POS-OTHER | | |
| A | POS75 | PRIOR AUTH REQ | PLAN RULES-COVERAGE | | |
| A | POS76 | LIMITS EXCEEDED | PLAN RULES-LIMITS | | |

FIG. 46

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| A | POS77 | (*T110*T210) | POS-OTHER | | |
| A | POS78 | COST EXCEED MAX | POS-OTHER | | |
| P | POS79 | REFILL TOO SOON | | | |
| A | POS80 | (*T110*T210) | POS-OTHER | | |
| A | POS81 | (*T110*T210) | POS-OTHER | | |
| A | POS82 | (*T110*T210) | POS-OTHER | | |
| S/A | POS83 | DUP CLAIM PAID | POS EDITS | | |
| A | POS84 | CLAIM CAPTURED | POS-OTHER | | |
| A | POS85 | RX NOT PROCESSED | POS EDITS | | |
| A | POS86 | (*T110*T210) | POS-OTHER | | |
| A | POS87 | (*T110*T210) | POS-OTHER | | |
| A | POS88 | (*T110*T210) | POS-OTHER | | |
| A | POS89 | (*T110*T210) | POS-OTHER | | |
| A | POS90 | (*T110*T210) | POS-OTHER | | |
| A | POS91 | (*T110*T210) | POS-OTHER | | |
| A | POS92 | SYSTEM UNAVAIL | POS EDITS | | |
| A | POS93 | (*T110*T210) | POS-OTHER | | |
| A | POS94 | (*T110*T210) | POS-OTHER | | |
| A | POS99 | HOST PROCESS ERR | POS EDITS | | |
| A | POSE7 | METRIC DECIMAL QTY REJECT | POS-OTHER | | |
| A | POSHC | POINT OF SALE (POS) HIGH COST | HIGH COST REVIEW | | |
| A | POSPD | POS CLAIM: PAID SUCCESSFULLY | POS-OTHER | | |
| A | POSRJ | POINT OF SALE (POS) REJECT | POS-OTHER | | |
| M | PPAPP | PRUDENT PRESCR. APPROVED | X | | |
| M | PPCAN | PRUDENT PRESCR. CAND (*T102) | X | | |
| M | PPLET | MANAGED CARE LETTER REQUIRED | | | |
| M | PPMIS | MISCELLANEOUS FOR PRUDENT PRESC | X | | |
| A | PPMLR | PREPAID MAILER | CUSTOMER SERVICE-CUSTOMER DATA | | |
| M | PPRTE | ROUTE TO PRUDENT PRESCRIBING | X | | |
| A | PRAPP | VERIFY PRIOR APPROVAL | PLAN RULES-COVERAGE | | |
| P | PRFL | REVIEW PROFM SCREEN | | | |
| A | PRIOR | CALL CLIENT FOR PRIOR AUTH | PLAN RULES-COVERAGE | | |
| P | PROFL | PROFILE CLARIFICATION | | | |
| P | PRORV | PROFESSIONAL REVIEW | X | | |
| P | PTMRL | NO DESCRIPTION | | | |
| P | PTVER | NO DESCRIPTION | | | |
| P | QA2DI | DRUG DISCONTINUED; QA2 | | | |
| P | QA2UN | DRUG UNAVAILABLE; QA2 | | | |

FIG. 47

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| P | QAAUD | QA AUDIT | | | |
| P | QADEA | MD DEA MISSING FROM CONTROL RX | X | | |
| P | QADRU | QA DRUG FOR PRIORITY ORDERING | | | |
| P | QAMIS | PIRF CUSTOMER SERVICE COMMENTS | | | |
| P | QAMSC | MISCELLANEOUS FOR QUALITY ASSUR | | | |
| P | QAOER | QA; DRUG SPECIFIC ORDER REVIEW | | | |
| P | QAPBD | VERIFY DOB ON ORIG RX | | | |
| P | QAPFN | VERIFY PT NME ON ORIG RX | | | |
| P | QARTE | ROUTE TO QA-1 AREA | | | |
| P | QARVW | REVIEW FOR GRANDFATHERING | | | |
| P | QAUNA | DEXEDRINE AVAILABILITY; QA | | | |
| P | QSMIS | MISCELLANEOUS FOR QUICK START | | | |
| P | QSMR | ORDER ENTRY REVIEW REQ'D (QSRX) | | | |
| P | QSOER | QUICK START ORDER REVIEW REQ'D | | | |
| P | QT120 | CII CUT QYT TO 120 UNITS | | | |
| P | QT360 | CIV CUT QTY TO 360 DS | | | |
| P | QTY30 | CIII CUT QTY TO 30 DS | | | |
| P | QUINE | DRUG NOT COVERED FOR LEG CRAMPS | | | |
| P | REFRM | REFORMULATED BY MFG:D/C VERIFY | | | |
| P | RENCL | RENEWAL CLARIFICATION | X | | |
| P | RENNO | UNATTACHED RENEWAL | X | | |
| P | RETIN | RETIN A OVER AGE 26 | | | |
| P | RFLQT | REFILL QTY DIFFERENT FROM ORIG | | | |
| P | RFLSG | REFILL SIG DIFFERENT FROM ORIG | | | |
| P | RFPRN | PRN REFILLS = 0 | | | |
| P | RICHG | FRL RT FLAG CHANGED *T110 | | | |
| P | RLES | NO DESCRIPTION | | | |
| P | RTLRX | RETAIL PHARMACY RX | | | |
| A | RU001 | CUST AND/OR GRP ACTIVE IN *T103 | ROUTE TO PHARMACY-RULES | | |
| A | RU002 | RFLS MUST BE FILLED IN *T103 | ROUTE TO PHARMACY-RULES | | |
| A | RU003 | ENT CII FOR TX MD, CUS IN TX | ROUTE TO PHARMACY-RULES | | |

FIG. 48

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| A | RU004 | ENT C2 FOR NON-TX MD IN *T103 | ROUTE TO PHARMACY-RULES | | |
| A | RU005 | ENT CII FOR TX CUST IN *T103 | ROUTE TO PHARMACY-RULES | | |
| A | RU006 | UNUSED | ROUTE TO PHARMACY-RULES | | |
| A | RU007 | ENT BENZO FOR NY MD, CUS IN NY | ROUTE TO PHARMACY-RULES | | |
| A | RU008 | ENT BENZO FOR NON NY MD IN PA1 | ROUTE TO PHARMACY-RULES | | |
| A | RU009 | ENT BENZO FOR NY CUS IN PA1 | ROUTE TO PHARMACY-RULES | | |
| A | RU010 | ENT CII FOR CONTIG MD ST IN MA | ROUTE TO PHARMACY-RULES | | |
| A | RU011 | ENT CII NONCONTIG MD ST IN T1 | ROUTE TO PHARMACY-RULES | | |
| A | RU012 | ENT CII NONCONTIG MD ST IN T1 | ROUTE TO PHARMACY-RULES | | |
| A | RU013 | ENTER RITALIN IN OHIO | ROUTE TO PHARMACY-RULES | | |
| A | RU014 | ENTER DEXEDRIN IN OHIO | ROUTE TO PHARMACY-RULES | | |
| A | RU015 | ENTER NARCOTICS IN OHIO | ROUTE TO PHARMACY-RULES | | |
| A | RU016 | NO RXDIRECT FOR C2'S | ROUTE TO PHARMACY-RULES | | |
| A | RU017 | NO RXDRT FOR CONTROLS IN TX | ROUTE TO PHARMACY-RULES | | |
| A | RU018 | NO RXDRT FOR ANABOLIC IN TX | ROUTE TO PHARMACY-RULES | | |
| A | RU019 | NO RXDRT FOR ANOREXIC IN TX | ROUTE TO PHARMACY-RULES | | |
| A | RU020 | NO RXDIRECT FOR C2'S IN OHIO | ROUTE TO PHARMACY-RULES | | |
| A | RU021 | NO RXDRT FOR ANABLIC IN OHIO | ROUTE TO PHARMACY-RULES | | |
| A | RU022 | NO RXDRT FOR ANOREXIC IN OHIO | ROUTE TO PHARMACY-RULES | | |
| A | RU023 | RXDRT FOR NJ FEP CUS IN NJ ONLY | ROUTE TO PHARMACY-RULES | | |
| A | RU024 | RXDRT FOR T1 FEP CUS IN T1 ONLY | ROUTE TO PHARMACY-RULES | | |
| A | RU025 | NO RXDRCT FOR NON NJ FEP CUST | ROUTE TO PHARMACY-RULES | | |
| A | RU026 | NO RXDRT FOR NON T1 FEP CUST | ROUTE TO PHARMACY-RULES | | |
| A | RU027 | RFE; C2 FOR NON-TX MD IN *T103 | ROUTE TO PHARMACY-RULES | | |
| A | RU028 | ENTER NEW RXS IN *T103 | ROUTE TO PHARMACY- | | |

FIG. 49

| TEAM | REASON | PROTOCOL DESCRIPTION | CLUMPED | INTO: EXISTING (NAME)? GENERIC? SINGULAR? NONE (NOT IN ALPHA)? |
|---|---|---|---|---|
| A | RU029 | ENTER RFLS IN *T103 | ROUTE TO PHARMACY-RULES | |
| A | RU030 | ENTER REFILLS IN *T103 | ROUTE TO PHARMACY-RULES | |
| A | RU031 | PROCESS CONTROLS IN *T103 | ROUTE TO PHARMACY-RULES | |
| A | RU032 | NO QUICKSTART FOR NARCOTICS | ROUTE TO PHARMACY-RULES | |
| A | RU033 | NO QUCKSTRT FOR CONTROL DRUGS | ROUTE TO PHARMACY-RULES | |
| A | RU034 | PROCESS LONG DRCTNS IN *T103 | ROUTE TO PHARMACY-RULES | |
| A | RU035 | ANABOLIC FOR NY MD IN *T103 | ROUTE TO PHARMACY-RULES | |
| A | RU036 | ANABOLIC FOR NON NY MD IN PA | ROUTE TO PHARMACY-RULES | |
| A | RU037 | ANABOLIC FOR NY CUS IN PA1 | ROUTE TO PHARMACY-RULES | |
| A | RU038 | ANABOLIC FOR NON NY MD IN PA | ROUTE TO PHARMACY-RULES | |
| A | RU039 | CANNOT TRANSFER CONTROL REFILLS | ROUTE TO PHARMACY-RULES | |
| A | RU040 | ENTER UNKNOWN MD STATE IN *T103 | ROUTE TO PHARMACY-RULES | |
| A | RU041 | ENTER UNKNOWN MD STATE IN *T103 | ROUTE TO PHARMACY-RULES | |
| A | RU042 | ENTER CII FOR UNKNOWN MD IN *T103 | ROUTE TO PHARMACY-RULES | |
| A | RU043 | ORANGE BOOK DRUG SENT TO *T103 | ROUTE TO PHARMACY-RULES | |
| A | RU044 | CII'S FOR NON NY MD FILLED IN PA | ROUTE TO PHARMACY-RULES | |
| A | RU046 | OK TO PROCESS CONTROLS IN PA | ROUTE TO PHARMACY-RULES | |
| A | RU047 | COMPOUND CONTROLS IN *T103 | ROUTE TO PHARMACY-RULES | |
| A | RU051 | CONTROL REFILLS IN *T103 | ROUTE TO PHARMACY-RULES | |
| A | RU053 | CAREMARK CNTRL DO MD CALL IN NDP | ROUTE TO PHARMACY-RULES | |
| A | RU054 | CAREMARK NON-CNTRL PULLC IN NDP | ROUTE TO PHARMACY-RULES | |
| A | RU55 | CAREMARK NON-CONTROL PULLC IN OH | ROUTE TO PHARMACY-RULES | |
| A | RU56 | CAREMARK CNTRL: DO MD CALL IN OH | ROUTE TO PHARMACY-RULES | |
| A | RU57 | CAREMARK NON-CONTROL PULLC IN TX | ROUTE TO PHARMACY-RULES | |

FIG. 50

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| A | RU058 | CAREMARK CONTROL; NEED NEW RX | ROUTE TO PHARMACY-RULES | | |
| A | RU076 | NO DESCRIPTION | ROUTE TO PHARMACY-RULES | | |
| A | RU078 | NO DESCRIPTION | ROUTE TO PHARMACY-RULES | | |
| A | RU080 | NO DESCRIPTION | ROUTE TO PHARMACY-RULES | | |
| A | RU082 | NO DESCRIPTION | ROUTE TO PHARMACY-RULES | | |
| A | RU084 | NO DESCRIPTION | ROUTE TO PHARMACY-RULES | | |
| A | RU101 | NO DESCRIPTION | ROUTE TO PHARMACY-RULES | | |
| A | RU999 | NO DESCRIPTION | ROUTE TO PHARMACY-RULES | | |
| P | RWMR | ORDER ENTRY REVIEW REQ. (PIRN) | | | |
| P | RWOER | PHONE IN RENEWAL ORDER REVIEW | | | |
| P | RXALT | RX APPEARS ALTERED | | X | |
| P | RXCNT | NUMBER OF RXS MISMATCH | | | |
| P | RXCXL | CXL; RE-ENTER NO MD CONTA NO SO | | | |
| P | RXDIR | MISCELLANEOUS FOR RX DIRECT | | | |
| P | RXDIS | DRUG DISCONTINUED | | X | |
| P | RXDOH | RX DIRECT TRANSFER (OHIO) | | | |
| P | RXDTX | RX DIRECT TRANSFER (TEXAS) | | | |
| P | RXFIL | PT DOES NOT WANT ALL RXS FILLED | | | |
| P | RXMFG | HOLD RX-MANUFACTURER CHANGE | | | |
| P | RXMOV | DRUG MOVE IN PROGRESS IN NDP | | | |
| P | RXTRS | ORDER REVIEW-EXT TRANSFERRED RX | | | |
| P | RXUNA | DRUG UNAVAILABLE; DOCTOR CALL | | X | |
| P | SDURL | SENIORS DUR LETTER REQUIRED | | | |
| P | SEEEZ | NO DESCRIPTION | | | |
| P | SEEQ1 | NO DESCRIPTION | | | |
| P | SEEQ3 | NO DESCRIPTION | | | |
| P | SEEQ9 | NO DESCRIPTION | | | |
| P | SHLCN | SENIORS HELPLINE CALL NEEDED | | | |
| P | SHMIS | MISCELLANEOUS FOR SPECIAL HAND | | | |

FIG. 51

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| P | SIGST | MD SIGNATURE STAMPED/TYPED | X | | |
| P | SIGVR | DIRECTION VERIFICATION | | | |
| A | SM001 | SPECIAL MAILING REVIEW REQUIRED | UPGRADE SHIPPING | | |
| P | SPDRG | NO DESCRIPTION | | | |
| P | SPLIT | REFILL FROM ANOTHER PHARMACY | | | |
| P | STC | RX WAS CANCELLED BY STCXL | | | |
| P | STOCK | ROUTE TO FA;OOS | | | |
| P | SUPMD | NEED SUPERVISING MD NAME | | | |
| P | SURDA | SENIORS DRUG ALLERGY ALERT | | | |
| P | SURDD | SENIORS DRUG-DRUG EDIT | X | | |
| P | SURDL | SR DUR;BEQA2 PT LETTER REQUIRED | | | |
| P | SURDO | NO DESCRIPTION | | | |
| P | SURHD | SENIORS MAXIMUM DAILY DOSE | X | | |
| P | SURMC | SENIORS DRUG-DISEASE EDIT | X | | |
| P | SURPA | SENIORS DRUG-AGE EDIT | X | | |
| M | SWTCH | SWITCH BACK CLARIFICATION | | | |
| P | SYRIN | NO DESCRIPTION | | | |
| O | TEST | JEFF'S TEST PRADD ASSINED TO SV | | | |
| P | TORAD | TORADOL; CALL REQUIRED | | | |
| P | TRIPL | TRIPLICATE FORM (NY BENZODIAZEP) | | | |
| P | TRNAD | RTE TO FRONTEND TURNAROUND TEAM | | | |
| P | URCON | CONTROLLED DRUGS WITHIN 14 DAYS | | | |
| P | URDCP | POS; DUP CLAIM | X | | |
| P | URDUP | DUPLICATE DRUG, PAT., SAME DAY | | | |
| P | URIR | IDIOSYNCRASY REVIEW | | | |
| P | URMDD | POS; LIMITS EXCEEDED MDD | X | | |
| P | URMIS | MISCELLANEOUS FOR DUR | | | |
| P | URPCH | POS DUR...CALL HELP DESK | | | |
| P | URPCN | POS-DUR; CONTROLLED DRUG | X | | |
| P | URPDI | POS DUR - DRUG INTERACTION | | | |
| P | URPDA | POS DUR - DRUG-ALLERGY ALERT | X | | |
| P | URPDC | POS DUR - INFERRED DRUG-DISEASE | X | | |
| P | UPPDD | POS DUR - DRUG INTERACTION | X | | |
| P | URPDF | POS DUR - DRUG FOOD | | | |

FIG. 52

| TEAM | REASON | PROTOCOL DESCRIPTION | CLUMPED | INTO: EXISTING (NAME)? GENERIC? SINGULAR? NONE (NOT IN ALPHA)? | |
|---|---|---|---|---|---|
| | | INTERACTION | | | |
| P | URPDI | POS DUR - DRUG INCOMAPTIBILITY | | | |
| P | URPDL | POS DUR - DRUG LAB CONFLICT | | | |
| P | URPDO | POS DUR - DOD MAX DOSE EXCEEDED | X | | |
| P | URPDP | DUPLICATE DRUG PAT., SAME DAY | X | | |
| P | URPDS | POS DUR - TOBACCO USE PRECAUTION | | | |
| P | URPER | POS DUR-REF TOO SOON (*T120) | X | | |
| P | URPHD | POS DUR - MAX DOSAGE EXCEEDED | X | | |
| P | URPID | POS DUR - INGREDIENT DUPLICATION | | | |
| P | URPIR | IDIOSYNCRASY REVIEW | X | | |
| P | URPLD | POS DUR - LOW DOSAGE ALERT | X | | |
| P | URPLR | POS DUR - UNDERUSE PRECAUTION | | | |
| P | URPMC | POS DUR - DRUG DISEASE PRECATION | X | | |
| P | URPMN | POS DUR - INSUFFICIENT DURATION | | | |
| P | URPMX | POS DUR - EXCESSIVE DURATION | | | |
| P | URPOH | POS DUR - ALCOHOL PRECAUTION | | | |
| P | URPOV | POS DUR OVERFLOW...CALL TPA | | | |
| P | URPPA | POS DUR - DRUG AGE PRECAUTION | X | | |
| P | URPPG | POS DUR - DRUG PREGNANCY ALERT | | | |
| P | URPPR | POS DUR - PRIOR ADVERSE REACTION | | | |
| P | URPSX | POS DUR - DRUG-GENDER ALERT | X | | |
| P | URPTD | POS DUR - DUP/CONCOMITANT THRPY | X | | |
| P | URREF | REFILL TOO SOON | X | | |
| P | URRTE | ROUTE TO DUR | | | |
| P | URSDD | SEVERE DRUG INTERACTION | X | | |
| P | URSTD | SYSTEM ERROR | | | |
| A | VERAD | VERIFY CUSTOMER ADDRESS | CUSTOMER SERVICE-CUSTOMER DATA | | |
| P | VERPT | VERIFY PATIENT LAST NAME | X | | |
| P | WARD | NO DESCRIPTION | | | |
| P | WCAPG | DRUG PREGNANCY ALERT | X | | |
| P | XLBLR | EXTRA BOTTLE LABEL REQUEST | | | |

FIG. 53

PRESCRIPTION MANAGEMENT SYSTEM

RELATED APPLICATIONS

This application is a divisional patent application of U.S. patent application Ser. No. 10/134,638 filed on Apr. 30, 2002, issued on Feb. 17, 2009 as U.S. Pat. No. 7,493,263. This application is related to U.S. patent application Ser. No. 12/372,516, filed Feb. 17, 2009, which is also a divisional of U.S. patent application Ser. No. 10/134,638, issued on Feb. 17, 2009 as U.S. Pat. No. 7,493,263. All of the above applications are incorporated herein by reference.

FIELD OF INVENTION

The present invention relates generally to an image and workflow method, system, and medium for processing orders in the pharmacy industry. In particular, the present invention relates to a method, system, and medium for processing drug prescriptions in the mail order pharmacy industry.

BACKGROUND OF THE INVENTION

In the mail order pharmacy industry there exists a need to improve the quality and efficiency of processing medical prescriptions. The mail order pharmacy industry receives a tremendous number of orders on a daily basis, and it is not uncommon to receive 250,000 to 275,000 prescriptions within a single week per pharmacy location. Typically medical prescriptions must be filled in a very time efficient manner. Further, because errors in a prescription reaching a patient could be life threatening, a high level of quality control needs to be maintained throughout the entire prescription filling process.

The orders received from patients are frequently not in a condition to be filled directly without any additional processing. For instance, a prescription may be unreadable due to the illegible penmanship of the prescriber. Other conditions that impede the turnaround time of an order include, for example, a missing benefit plan membership number or the wrong or invalid benefit plan membership number; resolving any drug interactions a new prescription may present when taken with an existing patient condition or medication regime; the payment is missing; critical patient information is missing; the prescription is not covered by a patient's benefit's plan; and incorrect dosage or other dosage or usage inconsistencies. To resolve any of the above examples frequently requires the pharmacist or other technician working to fill the prescription to contact, for example, the prescriber, the patient, the member, the client or combinations thereof.

Presently, the pharmacy industry uses the physical paper order documents through the prescription filling process to process prescriptions. Reliance on the physical paper documentation is cumbersome and results in prescription processing delays. Under the current pharmacy model, as the orders for prescriptions come in they are reviewed and are assigned to a pan. A pan is a physical tray on which all the order documents are placed. Pans are typically color coded to correspond to each day of the week or some other such chronology related to order of receipt of an order. So for instance, if an order is received and opened on a Monday it would be placed in a red tray, which in this example is the Monday tray. To resolve any of the errors, questions, and/or conditions associated with an order may require a contact to the prescriber, the patient, the member, the client or combinations thereof. The prescriber is the individual responsible for writing the prescription contained in an order and is typically a medical doctor. The member is the individual that holds the benefit's plan. The patient can be a member but may instead be an individual named by the member, such as a family member, and covered by the benefit's plan. The client pays the bill in whole or in part associated with the drug and an administration fee to the mail order pharmacy and is typically the company or individual responsible for providing the benefit's plan to the member. For instance, if a prescription requires a call to the prescriber because the drug dosage is illegible, an attempt to contact the prescriber is made. If the attempt to contact the prescriber fails, a message may be left with the prescriber's office. When the prescriber returns the call the prescriber is typically subject to some wait time while the pharmacist or other technician goes through stacks of pans to locate the corresponding order. The resultant wait time typically results in some frustration on the part of the prescriber.

The current paper-based pharmacy system also suffers from the inability to locate the precise location of any one order. For instance, if a patient calls the pharmacy requesting an update on their order or if the patient needs to revise where the order is to be shipped, it is cumbersome to locate the order in an efficient manner that satisfies the patient. The lag time between when a patient calls to inquire about their prescription and when the order is located creates an ill impression of the pharmacy in the mind of the patient.

Another aspect of the present mail order pharmacy methods that create the misimpression that the pharmacy is slow to process orders results from the disparate geography of the patient and pharmacy. For example, if the mail order pharmacy is located in Seattle, Wash. and the patient is located in New York, N.Y. several days are lost just in order transit time—a few days to Seattle and a few additional days from Seattle to New York. It would be advantageous to be able to have the prescription mailed for processing to a pharmacy closer to New York, such as somewhere in New Jersey, to cut down on the mail transit time.

Furthermore, the present methods of mail order pharmacies cannot obtain intelligence on the health or state of the various system components involved in processing orders. More particularly, current methods are unable to provide real-time system state information.

Accordingly, we have determined an improvement upon the current system would provide real time state information regarding the condition of the system or any subcomponent of the system, the ability to locate an order at any time and in any location within the processing process, and the ability to process orders in locations distinct from the dispensing pharmacy.

SUMMARY OF THE INVENTION

It is therefore a feature and advantage of the present invention to provide a method for the automated processing of an order for at least one medical prescription received from a communication channel or other order entry process/system.

It is an additional and optional feature and advantage of the present invention to provide a system for the automated processing of an order for at least one medical prescription from a communication channel or other order entry process/system.

It is a further optional feature and advantage of the present invention to provide a graphical user interface for inputting, displaying, validating, and managing in real time a prescription fulfillment system, wherein the graphical user interface produces system reports and order statistics.

It is also an optional feature and advantage of the present invention to decrease reliance on paper files and manual document transmittal documents.

It is still another optional feature and advantage of the present invention to provide a computer-readable medium for the execution of an automated processing of an order for at least one medical prescription.

It is yet a further optional feature and advantage of the present invention to provide a computer-readable data structure for the automated processing of orders for at least one medical prescription accessed by a user interface sever program.

These and other objects and advantages of the present invention will be apparent to those of ordinary skill in the art upon inspection of the detailed description, drawings, and appended claims.

The present invention uses, for example, imaging technology to improve the quality and speed up the processing time of mail order prescriptions. The automated imaging environment of the present environment ensures timely and accurate handling of prescriptions and prescription review, as well as easier retrieval of complete workcase documentation. Flexible and configurable relational databases, applied to prescription orders reduces the overall prescription order processing time.

The present invention also reduces manual labor costs because the present invention preferably eliminates the need for manual labor to transport and sort orders progressing through the pharmacy. Additionally, the present invention preferably reduces labor costs, both in terms of time spent per order and the time required to train a new user for the system, by reducing the number of screens a user has to navigate through to progress the order through the system.

A scanner is used to read the information received through the mail into a computer file and/or memory in which a permanent likeness of the data can optionally be stored. The permanent record created of the order results in easy retrieval of the order.

Database parameters are manually keyed into an order record and are used to index the different types of incoming order documents. Different parameters are used to distinguish the different types of order documents. For instances, payment coupons are distinguished from actual prescriptions.

Other features of the system, method and medium include database tables which identify to the application processing logic the types and sequences of actions to implement for orders. In certain instances, these sequences are performed automatically. System level reports are also generated that can track the productivity, quality and performance at any system level.

NOTATIONS AND NOMENCLATURE

The detailed descriptions which follow may be presented in terms of program procedures executed on computing or processing systems such as, for example, a stand-alone gaming machine, a computer or network of computers. These procedural descriptions and representations are the means used by those skilled in the art to most effectively convey the substance of their work to others skilled in the art.

A procedure is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are machine operations. Useful machines for performing the operation of the present invention include general purpose digital computers or similar devices.

BRIEF DESCRIPTION OF THE DRAWINGS

These and other aspects, advantages, and novel features of the invention will become apparent upon reading the following detailed description and upon reference to accompanying drawings in which:

FIG. 2 is a screen capture illustrating an imaged order document.

FIG. 8 is a screen capture illustrating non-clinical data entry/verification.

FIG. 12 is a screen capture illustrating clinical data entry/verification.

FIGS. 24 to 53 includes examples of some of the protocols the present invention is capable of resolving.

DETAILED DESCRIPTION OF THE PREFERRED EMBODIMENTS

System Overview

Figure 1:
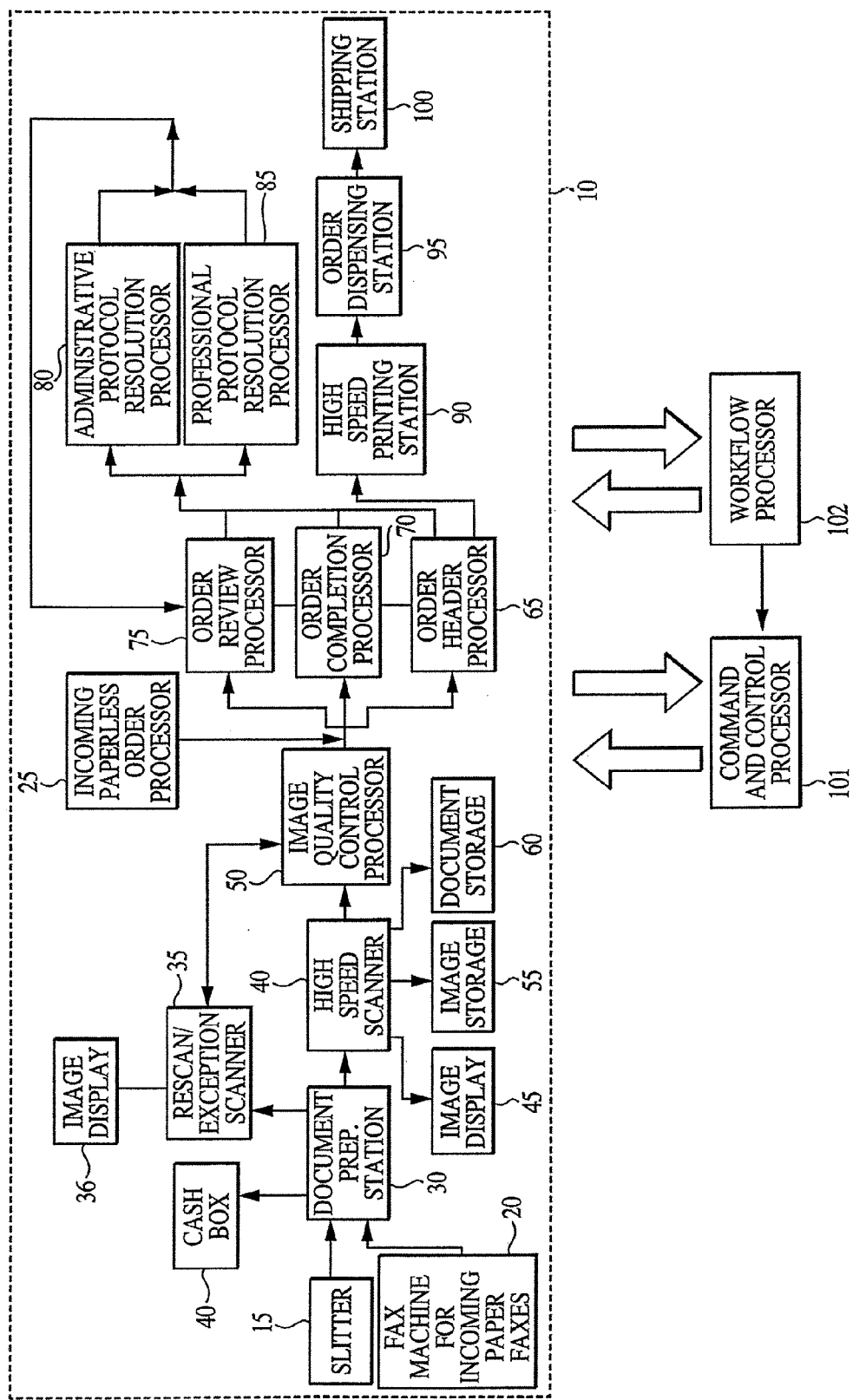
FIG. 1 is a block diagram illustrating the architecture of an embodiment of the order processing system of the present invention.

FIG. 1 is an example of a medical prescription order processing system 10 for practicing the present invention. In particular, a medical prescription order (also referred to as an order) is received by the system through at least one of a variety of communication channels to the system. The communication channels include both paper document channels, such as for example, mail (U.S. Post, commercial courier, such as for example, Federal Express®) manual facsimile, and the like; and paperless or electronic channels, such as for example, electronic facsimile, e-mail, phone call and the like. Order entry point or communication channels for order introduction into the system are found at the standard Slitter Processor 15, standard Facsimile Processor 20 for paper orders and at the standard Incoming Paperless Order Processor 25.

Received mail is processed and placed in condition to be scanned into the system. Mail enters the system at, for example, the Slitter Processor 15. The Slitter Processor 15 opens the envelopes and stamps the envelopes with predefined information which includes, for example, the date on which each envelope is opened by the Slitter Processor 15.

A similar preprocessing step is preformed on manual or paper faxes received through the manual fax communication channel to the Facsimile Processor 20. According to an alternative embodiment of the present invention, received manual faxes are bundled into paper batches along with received mail.

At the Document Preparation Processor 30 the contents of each envelope in a paper batch are reviewed and prepared for scanning. The entire contents of an envelope constitute an order. The open envelopes are combined into bundles of a predetermined number of envelopes. The bundles are then turned into paper batches. Each paper batch includes all the documents from a bundle and all associated preparation forms. Associated preparation forms include, for example, a batch header sheet which sits atop the paper batch, order separators which are used to separate the order, and a batch end sheet placed at the end of each paper batch. The contents of each envelope are assigned, when applicable under system protocols, to predefined document types or categories. Each document is affixed with a preprinted bar code label that identifies a document labeled with such as belonging to a particular document type. Document types include, for example, envelope—a distinction is made between system envelope and non-system envelopes; EasyRX/Universal Order Form (UOF); note—includes, for example, anything on which a member or patient has written information on; prescription refill; prescription renewal; payment coupon; payment—includes, for example, cash, checks and money orders; Health, Allergy and Medication Questionnaire (HAQ)—any type of member or patient health profile form; new prescription; non-scannable sheet—a sheet representing a document in an order which is not scannable; and other—includes anything that does not fit into a predefined category or document type. The order documents once ordered and affixed with the applicable bar code labels are sent to the High Speed Scanner 40 for imaging.

If the contents or a component of the documents of an order do not meet predefined criteria, such documents are pulled from the order, substituted with a nonscannable sheet, and optionally routed to an Exception Handling Processor 35. Documents routed to the Exception Handling Processor 35 include, for example, cash, three dimensional objects, such as, for example, empty prescription bottles, difficult to read items, difficult to scan documents or other documents that are not scannable by the High Speed Scanner Processor 40. If an order contains cash, the cash is counted and recorded at least in duplicate. The cash and at least one duplicate are deposited in a cash box 40 or deposit account and at least one duplicate is placed with the documents that make up the order from which the cash originated. Instead of scanning the cash included an order the recorded payment form is scanned. Other forms of receiving the cash may optionally be used. If an order contains a three dimensional object, such as, for example, an empty prescription bottle, the item is sent to the Exception Handling Processor 35. The Exception Handling Processor 35 takes account of the item and routes the record of the exception item to the order so the information contained in the item is available with the order for further order processing. In communication with the Exception Handling Processor 35 is an image display 36 for monitoring of the images captured by the Exception Handling Processor 35.

In communication with the High Speed Scanner Processor 40 is an image display 45 for monitoring the quality of the images captured. The scanned paper batches are reviewed according to a predetermined review audit schedule. According to an overlapping embodiment of the present invention, the predetermined review audit schedule is based on random selection, wherein only the scanned paper batches that are randomly selected are routed to the Image Quality Control Processor 50 for image review. Alternatively, all scanned paper batches may be utilized. Paper batches that are not selected for routing to the Image Quality Control Processor 50 are stored to a computer readable medium 55, such as, for example, computer memory, a computer hard disk drive, a magnetic tape drive, and/or a computer readable optical medium. The hard copies corresponding to the order images are stored or archived in a file room 60 in a predetermined manner that indexes them to their electronic images. According to an alternative embodiment of the present invention each scanned document in a paper batch has attached or associated with it a document identification number that is linked to its corresponding paper batch header identification number under which the paper batch is archived in the file storage room 60.

The paper batches that are selected for review are reviewed by a system user. If deficiencies are found to exist in the scanned images and the deficiencies exceed a predetermined threshold the entire paper batch is routed to the Rescanning/Exception Handling Processor 35. If after review by the Image Quality Control Processor 50 the images are found acceptable, the images are then stored to a computer readable medium, such as, for example, computer memory, a computer hard disk drive, a magnetic tape drive, and/or a computer readable optical medium. The hard copies corresponding to the order images are stored in a file room 60 in a predetermined manner that indexes them to their electronic images.

The paper batches once having been scanned and approved are routed to system queues for further order processing.

Depending on an order's contents the order will pass through at least one of Order Header Processor 65, Order Completion Processor 70, and/or Order Review Processor 75. The Order Header Processor 65, Order Completion Processor 70, and Order Review Processor 75 are each in communication with each other and with the Administrative Protocol Resolution Processor 80 and the Professional Protocol Resolution Processor 85.

The Order Header Processor 65 processes the non-clinical data associated with an order. Non-clinical data includes, for example, the number of prescriptions in an order; the prescription classification; the member number—as it relates to a benefits plan, the group number—as it relates to a benefits plan, and the sub-group number—as it relates to a benefits plan; the amount and type of payment, the patient/client correspondence; the prescriber name; patient/client name; and prescription issue date.

The Order Completion Processor 70 processes the clinical data associated with an order. Clinical data includes, for example, drug information, drug strength, drug usage directions, number of allowed refills, quantity of medication to dispense, and dosage per day.

The Order Review Processor 75 reviews all the elements of an order to determine whether the order elements are correct. Orders leaving the Order Review Processor 75 are routed to a High Speed Printing Processor 90 where the prescription labels and other accompanying order materials are printed. The drugs are then actually dispensed at the Order Dispensing Processor 95 and routed to the Shipping Station Processor 100 for shipment to the patient. For examples of Processors 90, 95, and 100 see for example U.S. Pat. No. 5,771,657 entitled "AUTOMATIC PRESCRIPTION FILLING, SORTING AND PACKAGING SYSTEM," incorporated herein by reference.

The Command and Control Processor 101 is in communication with each system processor and provides an interface through which real time information regarding, for example, system queues, order location, system resources, and system production is displayed, managed and processed. In alternative embodiments, a distributed control system and/or parallel processing system may be used. In still another embodiment of the present invention, the Command and Control Processor 101 is in communication with each system processor except system processors 90, 95, and 100.

The Workflow Processor 102 is in communication with each system processor and directs the flow of orders through the various system processors and work queues. The Workflow processor 102 also provides information to the Command and Control Processor 101.

The Imaged Order Documents

Figure 2:
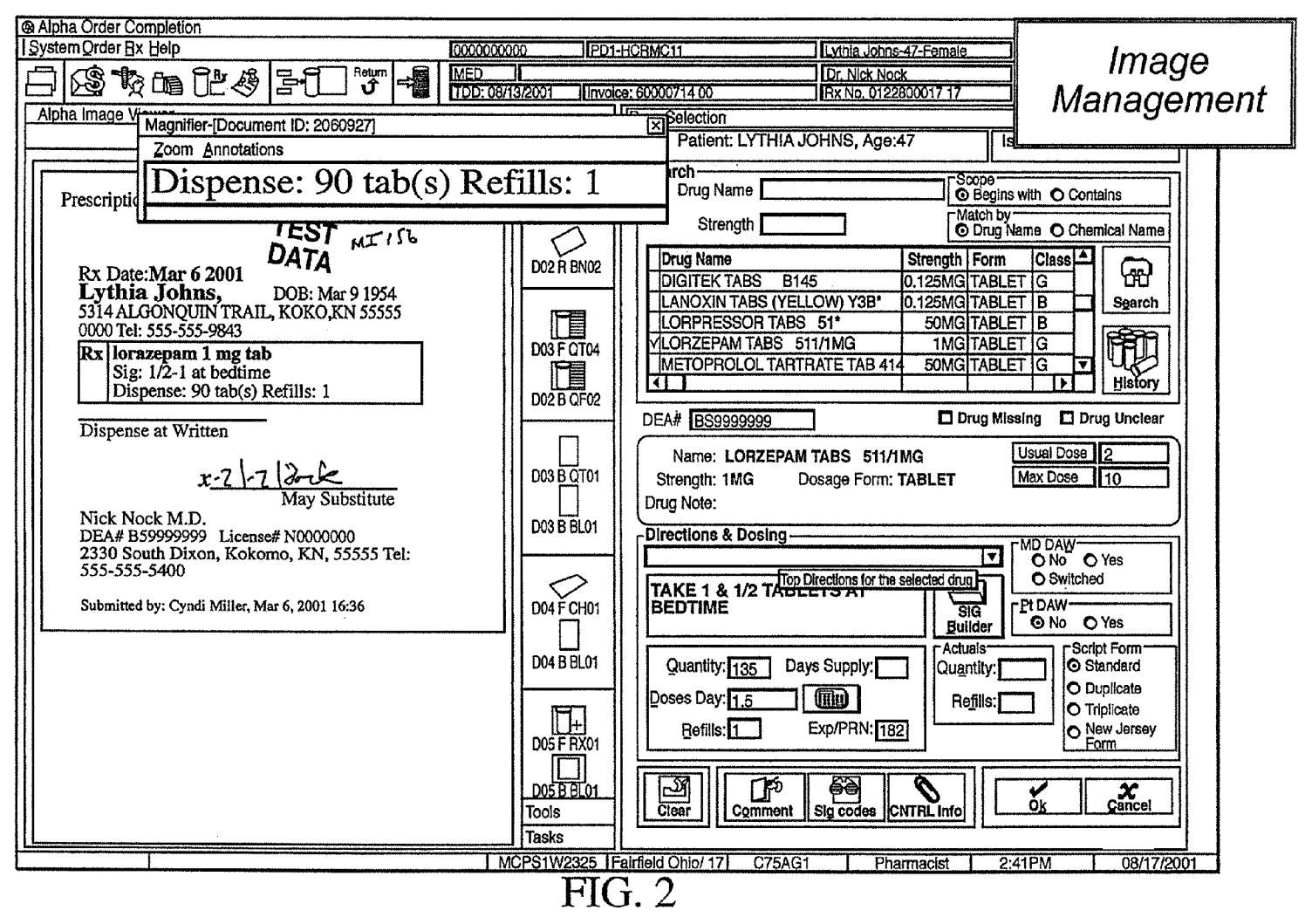

FIG. 2 illustrates a screen capture of an imaged order document captured by the present invention. Once captured the imaged order documents can be manipulated in a number of ways including, for example, enlarging or zooming in on selected portions of an imaged order document; and viewing both the front and back of an imaged order document simultaneously, wherein the two sides appear in separate regions of the image display. Moreover, the imaged order documents can receive annotations directly. The imaged order documents can be updated directly to reflect discussions with a prescriber, such as for example, prescription clarifications and utilization review discussions. The imaged order documents as directly annotated becomes the legal prescription.

Order Processing Flow Control

Figure 3:
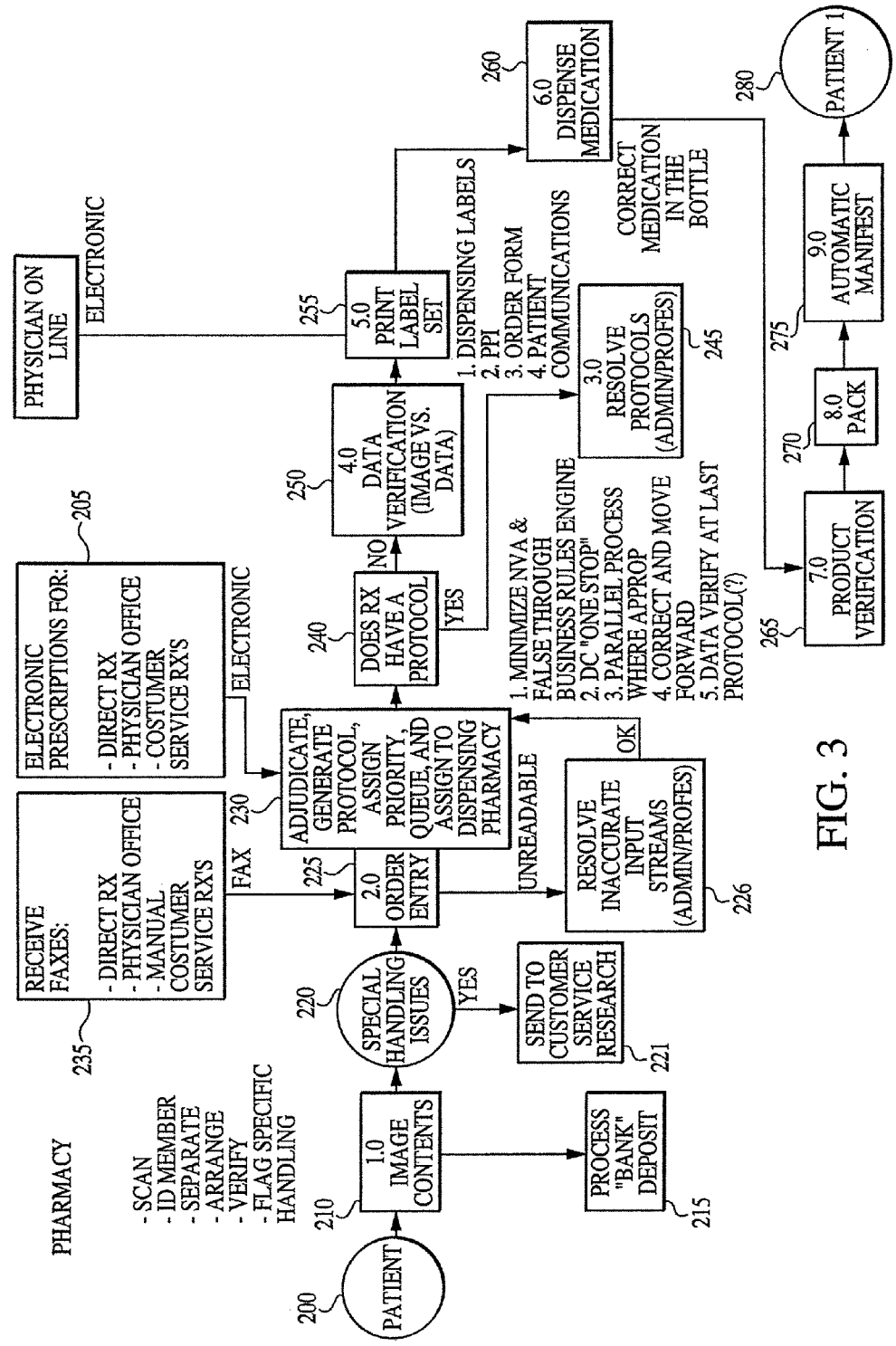
FIG. 3 is a high level block diagram illustrating the overall flow control of an embodiment of the order processing system of the present invention.

FIG. 3 is a high level control flow diagram illustrating an example of the overall flow of an order through the order processing method of the present invention. A patient submits an order in a non-electronic format (e.g., paper) or in an electronic format (e.g., paperless) at 200 and 205, respectfully. The contents of the non-electronic format order are, for example, prepared for imaging and imaged at 210. Payments received with an order are processed and routed to a deposit account at 215. The contents of an order that cannot be imaged or require special processing to be imaged at 220 are optionally routed to a special handling area at 221. The system receives the order images and based on the order images the order is entered into the system by completing at least one data field corresponding to the order at 225. According to an alternative embodiment of the present invention, orders entering the system at step 205 are processed without proceeding through step 225. According to this embodiment, orders not requiring step 225 include, for example, prescription refills submitted from IVRU, the World Wide Web, the Internet, and other electronic communication channels.

Orders or order related information received through the fax communication channel at 235 are entered at 225. If it is determined that during the step of order completion at 225 that an order image is unreadable or otherwise unresolvable, the order is sent to a work queue at 226 to resolve the image.

Facsimile orders and follow up order information received at 205 are captured by a fax server and copied to an image repository and routed to at least one work queue for processing.

Once the order documents are imaged and received by the system the order images are assigned to at least one work queue at 230. The placement of an order in work queues is determined, at least in part, for example, by (i) what operation (s) has to be applied to the order to progress the order from at least one initial queue to an order shipping queue; (ii) the priority of the order, wherein the priority is assigned by the user or the system; and (iii) the order's targeted delivery date, which is based in part, for example, on the date the order was received, the client, and the communication channel that the order was received from. The method applies, as generated at 230 and determined at 240, all applicable protocols necessary to resolve an order and progress an order from at least one initial queue to an order shipping queue. The entered order is then reviewed at 250 against the imaged order.

Upon verification of the entered order against the imaged order the method locks the prescription data from receiving further updates and prints a label set at 255 corresponding to the order. By locking the prescription data from receiving further updates from this point forward establishes user accountability for the interpretation of the prescription data. The label set is printed, for example, in a traditional label printing fashion where the labels are printed first and then filled or an electronic data stream is sent to an automated dispensing pharmacy. See for example U.S. Pat. No. 5,771,657 entitled "AUTOMATIC PRESCRIPTION FILLING, SORTING AND PACKAGING SYSTEM," incorporated herein by reference. The label set includes, for example, the actual prescription label and any other order related patient communications. The order is dispensed at 260 followed by a verification step at 265 to determine the whether the correct medication was dispensed. The verification step at 265 is followed by a packing step at 270 and the automatic generation of a manifest at 275 and then the actual shipping at 280 of the order to the patient.

According to one embodiment of the present invention, before an order can be locked and dispensed all protocols need to be resolved. Once all the protocols are resolved a set of routing logic rules determines which pharmacy or pharmacies will dispense the prescription. The routing logic rules consider, for example, the client benefit plan; contractual service levels; and the type of medication being dispensed, such as whether it is a controlled medication or whether it is temperature sensitive and requires special shipping precautions.

According to another embodiment of the present invention, the order in which an order is dispensed depends on the order's assigned priority number. The priority number can be assigned, for example, based on client contractual service guarantees, wherein orders associated with client service guarantees have a higher priority than those that are not and are therefore dispensed first.

Figure 4:
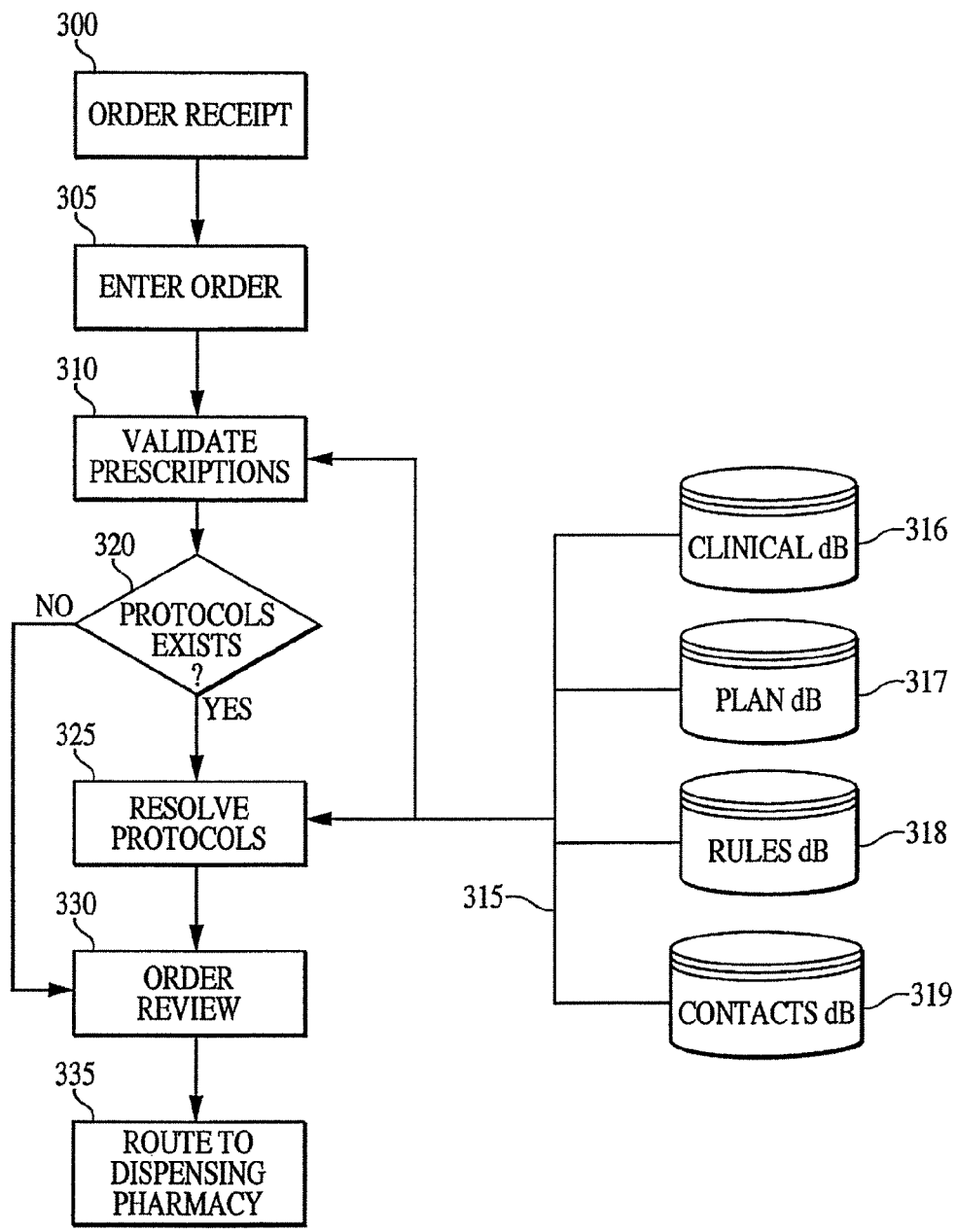
FIG. 4 depicts a high level flow diagram for the processing of an order.

FIG. 4 represents a high level illustration of the overall flow control of the method of the present invention independent of the communication channel from which an order is received. At 300 the order is received and then entered at 305 into the system. Prescriptions contained in an order are validated at 310. The validation step receives input from at least one database at 315. Examples of databases involved in the validation step include, for example, a clinical database 316, a benefits plan database 317, a rules database 318, and/or a contacts database 319. According to an alternative embodiment of the present invention examples of databases involved in the validation step include a clinical database, a plan database, a rules database, a contacts database, an accounts receivable database, a formulary database, a pricing database, a client profile database, a patient history database, and combinations thereof.

Upon validation of the prescriptions the method checks at 320 for the existence of any applicable protocols to the order. If any protocols apply, the applicable protocols are resolved against at least one database at 325. Examples of databases involved in the resolution step include, for example, a clinical database 316, a benefits plan database 317, a rules database 318, and/or a contacts database 319. According to an alternative embodiment of the present invention examples of databases involved in the protocol resolution step include a clinical database, a plan database, a rules database, a contacts database, an accounts receivable database, a formulary database, a pricing database, a client profile database, a patient history database, and combinations thereof.

[Table 1] FIGS. 24 to 53 includes examples of some of the protocols the present invention is capable of resolving.

Upon the resolution of all applicable protocols at 325, the order is reviewed at 330 to determine whether each order element is correct. Correct orders are routed at 335 to a dispensing pharmacy queue. According to an overlapping embodiment of the present invention, a dispensing pharmacy queue can be located in a geographically different location from where the steps of order entry, validate prescription, resolve protocol and order review are completed. According to an overlapping embodiment of the present invention, each of the steps of order entry, validate prescription, resolve protocol, order review, and routing to dispensing queue can each be performed in geographically distinct locations from each other.

Figure 5:
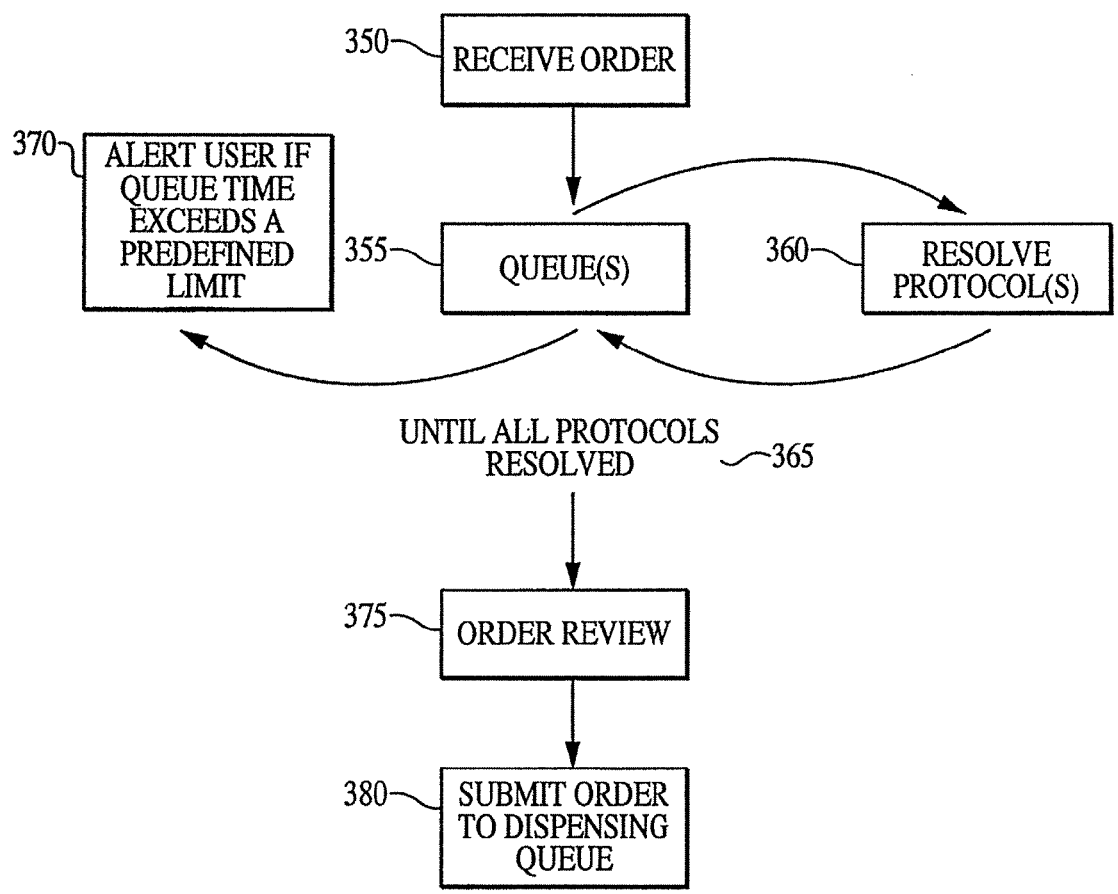
FIG. 5 depicts a flow diagram illustrating the iterative application and resolution of an order.

FIG. 5 illustrates the iterative process involved in resolving protocols that apply to an order. The order is received at 350, and assigned to at least one initial queue at 355. The order progresses to a dispensing pharmacy queue through at least one intermediate queue, wherein for each queue the order populates the method determines at 360 what, if any, protocols apply to an order. The method continues this process until all applicable protocols are resolved at 365. The method also provides a positive control mechanism that prevents an order from being lost or fixed in any single queue due to an inability to resolve a protocol. The method sends an alert at 370 when an order remains in any one queue beyond a predetermined period of time. Upon the resolution of all applicable protocols at 365, the order is reviewed to check to see that all order elements are correct and, if correct, then routed at 380 to a dispensing pharmacy queue.

Header Entry

Figure 6:
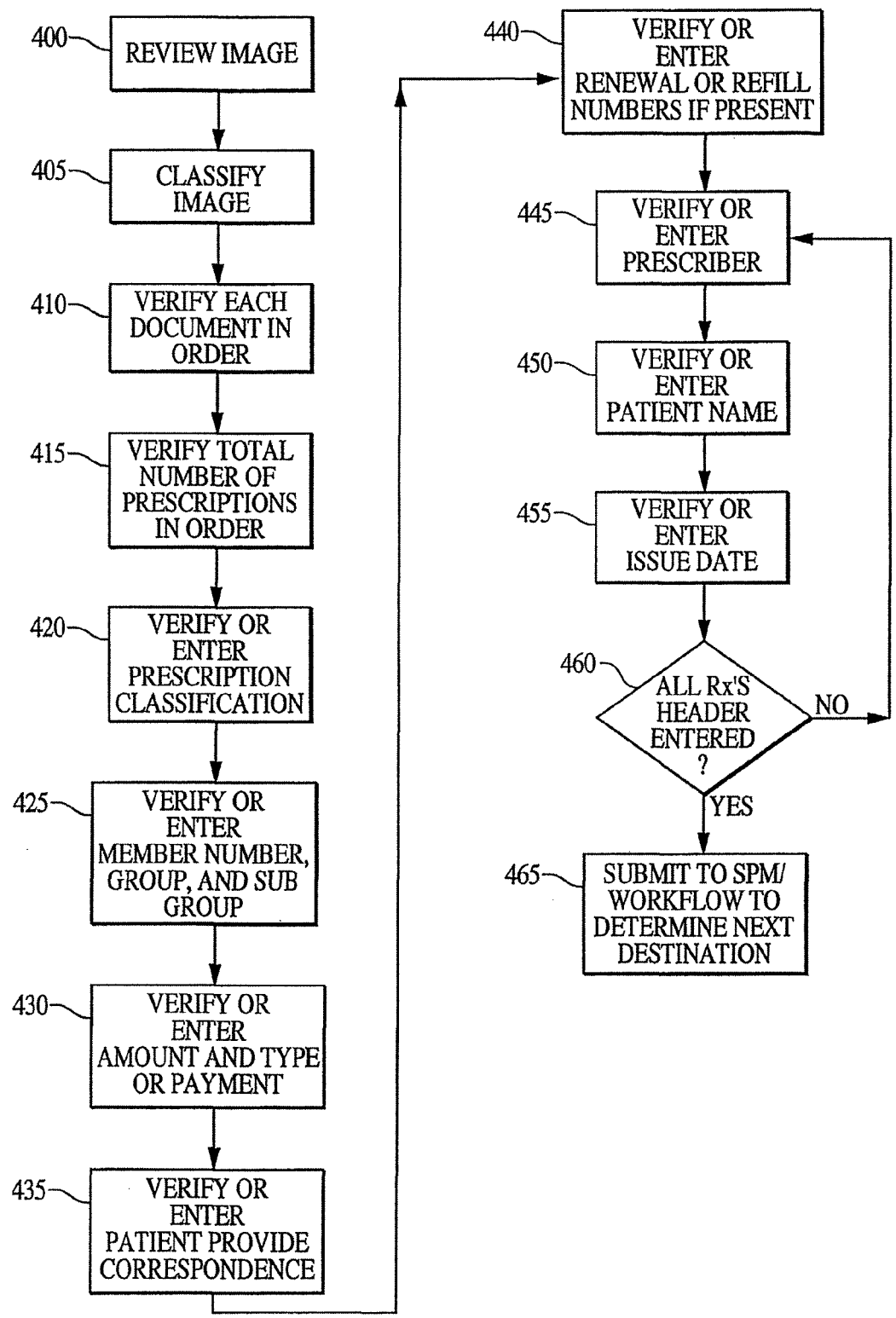
FIG. 6 depicts a flow control diagram for Header Entry.
Figure 8:
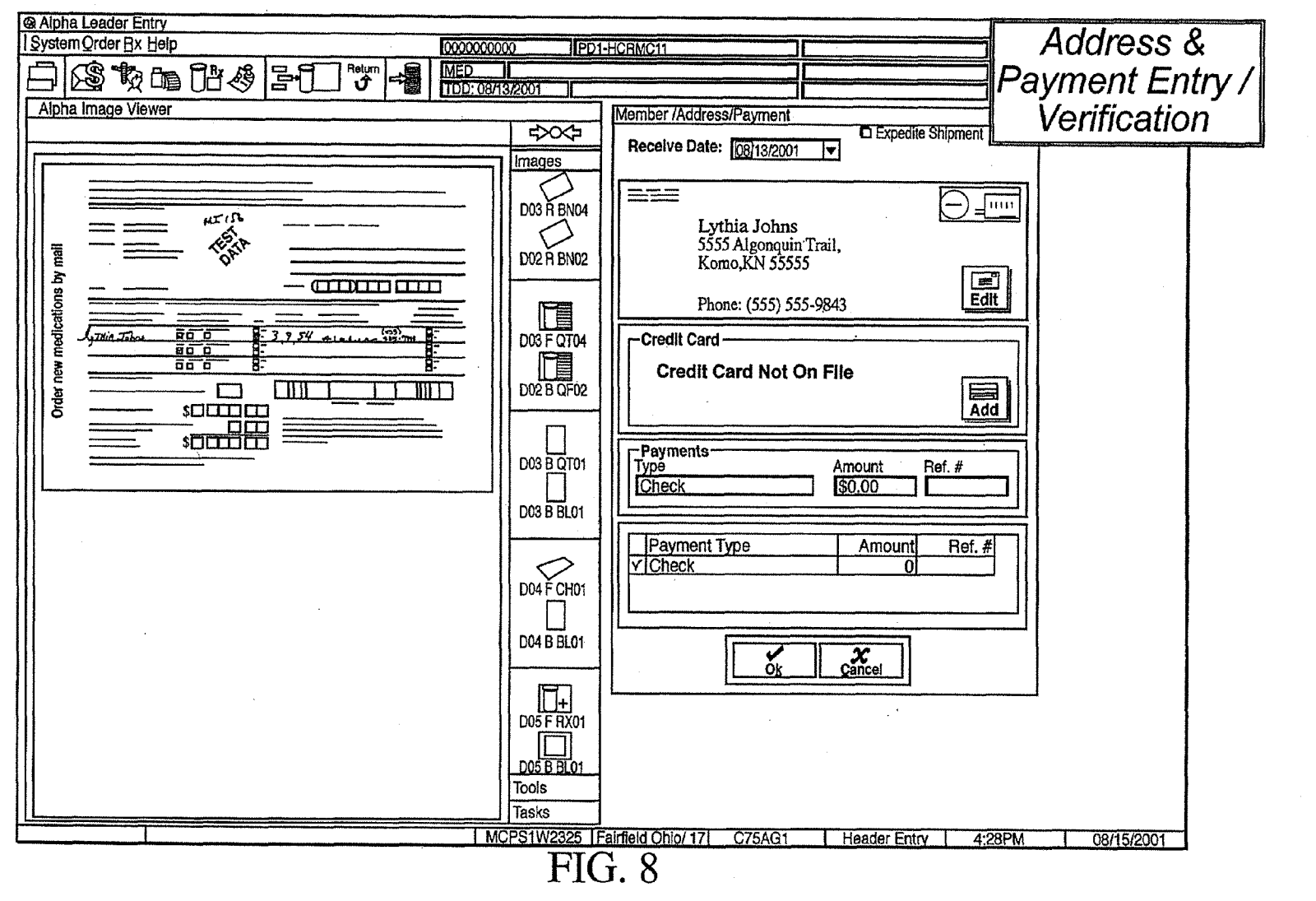

FIG. 6 depicts an example of flow control for Header Entry. Header Entry provides the steps for entering the non-clinical data in order fields that relate to an order. The data verified and/or entered in the Header Entry process is derived generally from the imaged order documents or other electronic and/or non-electronic order documents. The verification and/or entry process involves a review at 400 of the imaged order documents or other captured data to check against a data field or to enter data in a required but currently empty data field. FIG. 8 illustrates a screen capture of an embodiment of the present invention, wherein an imaged order document is juxtaposed to the member, address, and payment data entry fields. Examples of data that is entered in the header and/or verified include, for example, patient name, prescriber name, shipping address, payment amount, and/or credit card number. Each order image is reviewed at 400 followed by image classification at 405. Each document contained in an order is verified and accounted for at 410. The total number of prescriptions present in an order is verified at 415. Each prescription is reviewed at 420 to ensure that it has been assigned to the correct prescription classification. If no prescription classification is present, one is entered at 420. The order is checked to verify at 425 that it has been assigned the correct benefit's plan member number, group number and sub-group number. If no benefit's plan numbers are present or only a subset of the numbers is present the numbers are entered at 425. The amount and type of payment is verified at 430. If no payment amount and type has been provided an amount and type of payment is entered at 430. Patient provided correspondence is verified at 435. If no patient correspondence has been entered, patient provided correspondence is entered at 435. According to an alternative embodiment of the present invention, if no patient correspondence is provided the process continues to step 440 with the patient correspondence field(s) blank.

The number of times a prescription is to be renewed or refilled is verified at 440. If renewal or refill numbers have not been entered, but a renewal or refill number is present in the order, then a renewal or refill number is entered at 440. The prescriber name is verified at 445. If no prescriber name has been entered than the prescriber name is entered at 445. In an alternative embodiment of the present invention, the step of at least one of verifying or entering a prescriber name additionally includes at least one of, selecting a prescriber from a history list which matches patients to their prescribers; selecting a prescriber from a prescriber database; entering a new prescriber; or editing existing prescriber information. The patient name is verified at 450. If no patient name has been entered than the patient name is entered at 450. The prescription issue date of each prescription is verified at 445. If no prescription issue date has been entered, than the issue date is entered at 455. Upon the verification and/or entry of all or a predetermined set of Header Entry data at 460 the order is submitted at 465 to a workflow queue to determine the order's next destination.

Preprocessing Flow Control for Mail Orders

Figure 7A:
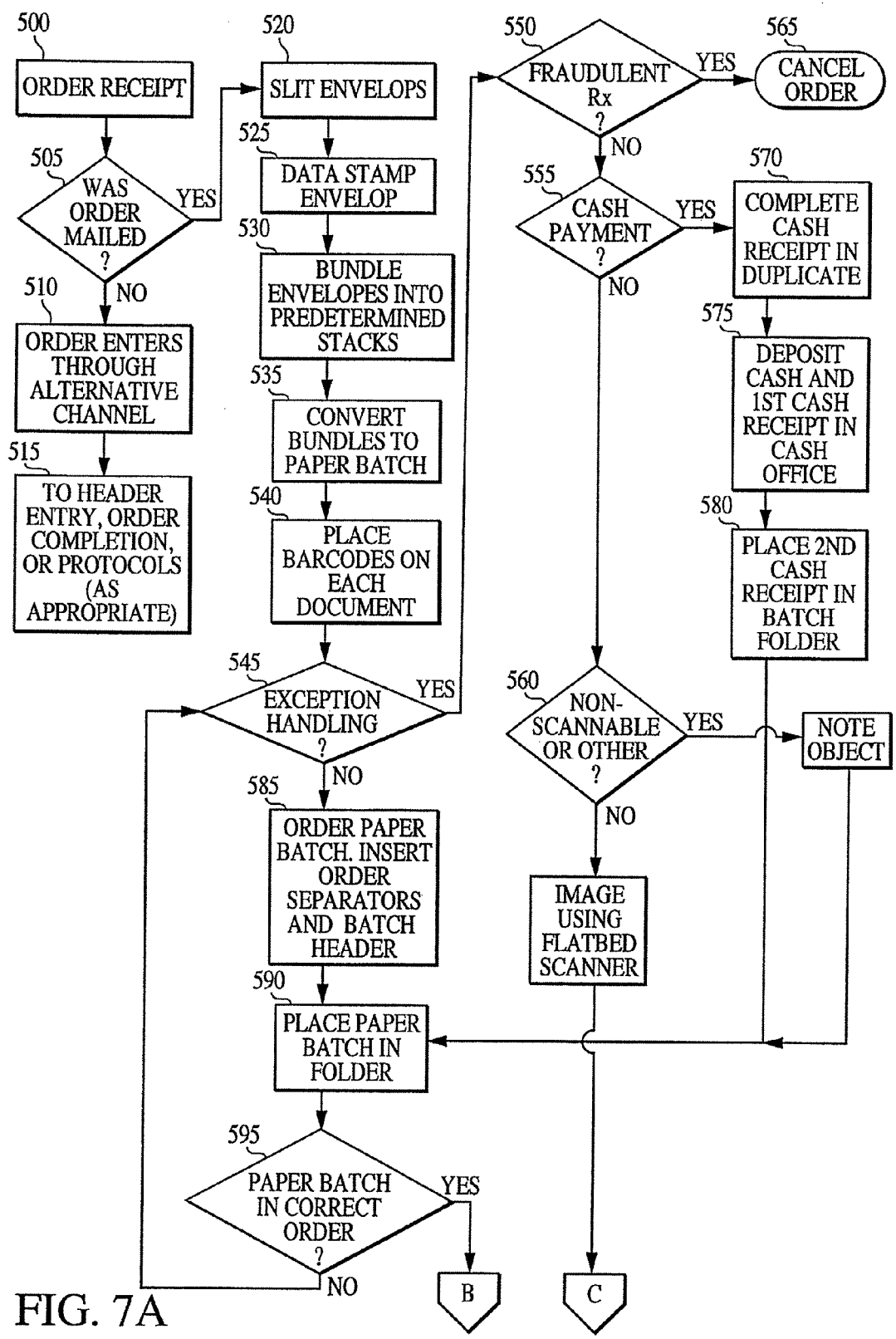
FIGS. 7A and 7B depict a flow control diagram for preprocessing an order received in the mail communication channel.
Figure 7B:
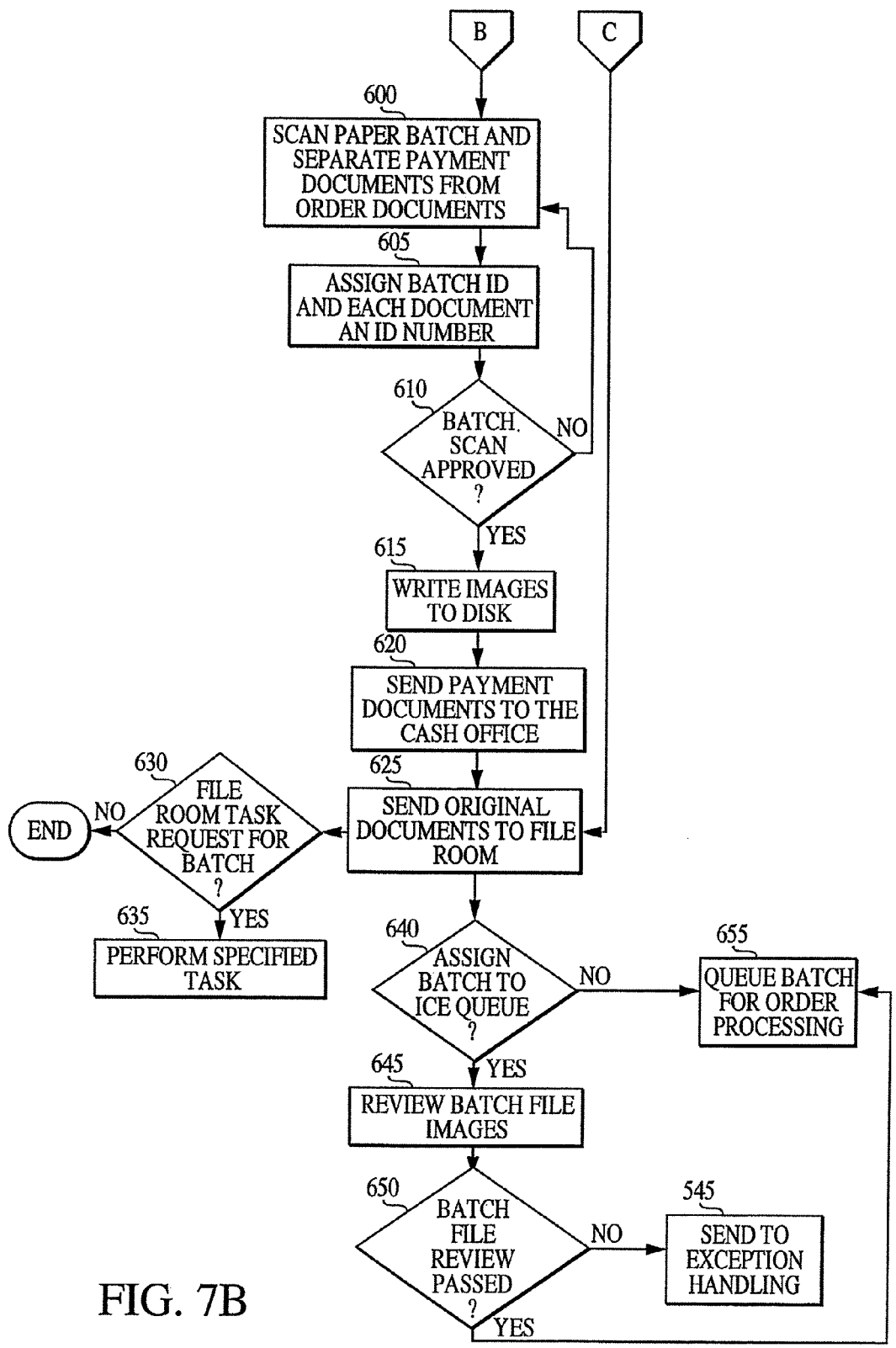

FIGS. 7A and 7B illustrate an example of the flow control of order preprocessing when an order is sent by mail. Orders are received at 500. If the received order is not a mail order 505, the order enters the system through one of other system communication channels at 510 and is routed to Header Entry, Order Completion or protocols as appropriate. Mailed orders are aggregated with other received mail orders. The envelopes in which the orders are contained are slit at 520 and date stamped at 525. The slit envelopes are bundled at 530 in stacks of predetermined size. Each bundle is then converted at 535 to a paper batch. Barcodes are placed on all applicable documents within a paper batch at 540. Every document in a paper batch is not necessarily eligible to receive a barcode. Document eligibility for receiving a barcode is based on predetermined criteria.

If a document within a paper batch fails at 545 to meet predetermined criteria, that document is sent to an optional exception handling area to determine whether the document is, for example, a fraudulent prescription at 550, a cash payment at 555, non-scannable at 560 or otherwise unreadable. If the order is determined to be fraudulent at 550 the order is cancelled at 560. If the order is a cash payment a cash receipt is completed in duplicate at 570 and the cash payment along with one of the duplicate cash receipts is placed in a deposit account at 575. The other duplicate cash receipt is returned at 580. to its corresponding order documents. If the order is nonscannable, a document representing the nonscannable document or the information contained therein is created, scanned and returned to its corresponding order documents. Exception handling documents that can be scanned are scanned at 586 using a flatbed scanner.

Documents in a paper batch that meet predetermined criteria are ordered at 585 by placing a Batch Header atop the paper batch, order separators between each order, and a Batch End at the end of the paper batch. The ordered paper batch is placed in an, for example, accordion folder at 590 and reviewed for organizational correctness at 595. Upon a successful review of the paper batch the paper batch is scanned at 600 and the payment documents are separated at 600 from the order documents. If the paper batch is not found to be in correct order at 595 the paper batch is routed to exception handling at 545 for reordering.

The scanning process attaches a paper batch identification number at 605 to each paper batch as well as a document identification number at 605 to each document image in a paper batch. According to an alternative embodiment of the present invention, the document identification number includes the Julian date and a unique identification number.

The scanning processor preferably captures the images of the order documents in color and images both sides of each order document simultaneously.

The scanned images captured from the paper batch are reviewed according to a predetermined review schedule. If upon review, the captured images are approved at 610 the images are written to disk at 615 or other computer storage medium. Also, upon approval of the images, the payments which were separated out at 600, are sent to a deposit account at 620. However, if the images once reviewed according to the predetermined review schedule are not approved the paper batch is rescanned at 600.

After approval at 610 of the scanned images the paper batch used to create the scanned images is archived at 625. The paper batch is archived at 625 in a predetermined manner that indexes it to the scanned images and, as such, is always retrievable during the processing of the order based on the scanned images. If the paper batch needs to be accessed during the processing of the order based on the scanned images, a task request at 630 can be submitted and the requested task performed at 635 on the paper batch.

The entire set of scanned images that correspond to all the documents in a paper batch are reviewed at 640 for quality control purposes based on a predetermined review schedule. According to one alternative embodiment of the present invention, the predetermined review schedule is based on the random selection of recently completed scanned paper batches. If a paper batch is selected for review at 645 each image in the batch is optionally reviewed. If the paper batch passes the review at 650 it is queued in at least one system work queue at 655 for further order processing. Paper batches that fail to pass the review at 650 are sent to exception handling at 545. Batches not selected for review are queued directly in at least one system work queue for further order processing.

Order Completion

Figure 9:
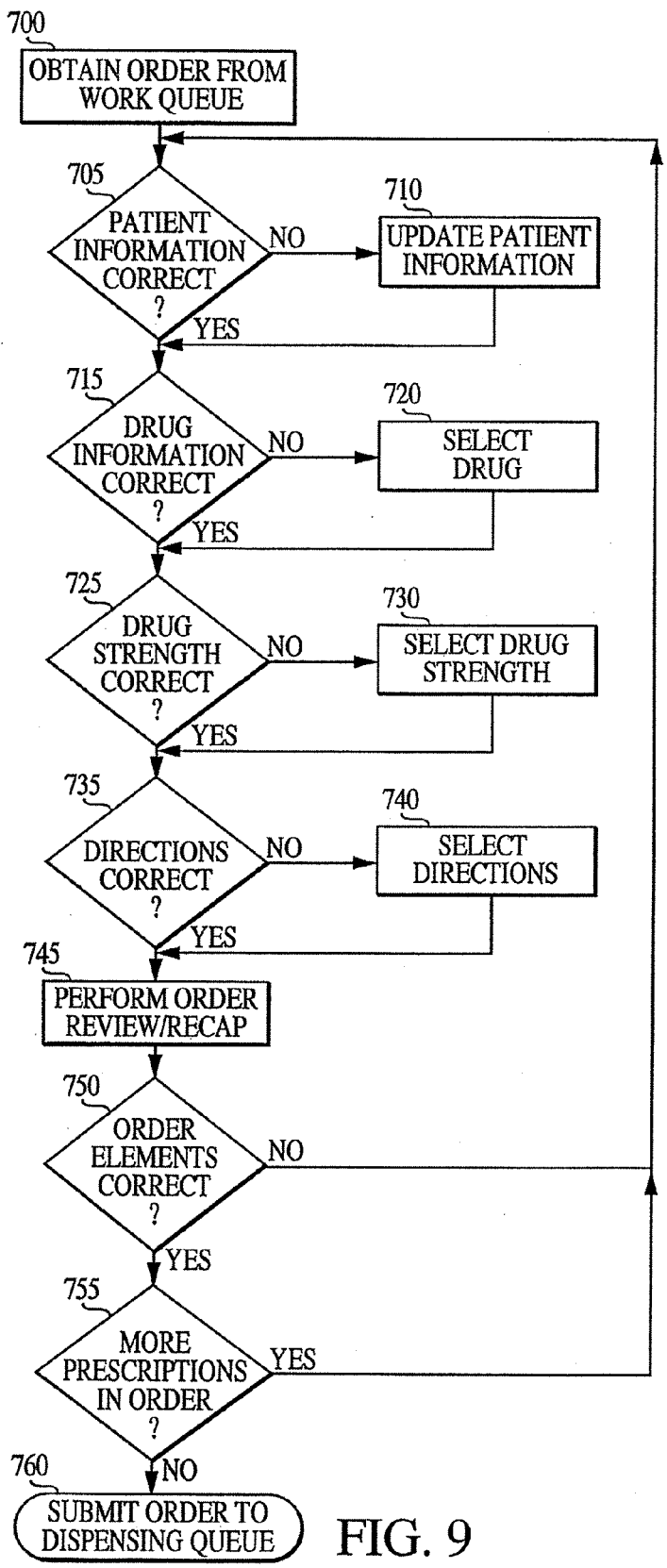
FIG. 9 depicts a flow control diagram for Order Completion.
Figure 12:
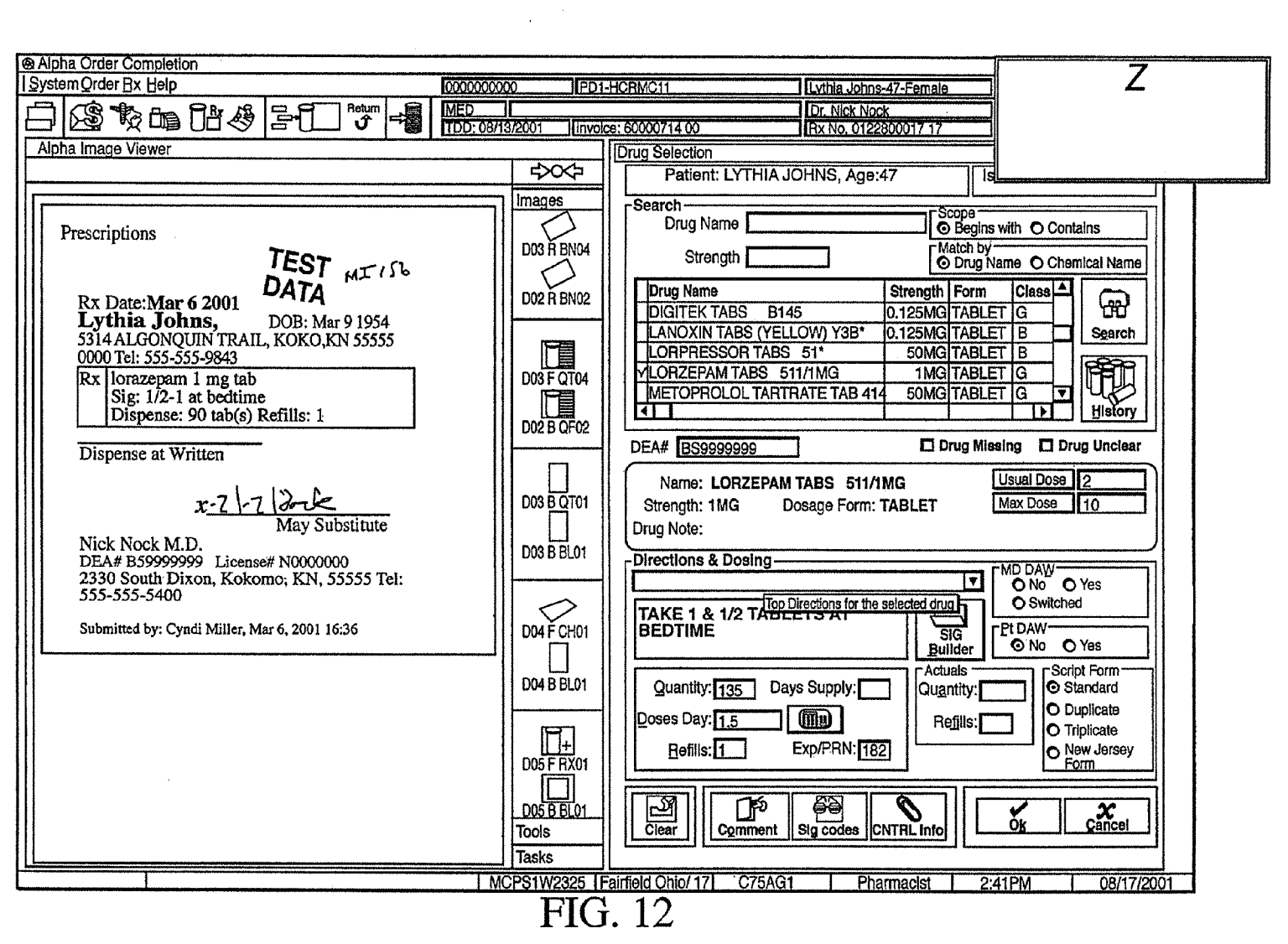

FIG. 9 depicts an example of the general steps involved in Order Completion. The Order Completion steps involve the verification and/or entry of clinical data. The verification and/or entry process involves, in part, reviewing the imaged order documents or other captured data to check against a data field or to enter data. FIG. 12 illustrates a screen capture of an embodiment of the present invention, wherein the imaged prescription order document is juxtaposed to drug selection data entry fields. An order is obtained from a work queue at 700. A determination is made at 705 as to whether the patient information is correct. If the patient information is incorrect, the patient information is updated at 710 accordingly. Next drug information is reviewed at 715 to determine its correctness. If the drug information is incorrect, the correct drug is selected and the order is updated at 720 accordingly. Next the drug indicated strength is reviewed at 725. If the strength is incorrect, the correct drug strength is selected at 730. A determination is made then at 735 as to whether the directions for drug usage are correct. If the directions are incorrect, the correct directions are selected at 740. Corrections to any incorrect entry can be made by manually typing in the corresponding correct information or by selection of the correct information from pull down menus. Further, the above outlined steps do not have to be practiced in the order described above. According to an alternative embodiment of the present invention step 715, and corresponding step 720, are interchanged with step 735 and corresponding step 740.

Once all the clinical data is verified and/or entered, the order for that particular prescription is reviewed at 745 to ensure every order element at 750, as it relates to a single prescription, is correct. If a particular prescription's order elements are not correct then steps 705 through 735 are repeated until correct. If all the order elements for a particular prescription are correct, the order is checked for additional prescriptions at 755. If additional prescriptions are present in the same order, steps 705 through 750 are repeated until all the prescriptions in a single order are resolved. Upon completion of all the prescriptions in an order and/or all the order elements being found correct, the order is submitted to a dispensing pharmacy queue at 760. According to an alternative embodiment of the present invention, an order containing multiple prescriptions does not need to have all prescriptions in the order processed before releasing the individual prescriptions to the dispensing pharmacy queue at 760.

Moreover, and according to an alternative embodiment of the present invention, each step in the order completion process is supported by a set of tools that aid the user in the completion of order completion process. These tools include, for example, a drug usage direction builder that allows the user to build the drug usage directions by selecting from at least one pull down menu phrases and/or words; a spelling checker, and drug lookalike/sound-a-like functionality.

Protocols

Protocols are a set or aggregation of sets of rules that act to resolve elements of an order. Resolution of one protocol may give rise to the need to resolve additional protocols. For example, if an element from an order is missing or is unclear, protocols are used to not the missing or unclear element and to track the resolution of the element. Tracking includes, for example, noting which user performed the verification and who was contacted to resolve the element.

According to one embodiment of the present invention, the method and system of the present invention provides a set of wizards and tools that aid a user in resolving protocols. The wizards walk a user through a protocol or process in a step-by-step manner an show how to resolve a particular protocol. The wizards walk through the resolution of a protocol by providing a series of system prompts. The tools include, for example, Add Protocols, which allows a user to add a protocol to an order; Suspend Order, which allows a user to suspend the processing of an order temporarily; Stop/Cancel Prescription, which allows for the cancellation of a prescription within an order while still permitting the other prescriptions in an order to proceed; Stop/Cancel Order, which allows a user to completely cancel an entire order; Pull Prescription and Insert, which allows a user to flag an order when a drug loses patent protection so that at refill time the generic brands are available for the refill; New Prescription Copy, which allows an order or prescription to be copied into a new invoice; and Order Review, which allows instantaneous order review.

Contact Management

Figure 10:
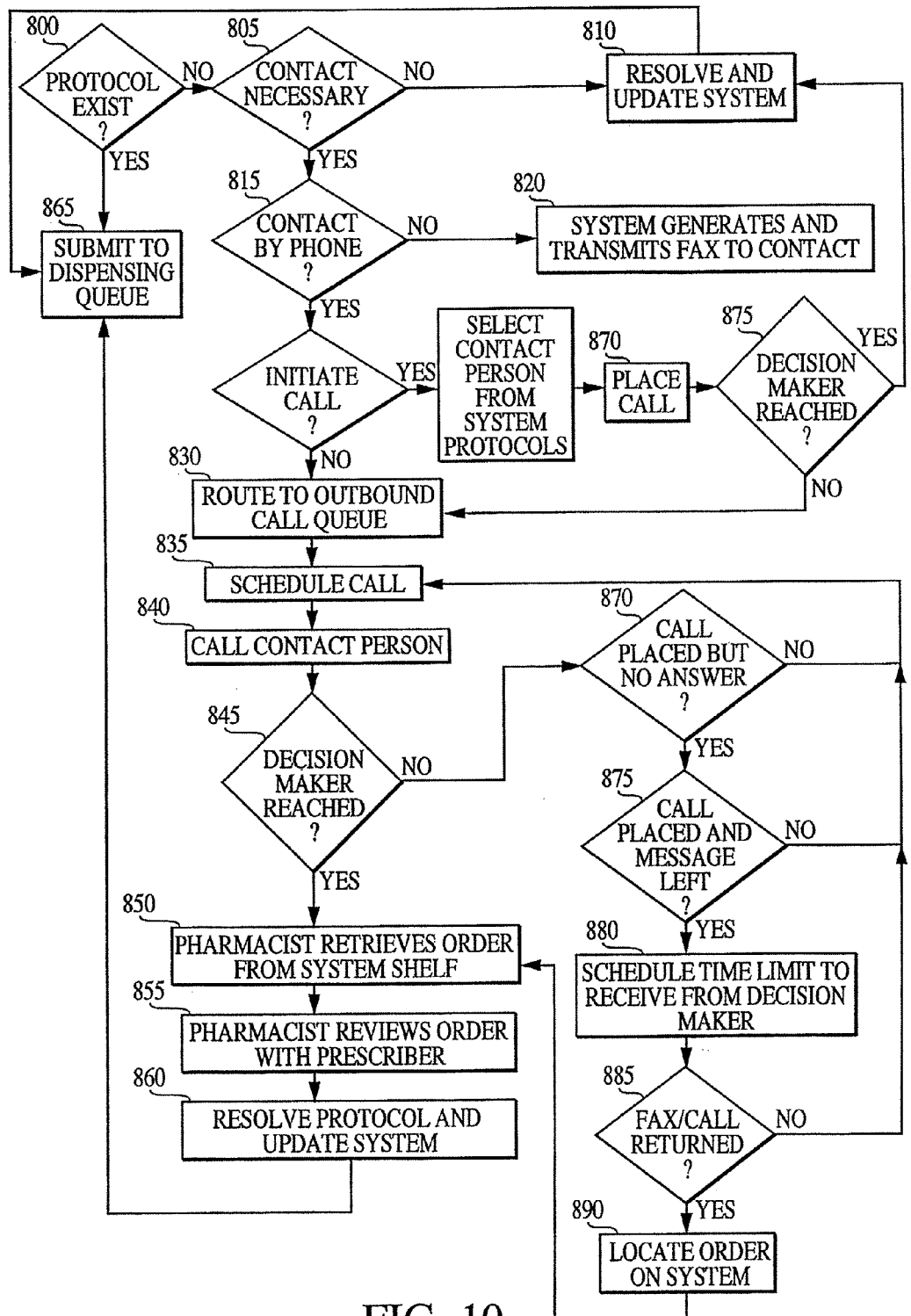
FIG. 10 depicts a flow control diagram for Contact Management.

FIG. 10 depicts an example of the general flow control for Contact Management. A determination is made at 800 as to whether any applicable protocols apply. If a protocol applies, a determination is made at 805 as whether the protocol can be resolved without contacting a prescriber. If no contact is necessary, the protocol is resolved at 810 and submitted at 810 to a work queue for further processing. If a contact is required to resolve a protocol, a determination is made at 815 as to whether an outbound facsimile to the prescriber will resolve the protocol or whether a phone call to the prescriber is required. For protocols that can be optionally resolved by an outbound facsimile, a facsimile is optionally generated at 820 with the appropriate fields necessary to resolve the protocol populated and once populated the facsimile is transmitted at 820 to the prescriber. According to an alternative embodiment of the present invention, transmission of the fax initiates the running of a wait queue that measures the length of time from fax transmission to returned contact from prescriber. If the measured time exceeds a predetermined value before return contact by the prescriber is initiated, the order is placed in an outbound call queue.

If a phone call is required to resolve a protocol the contact request is routed at 830 to an outbound call queue, and a call is scheduled at 835. A phone call is placed at 840 to the prescriber at the scheduled time if the prescriber is reached at 845, the user placing the call retrieves the order at 850 with the protocol to be resolved from a virtual shelf. The user then reviews at 855 the order with the prescriber soliciting the necessary information from the prescriber to resolve the protocol. Once the protocol is resolved at 860, the order is placed in a work queue at 865 for further processing.

Alternatively, if a phone call is placed but the user received at 870 no answer, the order returns to the outbound call queue and another call is scheduled at 835—repeating steps 835 through 845. If a phone call is placed and a message is left at 875 for the prescriber, the outbound call queue is updated to reflect that a message was left for the prescriber and a predetermined period is set at 880 in which a call or other communication from a prescriber is to be received. If the predetermined period lapses before a return call is made at 885 another call is scheduled.

A phone call returned or fax returned at 885 from a prescriber launches a hunt routine at 890 to locate the order on the system. If a call back is received from the prescriber within the predetermined time, the order is located on the system at 890 and the call is transferred at 850 to a user on the system who retrieves the order at 850 from a virtual shelf. The user then reviews at 855 the order with the prescriber soliciting the necessary information from the prescriber to resolve the protocol. Once the protocol is resolved at 860 the order is placed in a work queue for further processing at 865.

If a facsimile is received from the prescriber at 885, the facsimile is linked to the order and a user reviews the information contained in the facsimile to resolve the protocol. Upon resolution of the protocol the order is placed in a work queue for further processing.

Alternatively, a call can be placed to the contact without proceeding through the outbound call queue step. Instead of routing the order to the outbound call queue, a user simply selects at 870 the contact and initiates at 875 the call to the selected contact. If the contact is reached at 880 the user reviews the order with the contact soliciting the necessary information from the contact to resolve the protocol. Once the protocol is resolved the order is updated and placed in a work queue for further processing. If the contact is not reached the order is routed to the outbound call queue.

Fax Contact Management

Figure 11:
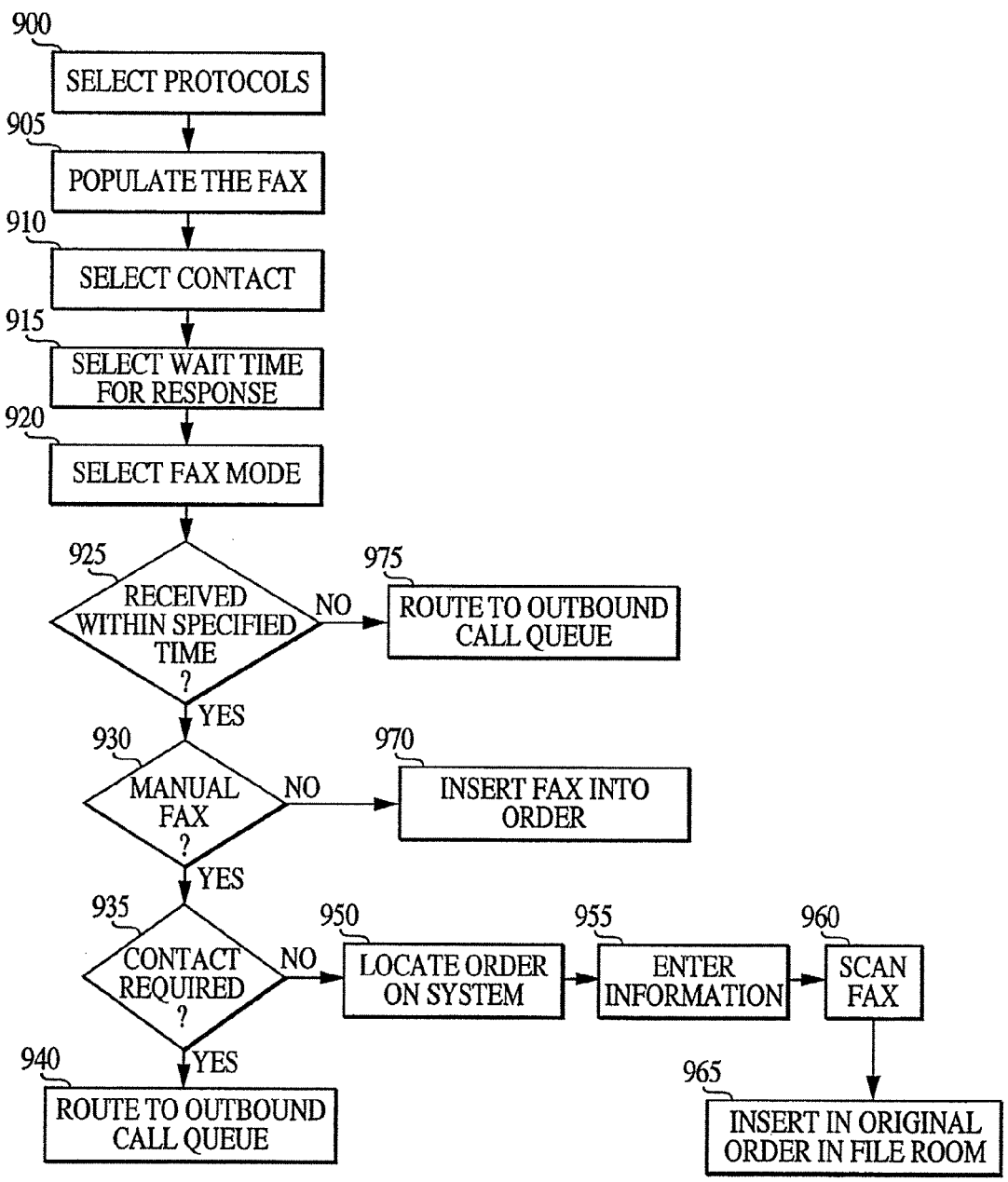
FIG. 11 depicts a flow control diagram for Fax Process.

FIG. 11 illustrates an example of the flow control for Fax Contact Management. The protocols to be resolved are selected at 900. The fields necessary to resolve the protocol(s) are populated at 905 within the facsimile. The contact person is selected at 910. The time in which to receive a response before further action is taken is selected at 915. A determination as to whether to send a manual facsimile or a system generated electronic facsimile is made at 920. If a response is received within the selected time at 925 from the contact person, the order is updated according to the information contained in the facsimile. The process by which the received facsimile becomes part of the order differs depending on the mode in which the facsimile is received. If the facsimile is a manual or paper fax 930, the order is located on the system at 950 and the information in the facsimile is entered at 955. The manual or paper facsimile is then scanned at 960 and inserted at 965 into at least one of the imaged order documents or the order documents in the archived paper batch. Alternatively, the scanned image is inserted in the imaged order documents and the archived paper batch. If the facsimile is electronic or otherwise generated from one fax processing system to another, the order is updated based on the information contained in the facsimile and the received facsimile becomes at 970 part of the imaged order documents.

If an inbound facsimile, manual or electronic, is not received within the time selected, the order is routed at 975 to the outbound call queue and steps 830 through 845 in FIG. 10 are followed. If an outbound fax is received for a contact but the order requires an actual contact with the contact, the order is routed at 940 to the outbound call queue.

FIG. 13A-13E represent alternative embodiments of FIG. 10 and FIG. 11 illustrating the flow control for Contact Management against the context of specific protocol resolution. During order completion the order is reviewed to determine whether the required prescription elements are present. The required prescription elements represent the key elements of a prescription that must be present and valid to dispense the prescription. If all the required elements are present the order is reviewed. However, if the required elements are not present, the order is submitted to at least one further work queue for additional processing. A determination is then made as to whether only Alpha or "Routers, Counters, and Flags" Protocols remain unresolved. Alpha protocols are created and resolved automatically and exist for each order until the order is ready to be locked in preventing additional order edits and routed to a dispensing pharmacy.

Order completion involves the resolution of any applicable protocols pertaining to an order. If a protocol cannot be resolved by checking it against relational databases, it may require at 1025 contacting the prescriber or someone within the prescriber's office to resolve the protocol. If a prescriber contact is necessary at 1025 to resolve an applicable protocol the order is routed at 1030 to the outbound calling queue. The order is retrieved at 1035 by a system user and a determination is made at 1040 as to whether the protocol can be resolved by faxing the prescriber with the outstanding protocol to be resolved. If the protocol is resolvable by faxing at 1040 the prescriber, a fax is sent at 1045 to the prescriber. Sending the fax to the prescriber creates a time stamp within the system. The time is measured at 1050 from the time stamp against a predetermined value and if the time, as measured from the time stamp, exceeds a predetermined value the fax wait time is timed out, and the order is routed at 1030 to the outbound call queue in which steps 1030 through 1040 are repeated.

If however an inbound fax is received at 1055 within the predetermined value, an automatic match process is initiated at 1060 attempting to match the incoming fax with the order that spawned the original outgoing fax to which the incoming fax is a response. If the order is found at 1065 a system user enters at 1070 the information contained in the incoming fax into the order. The order is then reviewed at 1070 and submitted for resolution processing at 1075. Alternatively, if the order is not found at 1065 through the automatic match process, the order then becomes handled at 1080 through standard operating procedures. Standard operating procedures include, for example, the user reviewing the response received against the current state of the order on the system. If, for example, the order has been cancelled, no further action is taken. If the order has been transmitted to a dispensing pharmacy then the faxed response is compared to the system data to determine that the correct information is processed. If the data on the system is the same as the faxed data then no further action is taken, however, if discrepancies exist than the order is reviewed by a user for further processing and resolution. Responses not received at 1056 within the predetermined value as measured from the transmittal are routed at 1030 to the outbound call queue.

If the inbound fax response is received at 1250 on a fax server, the fax server routes at 1255 the response to a work queue based on the fax response identification. All order objects are retrieved at 1260 from the work queue and the fax response is appended at 1265 to the order. Responses not received at 1056 within the predetermined value as measured from the transmittal are routed at 1030 to the outbound call queue.

If the user determines at 1040 that the protocol is not resolvable by sending a fax to the prescriber, the user initiates a phone call at 1085 by dialing the prescriber at 1090. Upon reaching the dialed number at 1095, the user attempts at 1100 to contact the prescriber or other decision maker. If the prescriber or other decision maker is reached at 1100 the user introduces the protocol to be resolved at 1105 and transfers at 1110 the call to a pharmacist. The call transfer is then followed by or concurrent with the user shelving the order and routing the order at 1115 to the pharmacist. The pharmacist retrieves at 1120 the order from the shelf and reviews at 1125 the intervention with the prescriber and resolves the protocol(s). The order is then submitted at 1130 to a work queue for further processing.

If upon placing the call there is no answer at 1095, a call back slip is completed at 1135 and the call is rescheduled and the outbound call queue is updated at 1140 accordingly. A call back slip is printed at 1145 and the order is routed at 1030 to the outbound call queue. Alternatively, if the call solicits an answer but the prescriber or other decision maker is not available at 1100, a call back slip is completed at 1150 and order identifying information is left at 1150 with the prescriber's office. The outbound call queue is updated at 1140 accordingly. A call back slip is printed at 1145 and the order is routed at 1030 to the outbound call queue.

Figure 13A:
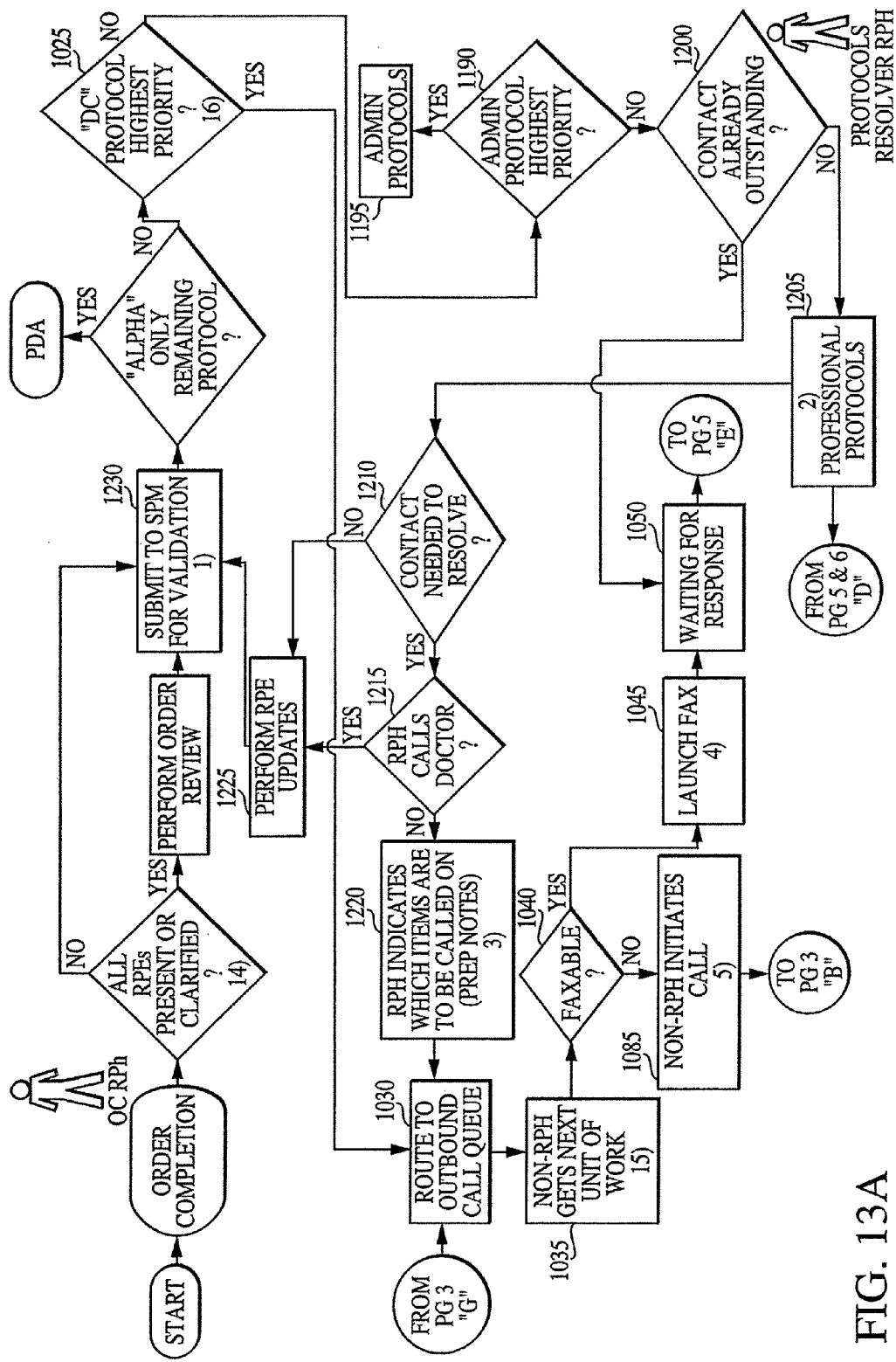
FIG. 13A-13E depicts a flow control diagram of an overlapping embodiment for Contact Management.
Figure 13B:
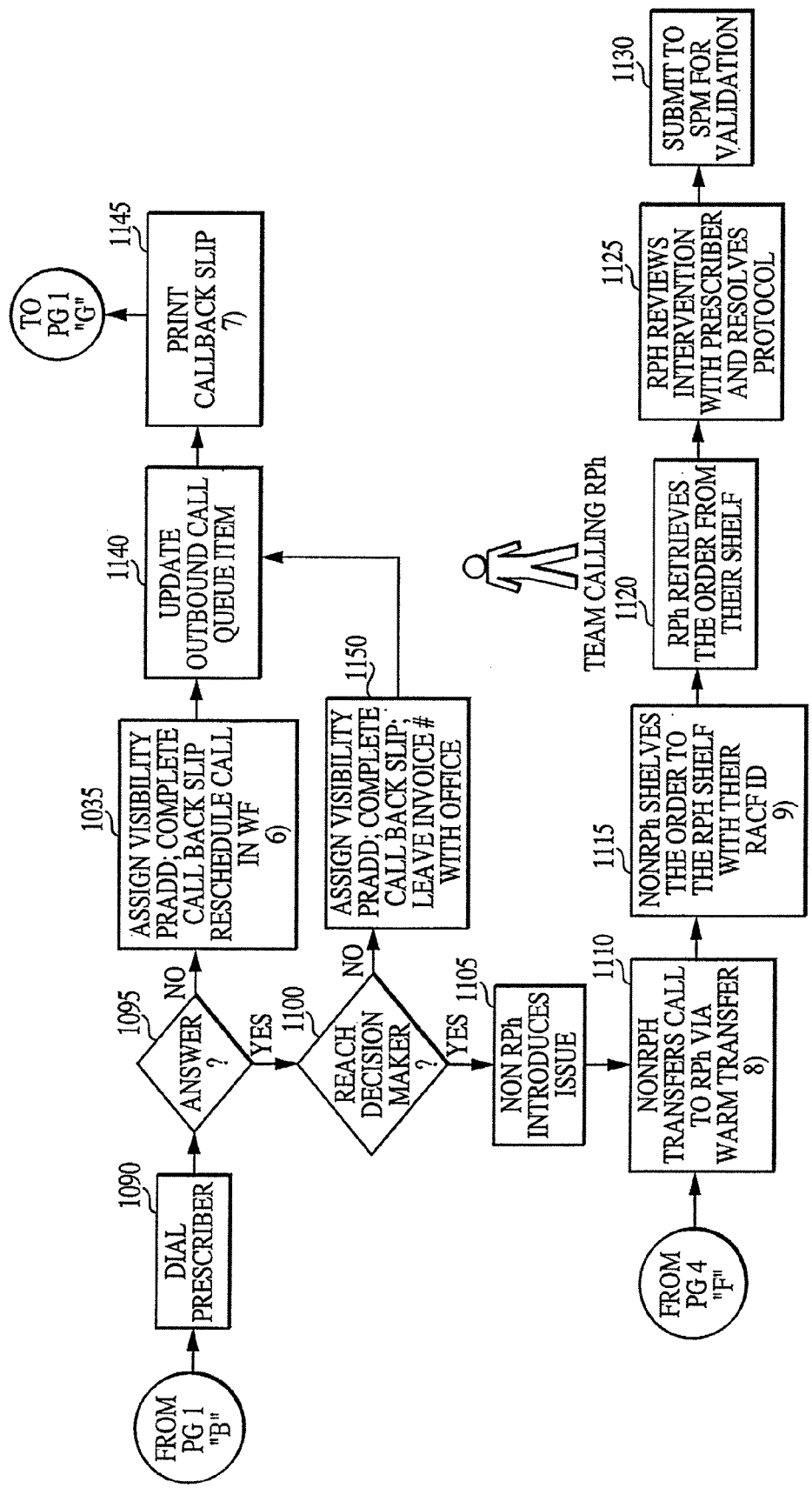
Figure 13C:
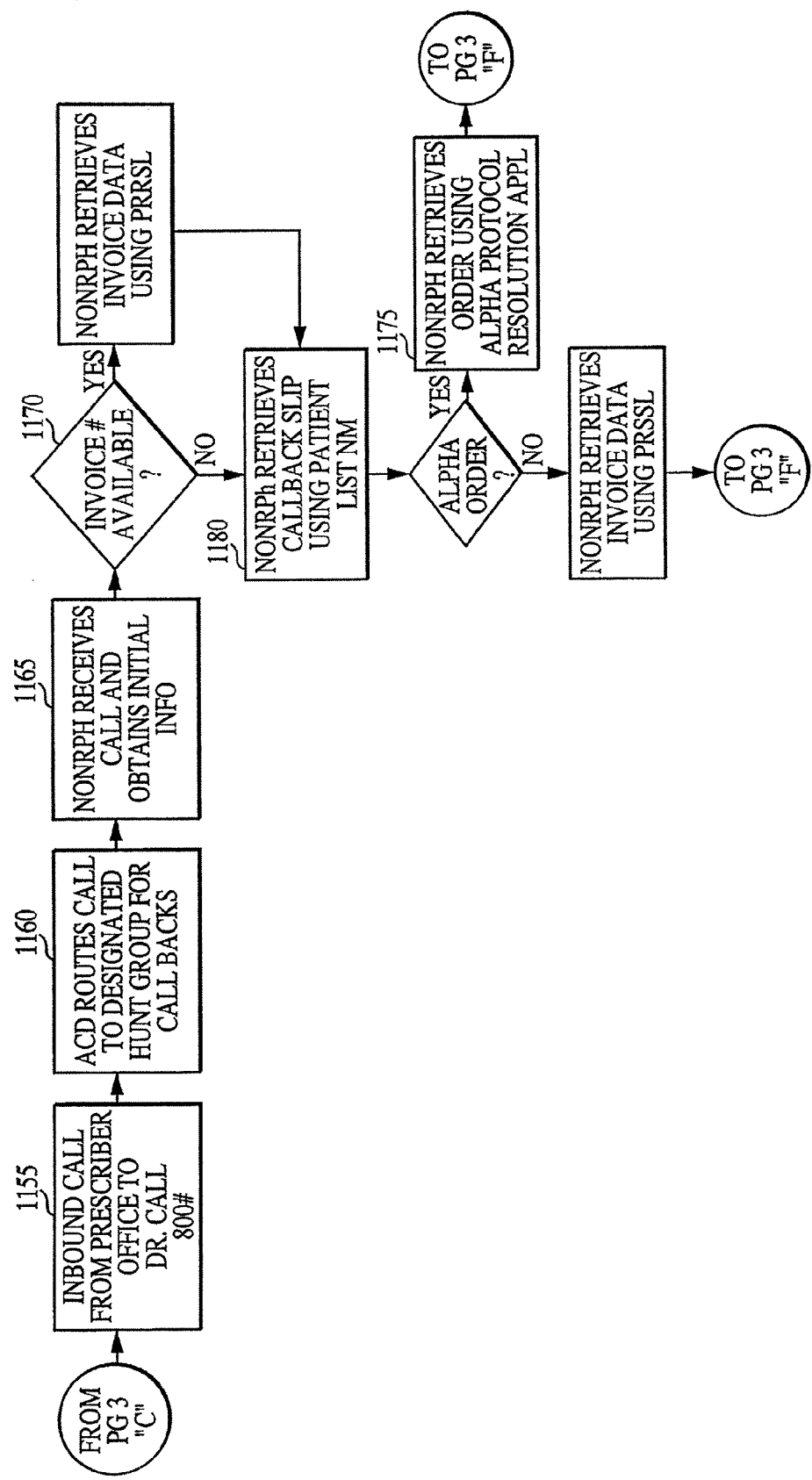
Figure 13D:
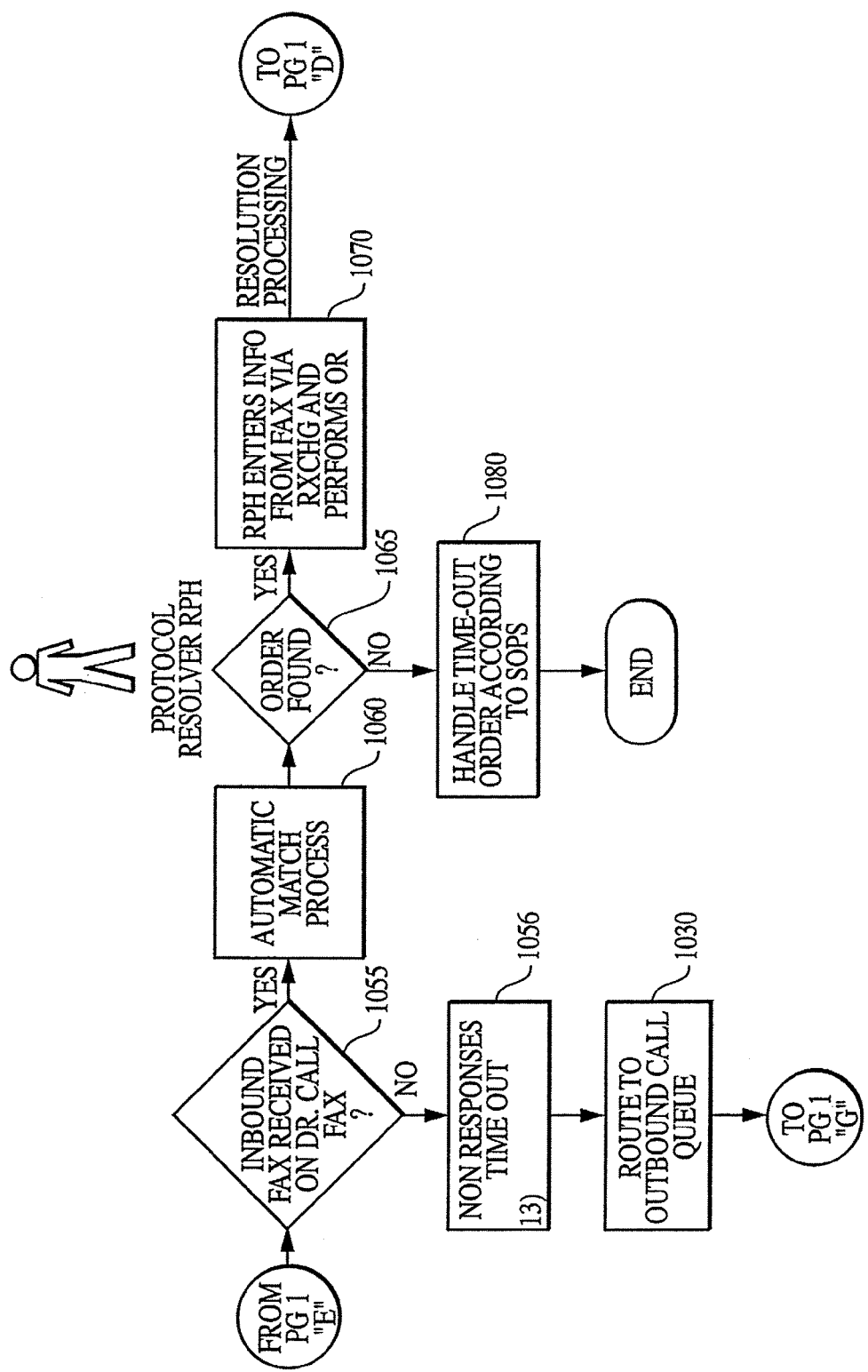
Figure 13E:
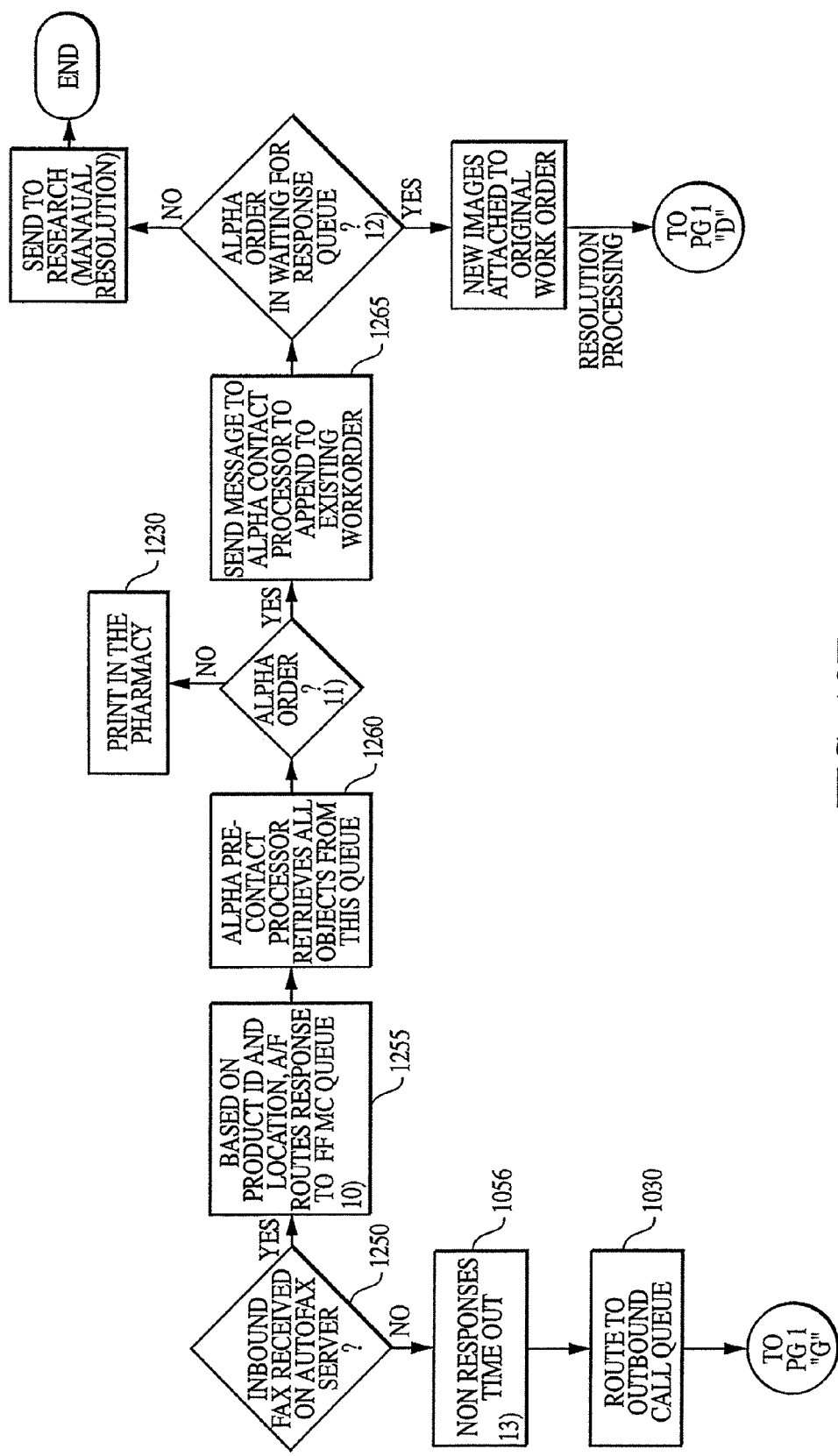

FIG. 13C illustrates an example of the prescriber call back process when the prescriber is responding at 1155 to a message left through the outbound call queue process. The call is routed at 1160 to the designated hunt group for call backs. A system user receives the call at 1165 and obtains the initial information. If the prescriber has the order invoice information 1170, the system user retrieves at 1175 the order using the invoice number or other protocol resolution application. Alternatively the system user retrieves at 1180 the generated call back slip from the outbound call queue procedure using the patient's last name. The system user once having located the order transfers at 1110 the call to a pharmacist. The call transfer is then followed by or is concurrent with at 1115 the user shelving the order and routing it to the pharmacist. The pharmacist retrieves at 1120 the order from the shelf and reviews at 1125 the intervention with the prescriber and resolves the protocol. The order is then submitted at 1130 to a work queue for further processing.

Alternatively, if an applicable protocol can be resolved at 1190 by an administrative protocol instead of contacting the prescriber or prescriber's office, the applicable administrative protocol(s) is applied at 1195 to the order from an administrative or rules relational database. If the order is not resolvable at 1190 by the application of an administrative protocol (s) a determination at 1200 is made as to whether the order has any outstanding calls to prescriber or a prescriber's office and if not the order is resolved at 1205 using a professional protocol(s) relational database. After at least one professional protocol(s) has been applied at 1205 to the resolution of the order, a determination at 1210 is made as to where a contact to a prescriber or prescriber's office is necessary to resolve any additional outstanding applicable protocols. If a prescriber call is determined at 1215 not to be necessary, a pharmacist indicates at 1220 which order items are to be called on and routes at 1030 the order to the outbound call queue. If a call is determined necessary, the order is updated at 1225 and routed at 1230 to a work queue for further processing.

However, if the order has associated with it an outstanding call(s) to a prescriber or prescriber's office, the order is queued at 1050 in a wait queue until either the prescriber or prescriber's office responds within the designated wait time or the time the order spends in the wait queue exceeds a predetermined value.

FIG. 14A-14E depict an example of the resolution of an order with a Managed Care protocol. A Managed Care protocol subsists within the Professional Protocols and arises when a therapeutically equivalent substitute medication is available for the one prescribed. The availability of a therapeutically equivalent substitute medication presents an 'interchange opportunity.' The prescriber is contacted by phone or fax to determine whether the prescriber will approve the interchange request.

A pharmacist reviews at 1300 the edits and initially determines at 1305 and 1310 if the prescription is a screen out or faxable, respectively. If the prescription is a 'screen out' the pharmacist resolves at 1315 the order per standard operating procedure and then releases at 1320 to a work queue for further processing at 1325. A screen out results from insufficient system resources or time to pursue a Managed Care opportunity or an interchange opportunity. Standard operating procedures include, for example, updating a system screen that notes the order was not pursued as an interchange. If the prescription is not a screen out, but is instead faxable an auto fax is launched. A date and time in which to receive a call back or other contact in response to outbound fax is appended at 1330 to the order. the system is updated at 1335 to reflect that an auto fax has been launched in furtherance of resolving the order. The order is placed at 1340 in a wait queue until either a response is received at 1343 within a predetermined time or the time the order spends in the wait queue exceeds at 1350 the predetermined time. If the time the order spends in the wait queue exceeds at 1341 the predetermined time, the order is routed at 1400 to the outbound call queue.

The outbound call queue is for an order that is non-faxable or an order for which the time the order has spent in a wait time queue has exceeded a predetermined value. An order in the outbound queue is retrieved at 1405 from the queue by a user. After the order is retrieved from the queue the user dials at 1400 the order prescriber. If the outbound call is answered at 1415 the user attempts 1420 to reach the prescriber or other decision maker. If the prescriber or other decision maker is reached the user introduces at 1425 the issue and if the number at 1430 from which the prescriber is contacted is a secure fax number the user updates at 1435 the prescriber's master file information and launches at 1325 an auto fax.

Figure 14A:
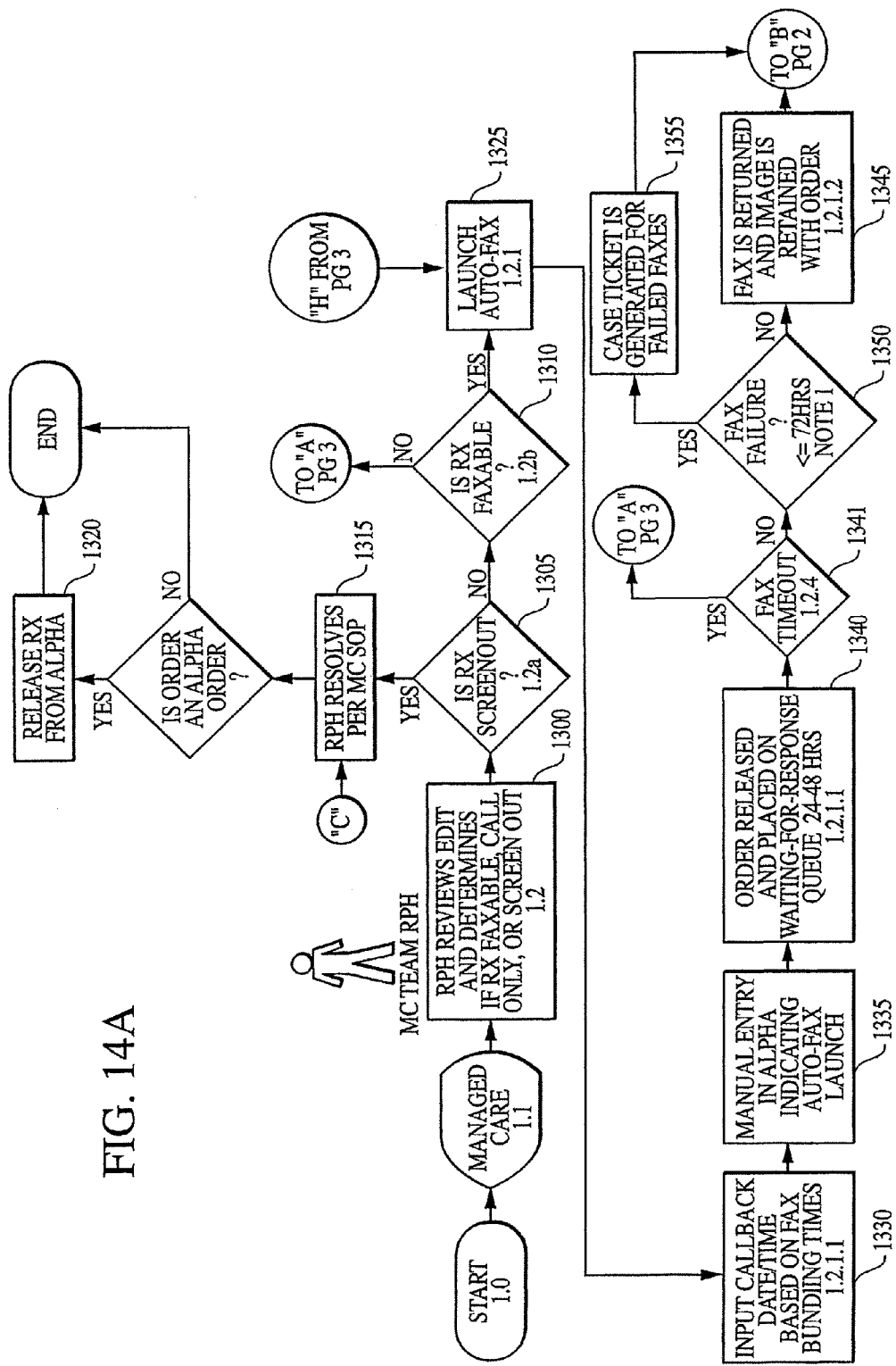
FIG. 14A-14E depicts a flow control diagram for the resolution of a Managed Care order.
Figure 14B:
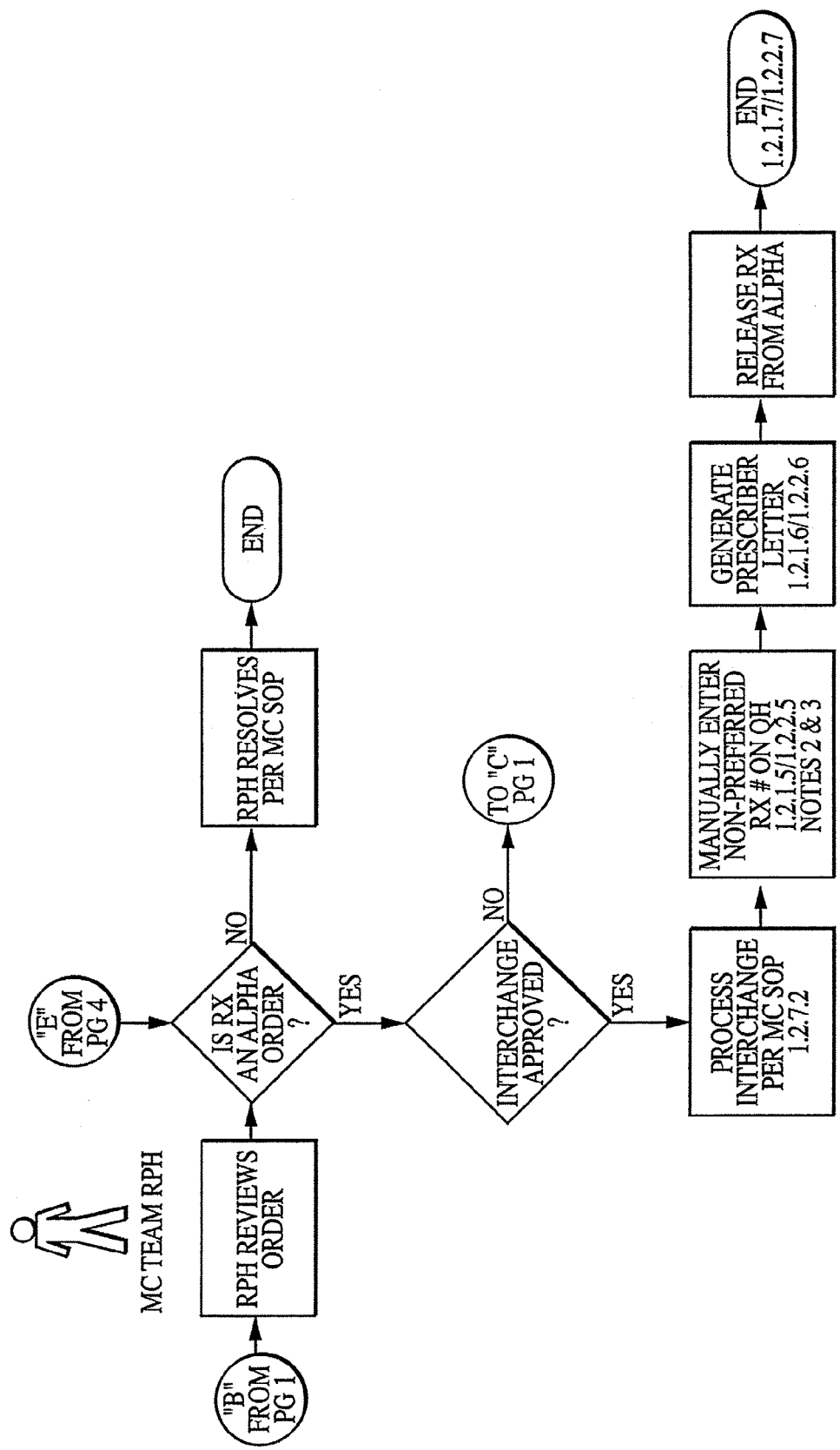
Figure 14C:
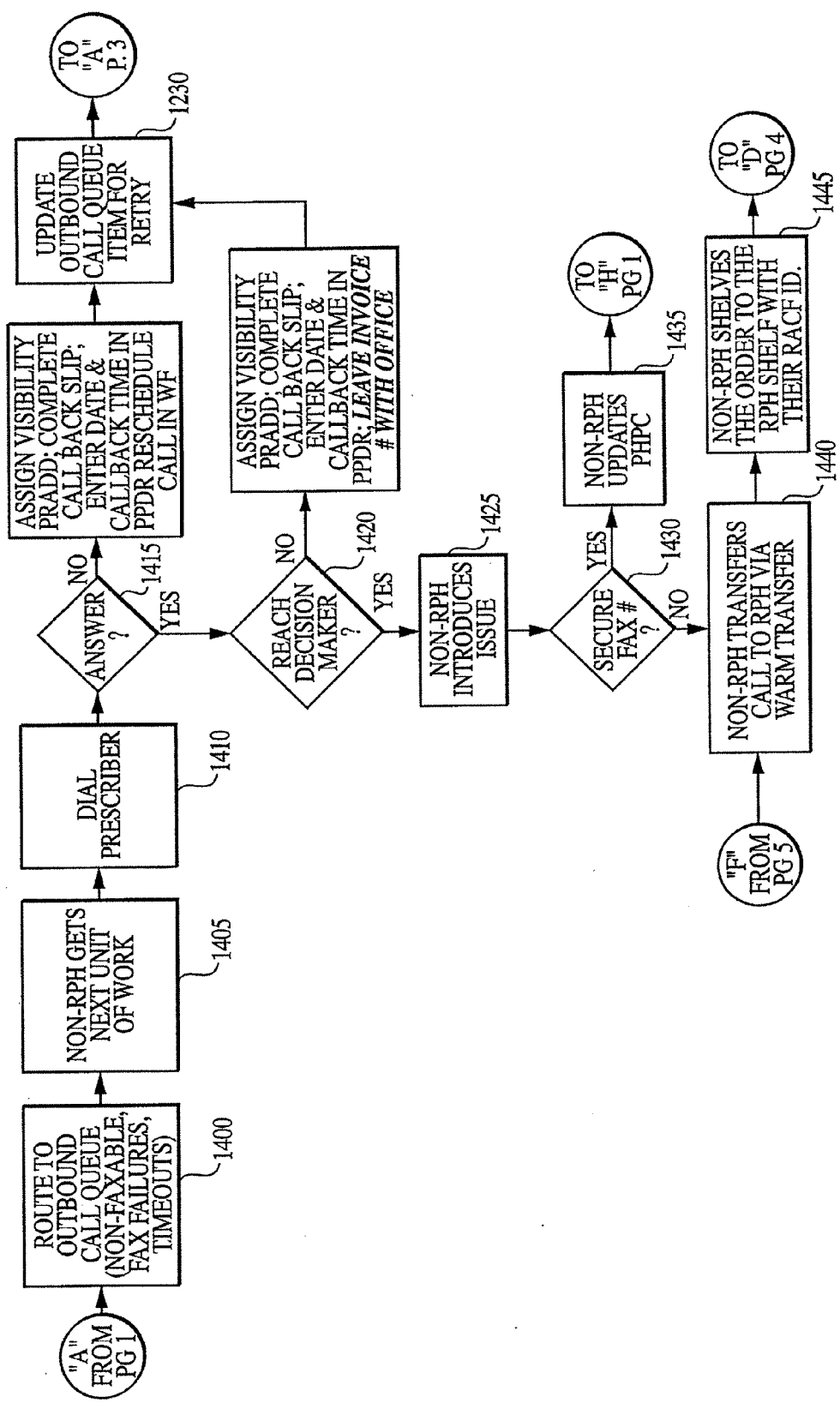
Figure 14D:
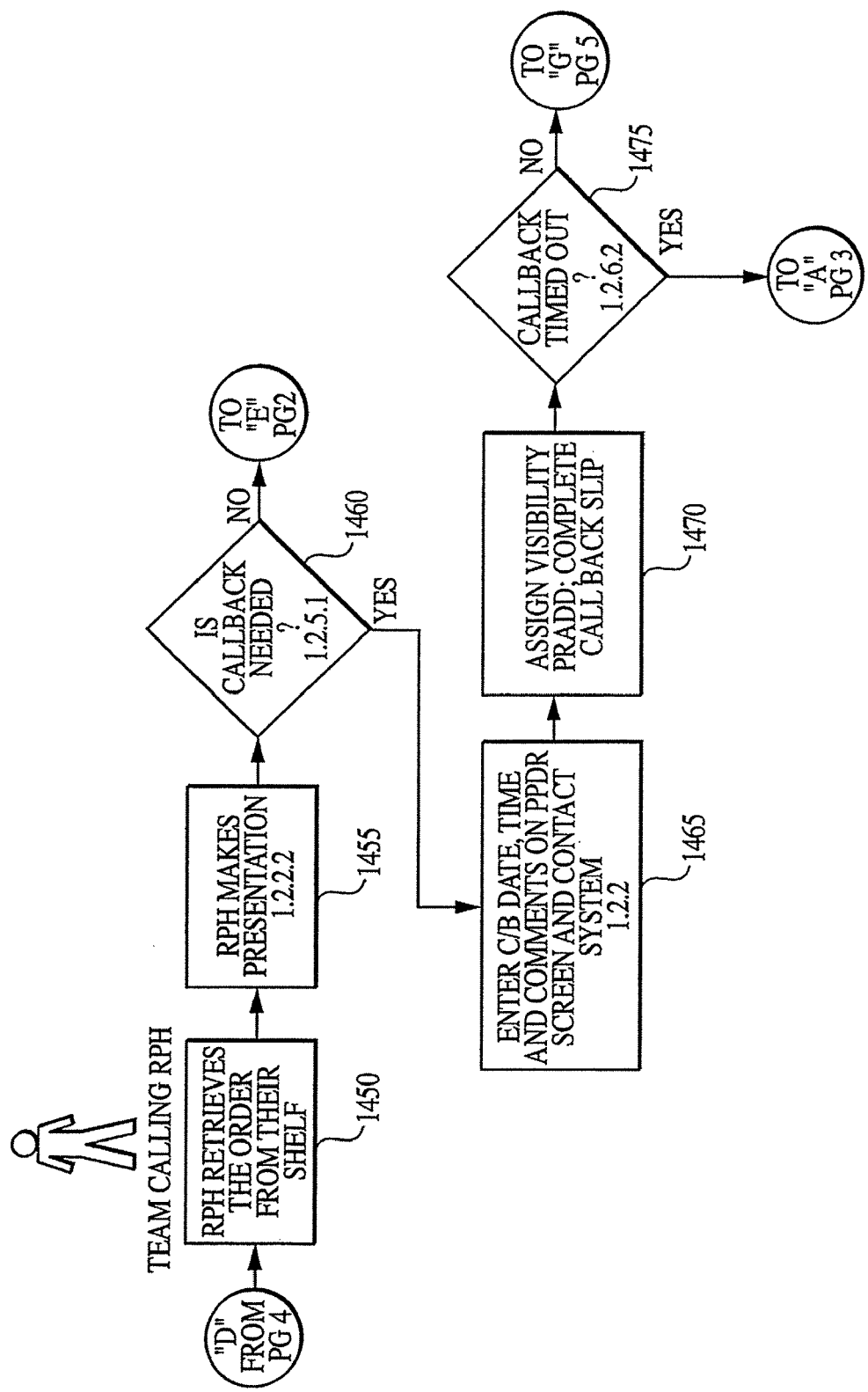
Figure 14E:
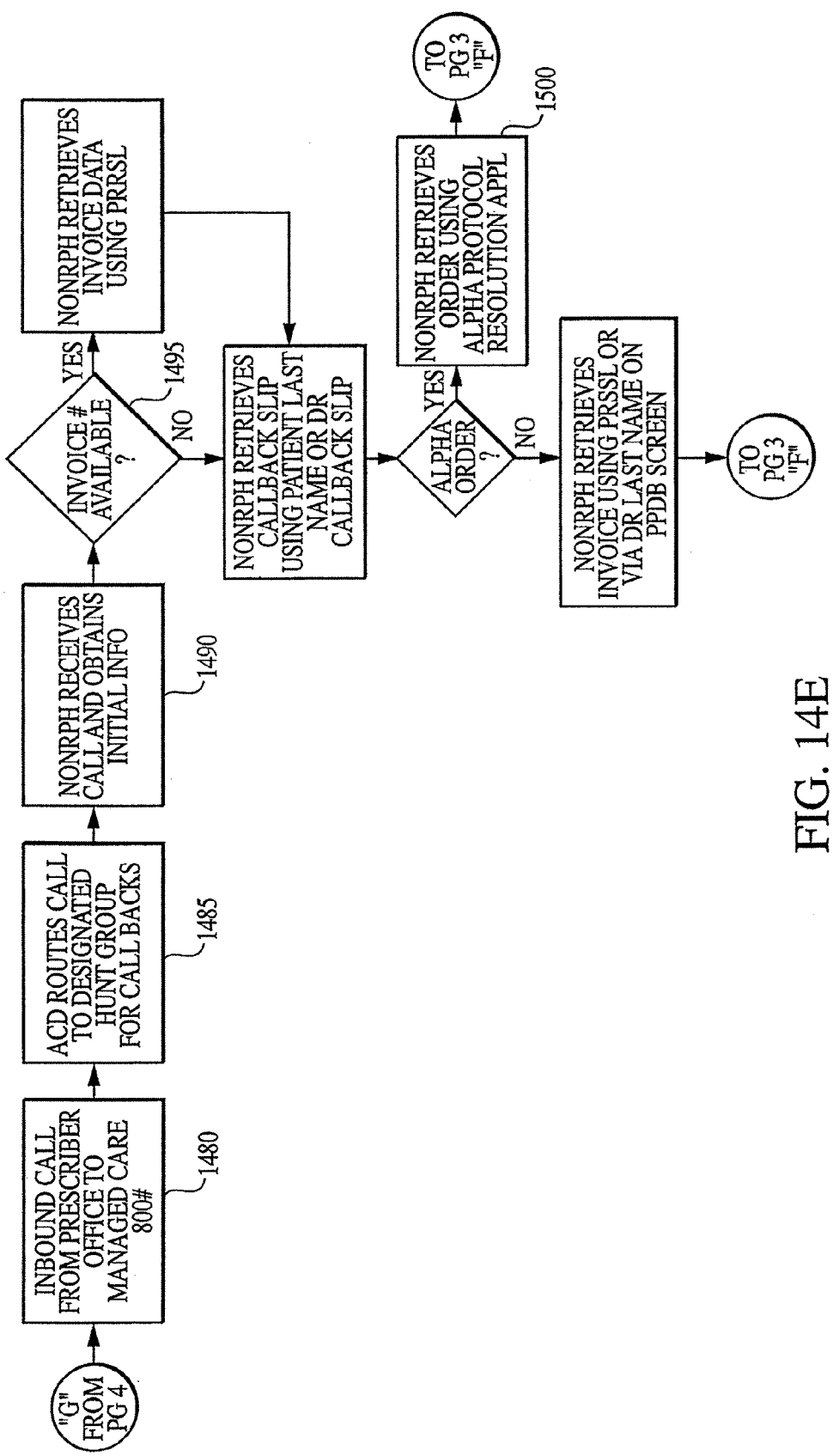
Figure 15A:
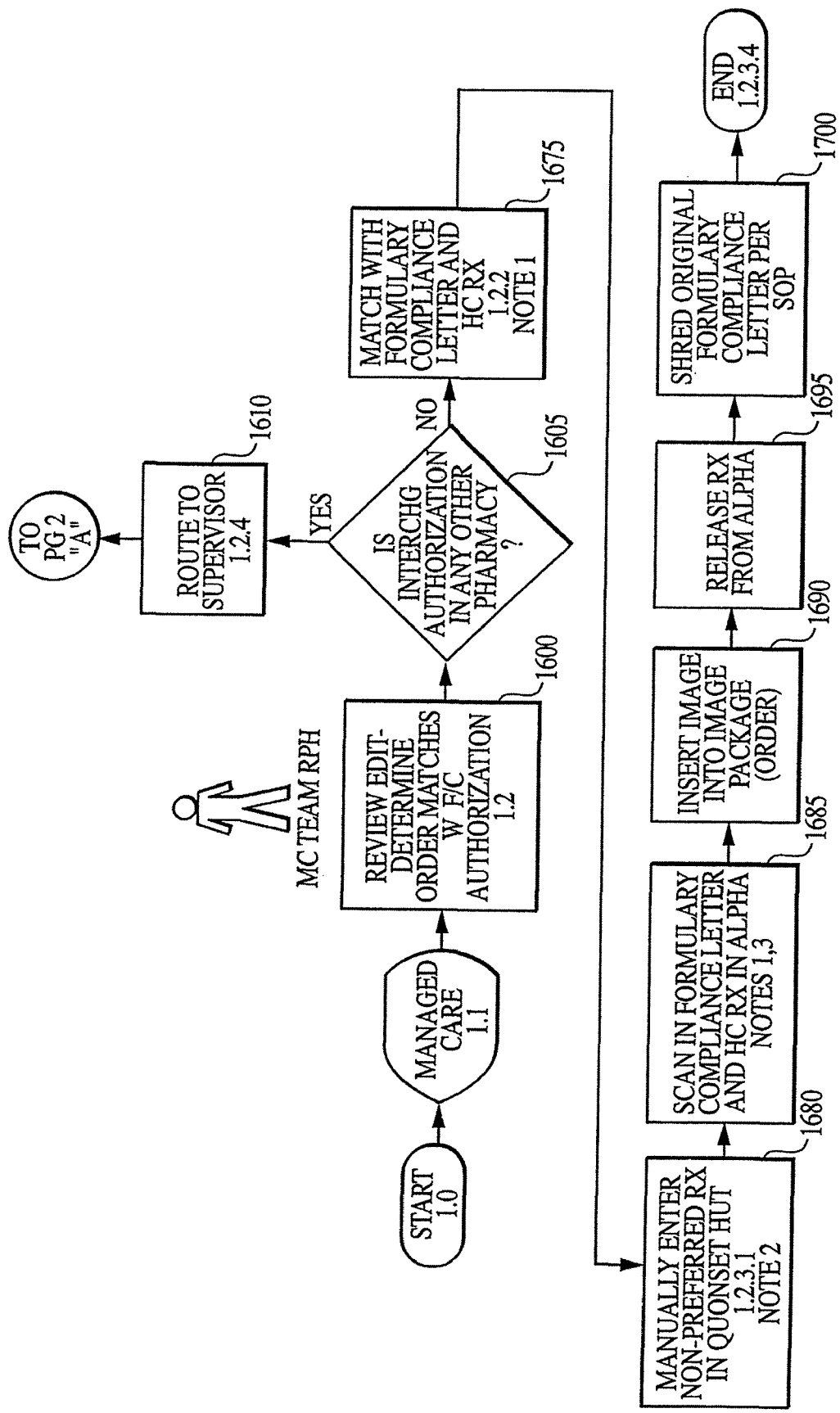
FIGS. 15A and 15B depicts a flow control diagram of an overlapping embodiment for the resolution of a Managed Care order.
Figure 15B:
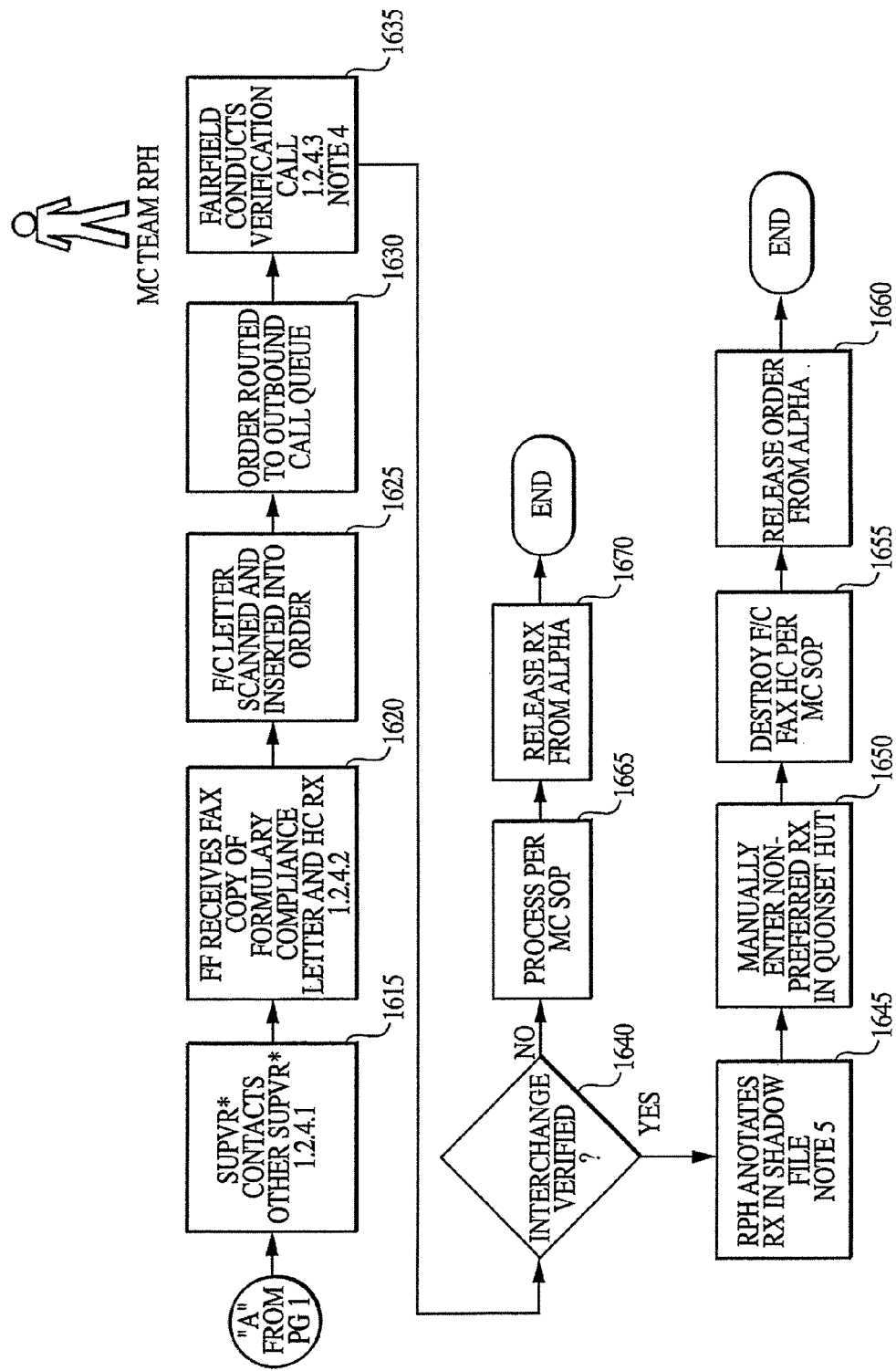
Figure 16A:
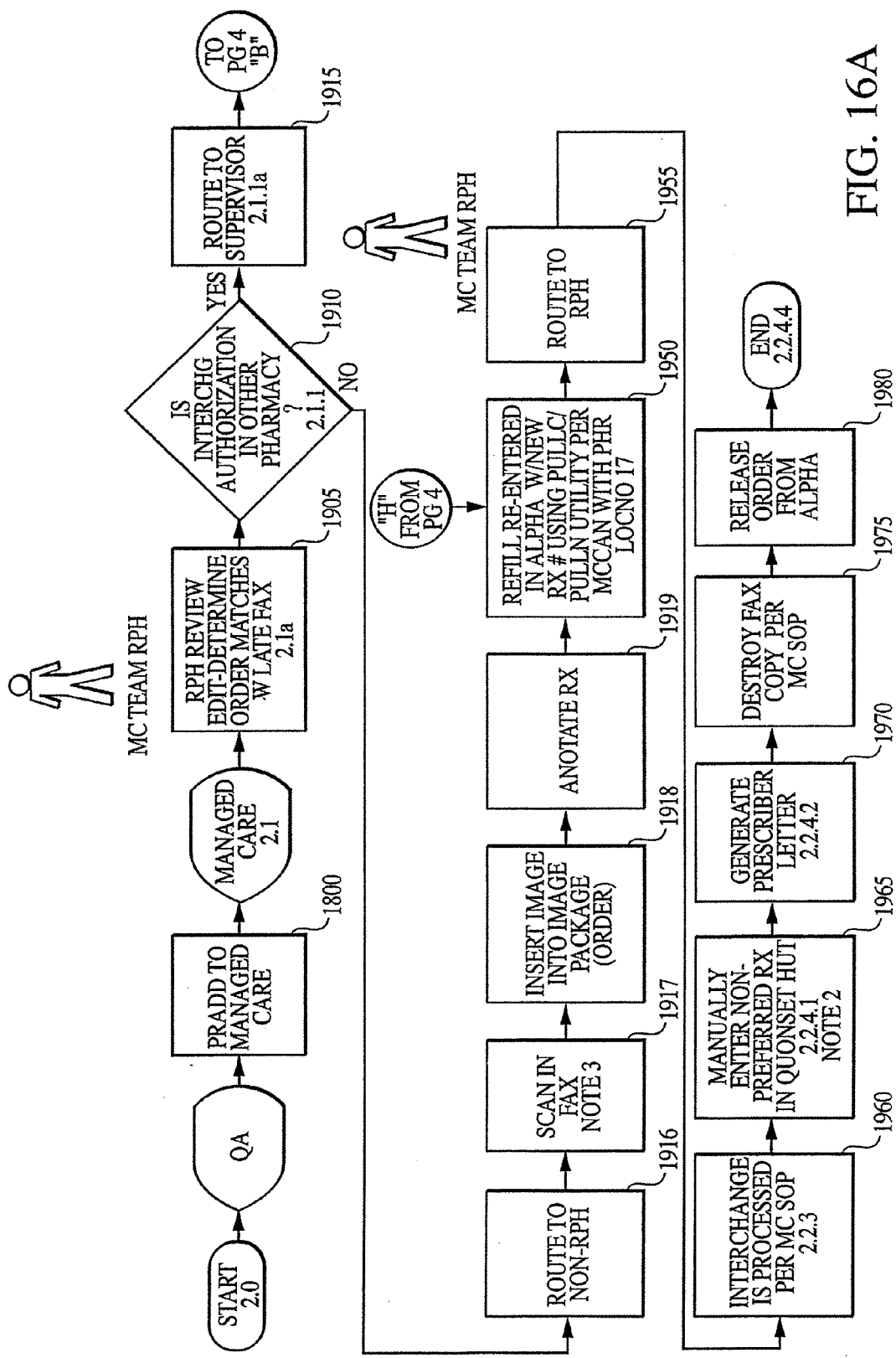
FIGS. 16A and 16B depicts a flow control diagram of an overlapping embodiment for the resolution of a Managed Care order.
Figure 16B:
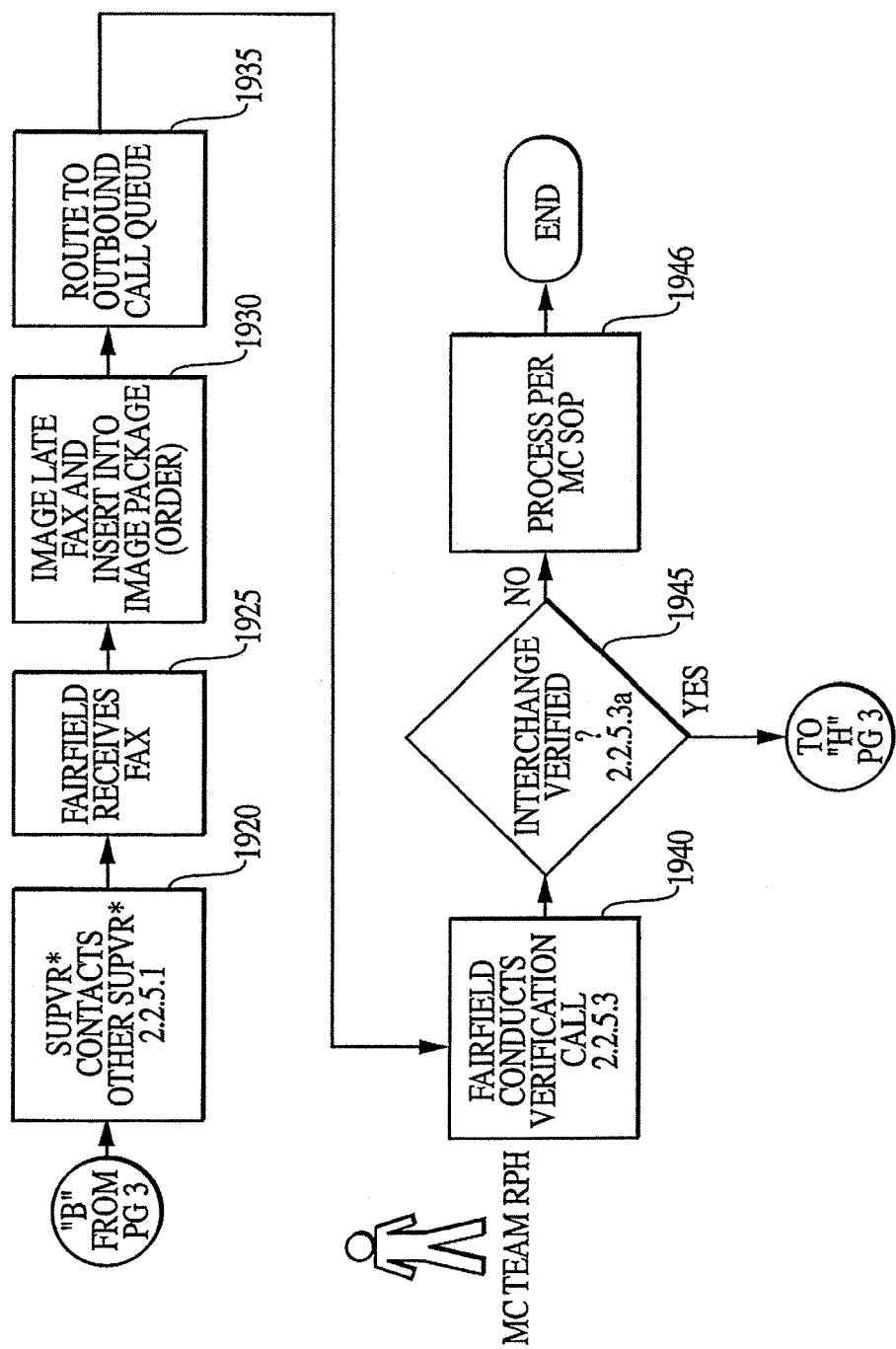

Alternatively, if the number from which the prescriber is contacted is not a secure fax number, the user transfers at 1440 the call to a pharmacist. Concurrent with or subsequent to the transfer of the call to the pharmacist the user routes at 1445 the order to the pharmacist's virtual shelf. The pharmacist retrieves at 1450 the order from the virtual shelf and discusses at 1455 the protocol to be resolved with the prescriber. If a call back is necessary 1460, the pharmacist enters at 1465 the call back date, time and comments in the prescriber contact tracking screen and the Contact System screen and assigns at 1470 a visibility protocol addition and completes a call back slip. If the time in which to conduct the call back is timed out 1475, the order is routed at 1400 to the outbound call queue and steps 1400 through 1415 of FIG. 14C are repeated.

Inbound calls received at 1480 within the predetermined time are routed at 1485 to their designated hunt group for call backs. A non-pharmacist receives at 1490 the call and obtains the initial information regarding the order. Initially, the non-pharmacist attempts at 1495 to located the order through its invoice number. However, if the caller does not have the invoice number the non-pharmacist attempts at 1500 to locate the order using a patient's last name, call back slip, or other protocol resolution application. If the caller does not have the invoice number the non-pharmacist will attempt to locate the order using Protocol Resolution, which allows the user to step through screens as needed.

FIGS. 12A and 12B depict an example of the resolution of an order with a Managed Care protocol attached to the order according to an alternative embodiment of the present invention. According to this embodiment, an approval for a drug interchange (switching to a generic version) occurs after a prescription has been processed. The approved order is flagged on the system so that the drug interchange occurs at refill time. The edits to the order are reviewed at 1600 to determine whether the order matches with formulary compliance authorization. If an interchange authorization is available 1605 in any other pharmacy, the order is routed at 1610 to a supervisor. The supervisor contacts at 1615 other supervisors. A fax indicating formulary compliance is received at 1620. The formulary compliance letter is scanned and inserted at 1625 into the order. The order is routed at 1630 to the outbound calling queue. A verification call is conducted at 1635 and if the interchange is verified 1640, the pharmacist annotates at 1645 the prescription in the shadow file and manually enters at 1650 non-preferred prescription in an application that prints patient and prescriber letters that are required by law. The application is referred to as a Quonset hut. The hardcopy of the fax formulary compliance letter is then destroyed at 1655 and the order is released at 1660 into a work queue for further order processing. If the interchange is not verified 1640, the order is processed at 1665 per managed care standard operating procedure and released at 1670 into a work queue for further order processing. The standard operating procedure includes, for example, manual procedures followed when an interchange is not approved and allows the system files to be updated so that order processing can continue.

However, if an interchange authorization 1605 is not available, an attempt to match at 1675 the formulary compliance letter. The non-preferred prescription is manually entered at 1680 in the Quonset hut. The formulary compliance letter and prescription hardcopy are scanned at 1685 into the system. The scanned images are inserted at 1690 into the other image order documents. The order is released at 1695 into a work queue for further order processing. The original formulary compliance letter is shredded at 1700 per standard operating procedure.

FIGS. 13A-13B depict examples of protocol resolution of an order with managed care protocols attached to the order according to an alternative embodiment of the present invention. Protocols are added at 1900 to the managed care order. The managed care order is reviewed at 1905 to determine whether the order matches with the late fax. If an interchange authorization exists 1910 in another pharmacy, the order is routed at 1915 to a supervisor who in turn contacts at 1920 other supervisors. The fax is received at 1925 and the late fax is imaged and inserted at 1930 into the order images order documents. The order is then routed at 1935 to the outbound call queue for a verification call. The verification call is conducted at 1940 and if the interchange is verified 1945, the refill for the prescription is entered at 1950 into the system with the new prescription number using the pull and copy (PULLC/PULLN) utility. The pull and copy utility copies a prescription into a new invoice. The order is then routed at 1955 to a pharmacist and the interchange is processed at 1960 according to managed care standard operating procedures. The non-preferred prescription is manually entered at 1965 in the Quonset hut. A prescriber letter is generated at 1970 and the late fax copy is destroyed at 1975 per standard operating procedure. The order is released into a work queue for further order processing. If the interchange is not verified 1945, the order is processed at 1946 according to managed care standard operating procedures.

If no interchange authorization exists 1910 in another pharmacy, the order is routed at 1916 to a non-pharmacist and the late fax is scanned and imaged at 1917. The imaged late fax is appended at 1918 to the imaged order documents and the prescription is annotated at 1919. The refill for the prescription is entered at 1950 into the system with the new prescription number using PULLC/PULLN utility. The order is then routed at 1955 to a pharmacist and the interchange is processed at 1960 according to managed care standard operating procedures. The non-preferred prescription is manually entered at 1965 in the Quonset hut. A prescriber letter is generated at 1970 and the late fax copy is destroyed at 1975 per standard operating procedure. The order is released at 1980 into a work queue for further order processing.

Command and Control

Figure 17:
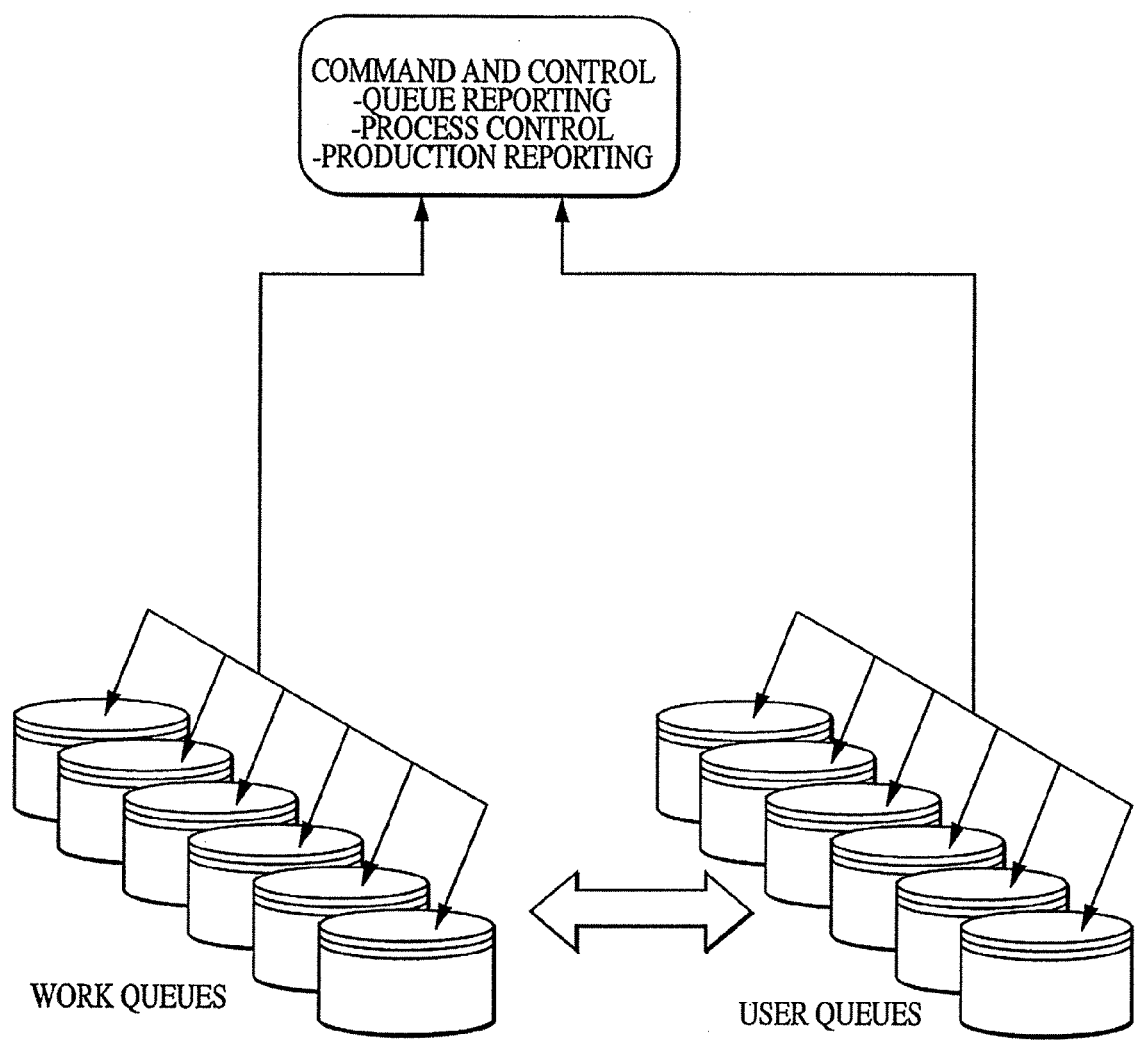
FIG. 17 depicts a schematic of information flow to Command and Control.

FIG. 17 depicts a schematic of information visibility to the Command and Control module. The Command and Control module is a user interface that sits atop the order processing system. The Command and Control module tracks work queue activity, individual user activity, process control information, system production and system resource availability. The Command and Control module can extract information on any single queue or groups of queues and perform manipulations on the extracted data through standard database query tools to produce status reports on any single, or in combination, aspect of the system. The data in the resultant reports are hyperlinked to the underlying data used to generate them.

Figure 18:
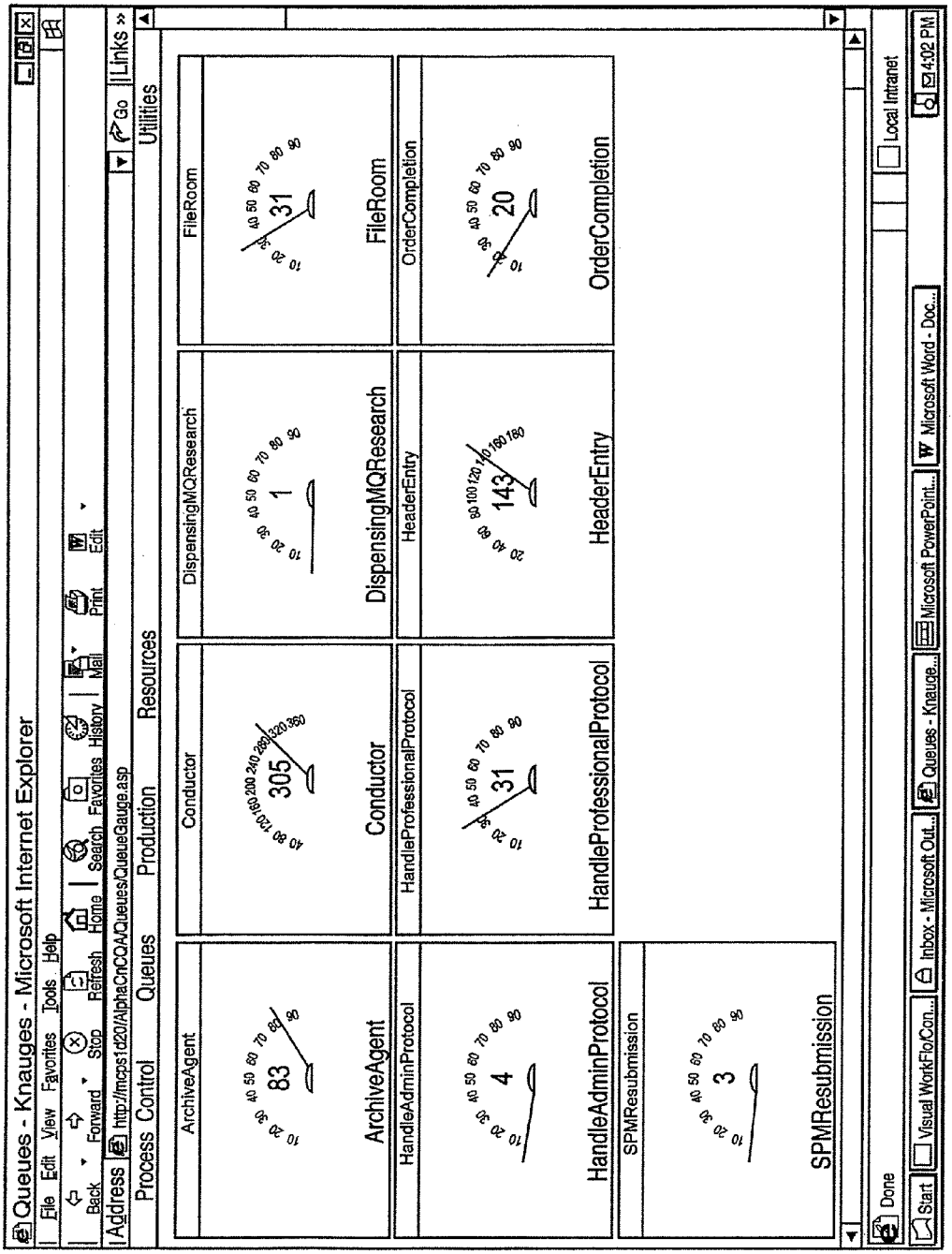
FIG. 18 depicts an example of an instrument panel screen from the Command and Control interface.

FIG. 18 depicts an example of an instrument panel that is part of the user interface of the Command and Control module. FIG. 18 depicts a screen containing instrument panels representing the states of selected system queues. The gauges of the instrument panel indicate the quantitative loads in each selected queue present in the instrument panel. Each gauge also provides an indication of the health of each represented queues by its color. The range of colors each gauge can assume are predetermined and are selected to indicate at least three queue health states. The first color indicates that the queue is healthy and not overloaded. The second color indicates caution and that the queue is approaching a critical load point. The third color indicates that the queue has exceeded its critical load point and system adjustments must be made to rebalance the load to bring down the queue level to within an acceptable operating range.

Figure 19:
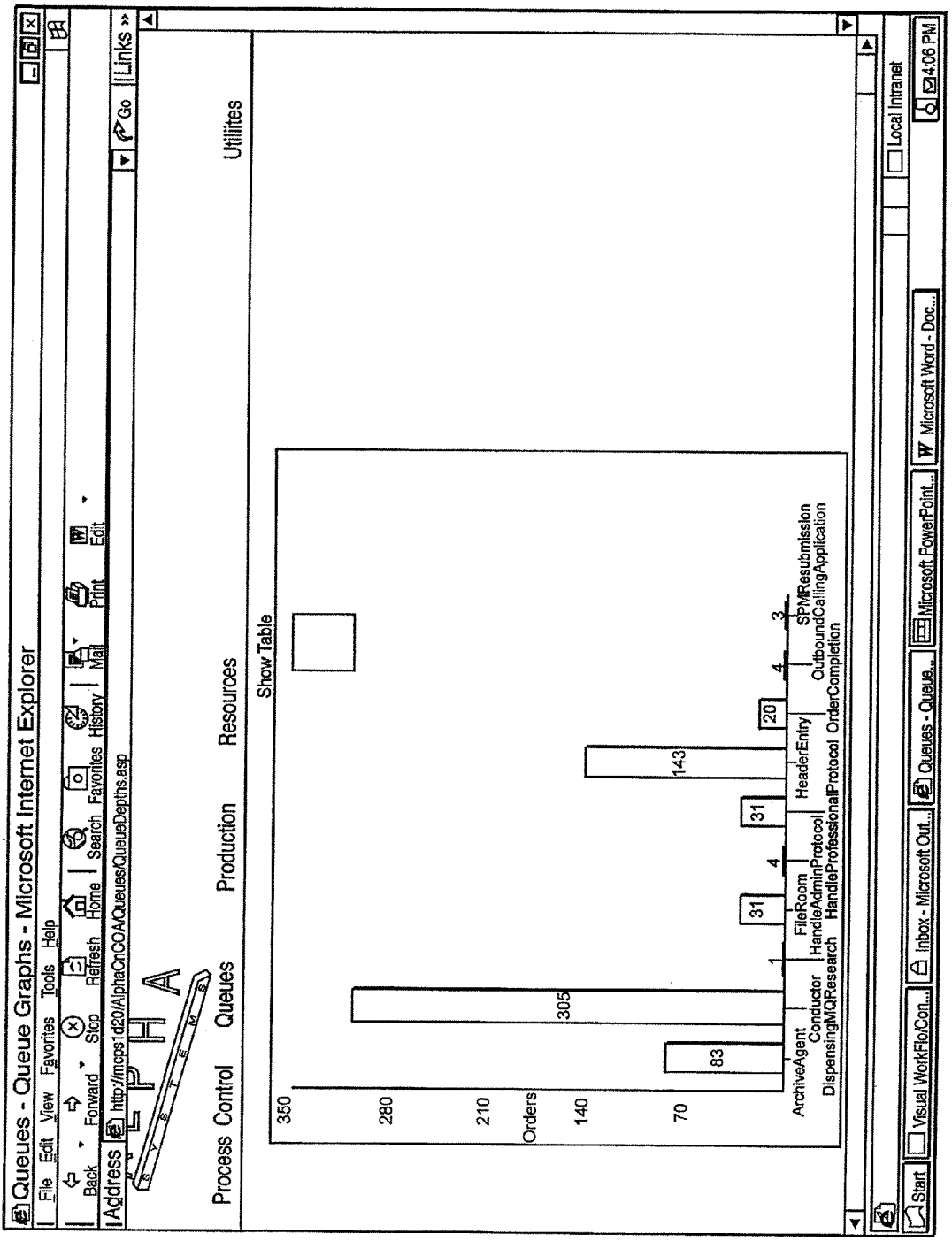
FIG. 19 depicts an example of a bar graph queue population screen from the Command and Control interface.
Figure 20:
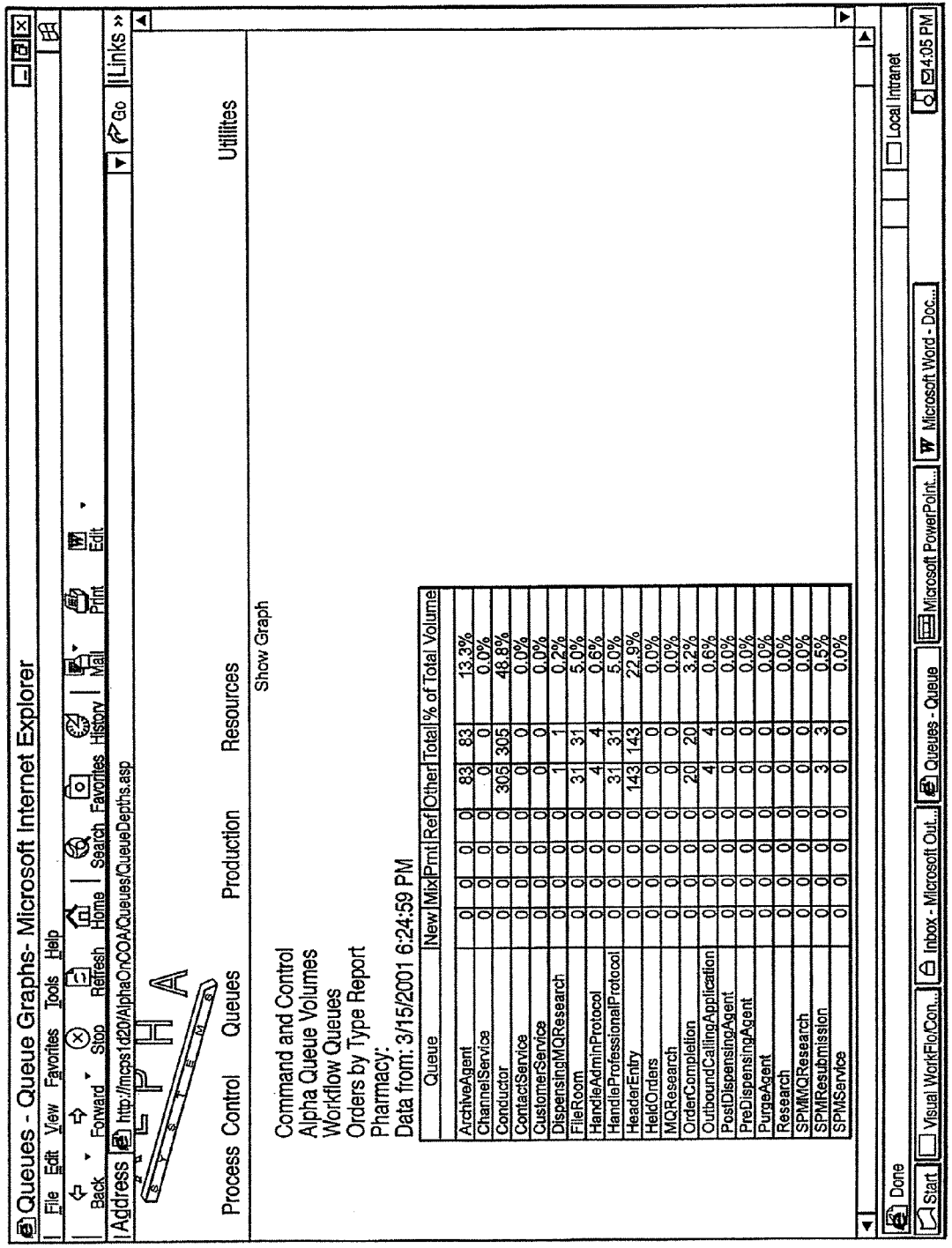
FIG. 20 depicts an example of a queue data table screen from the Command and Control interface.
Figure 21:
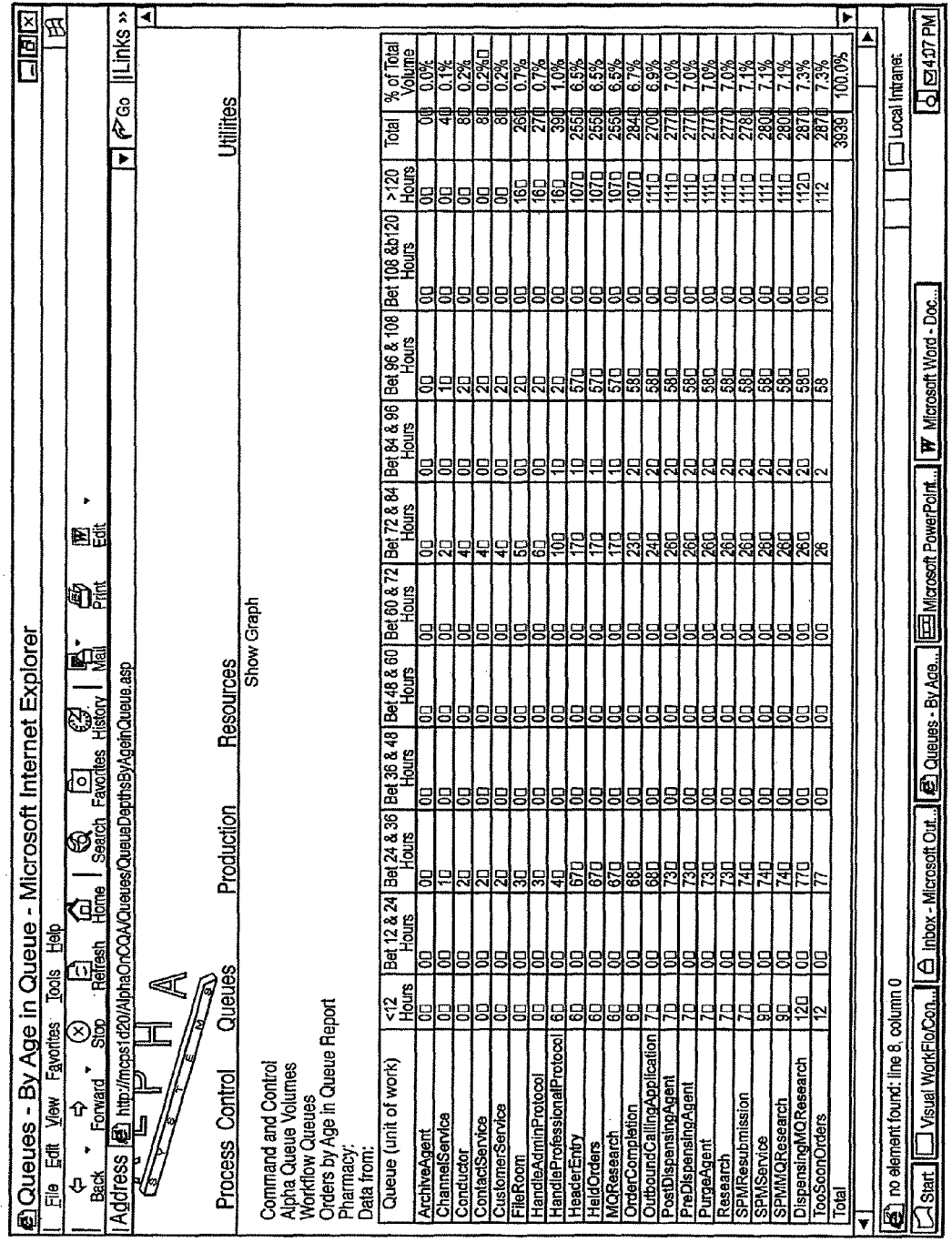
FIG. 21 depicts an example of a queue data table screen from the Command and Control, wherein the columns of the table are represent time slices relating to the length of time a population of orders is in a particular queue.

Each gauge is hyperlinked to the underlying data responsible for the gauge representation. Selecting a particular gauge drills down to all the orders in the queue representing the gauge. The orders within the selected queue can be configured to be displayed in either graphical, as shown in FIG. 19, or table format, as shown in FIG. 20, wherein the ordinate and the abscissa of any graphical format or the columns and rows of the table are configurable by a user to represent orders within a queue by a number of variables including, for example, slicing the time from the newest arrived order to the queue to the longest held order in the same queue into predetermined intervals to show the distribution of orders in the queue by time. An example of this is shown in FIG. 21.

FIG. 19 depicts a graphical representation of select system queues. FIG. 20 is a bar graph wherein each bar represents a particular queue and the height of the bar represents the number of orders in that queue. Each bar in the bar graph is hyperlinked to its underlying queue and linking to the underlying data provides a list of the all the orders in the selected queue.

FIG. 20 depicts select system queues in table format wherein each queue is broken out into categories or types of orders contained in the queue, the total number of system orders in any one queue, and the percent of the total system orders are in any one queue. Queue categories include, for example, whether the order is a new prescription, a refill prescription, or a mix of both new prescriptions and refill prescriptions, how many orders are just payments alone without orders, and how many orders are in a miscellaneous catch all category. The table entries are hyperlinked to their supporting data and allow a user to link or drill down to the underlying data.

Figure 22:
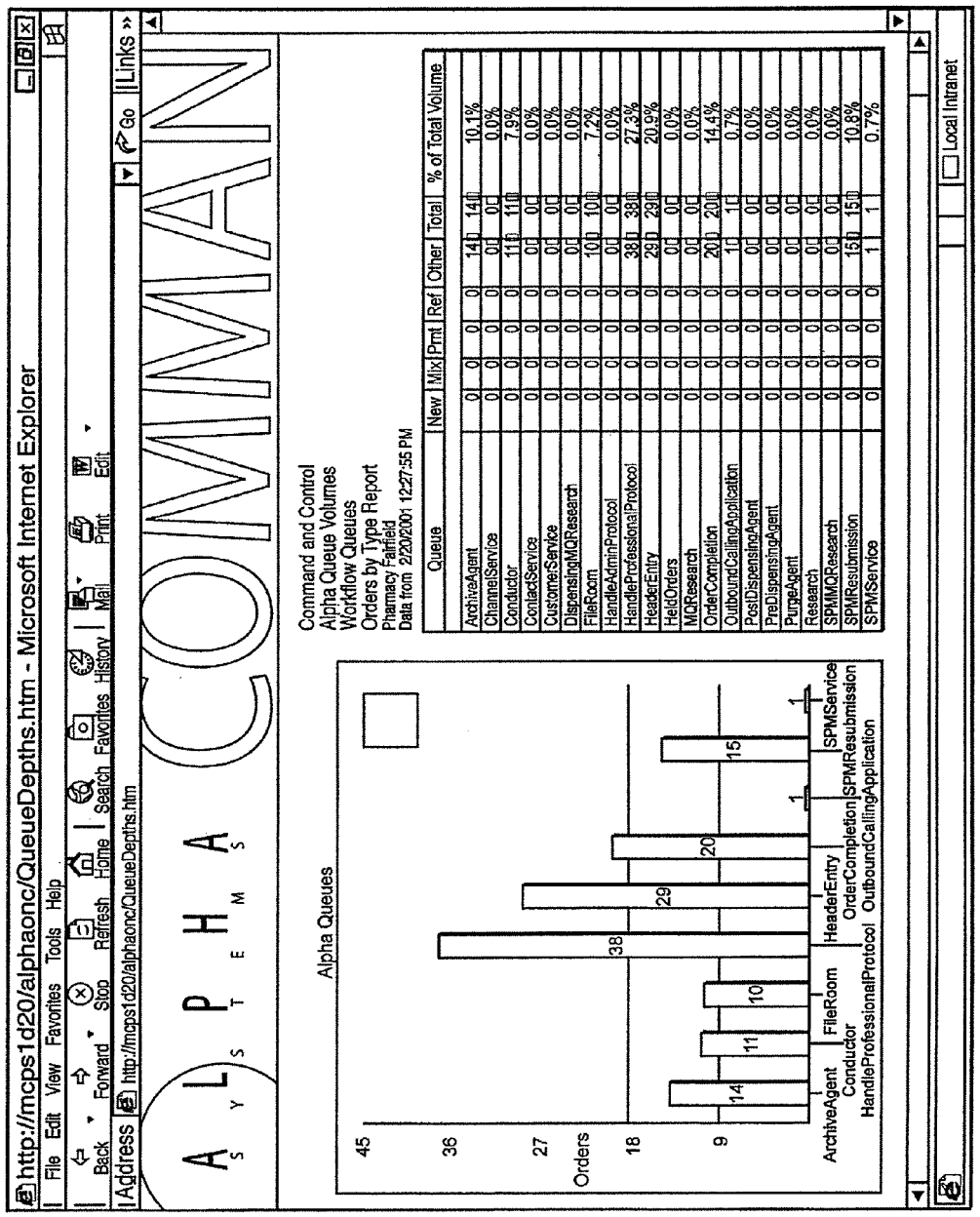
FIG. 22 depicts an example of a combined queue data table and bar graph queue population screen from the Command and Control interface.

FIG. 22 represents a combination screen in which both a bar graph of select queues and a table of select queues are provided. The queues presented in the bar graph do not necessarily have to be the same queues presented in the table.

The Command and Control module of the present invention also provides several positive control mechanisms for the tracking of an order in the order processing system. One positive control mechanism, and an alternative embodiment of the present invention, involves each system queue acknowledging the receipt of an order from the preceding queue from which the order was immediately received. Another positive control mechanism, and an alternative embodiment of the present invention, involves the order processing system of the present invention sending an alert to the user or paging the user whenever an order has been in one particular longer than a predetermined time.

Positive control also provides the user with the capability of locating any order in the system and reviewing its journey through the pharmacy or order processing system. Ways in which to query the positive control database to review an order include, for example, by Invoice Number, by Prescription Number, by Member Number, and by Work Order ID. Starting with any one of the above pieces of information, a user can identify, for example, the following: the queue in which an order currently resides, the queues where the order has been, the amount of time the order spent in each queue, and the total elapsed time that the order has been in the pharmacy.

The Command and Control module of the present invention can be configured to provide browser-based functionality and is capable of operating on any suitable personal computer or workstation.

Network Configuration

Figure 23:
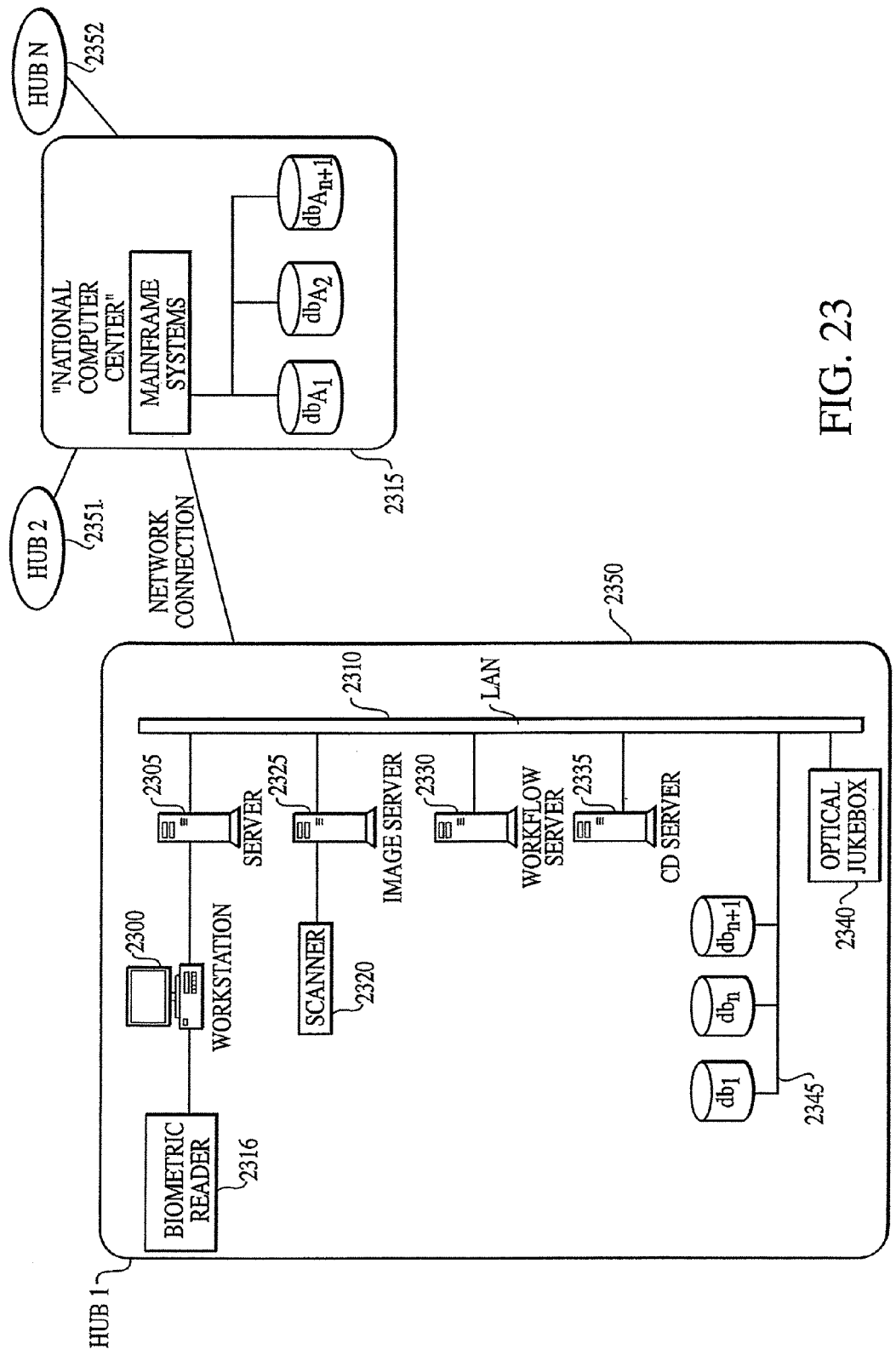
FIG. 23 shows one possible hardware and network configuration for a system according to the present invention.

FIG. 23 shows one possible hardware and network configuration for a system according to the present invention. PC workstation 2300 are attached to data server 2305 which is attached to a local area network (LAN) 2310. The data server 2305 communicates with the other servers on the LAN and a mainframe system 2315 to present a user with workcases. Also attached to the PC workstation 2300 is a biometric capture device 2316 which controls access to the PC workstation 2300 and thus the data server 2305, the LAN 2310 and the system mainframe 2315. An optical scanner 2320 (which may include a bar code reading capability) is attached to an image server 2325 which is attached to the LAN 2310. A workflow sever 2330 is attached to the LAN 2310 and manages the flow of orders. A optical disc server 2335 and jukebox 2340 is attached to the LAN 2310 for image archival purposes. Also attached to the LAN 2310 are a system of relational databases 2345 that identifies the system processing logic. The entire ensemble of components connected to the LAN 2310 represents a single HUB 2350 or order processing center. One network configuration of the present invention consists of system of geographically distinct HUBs 2351, 2352, and 2353 respectively, connected to a central system mainframe 2315.

Distributed Order Processing

According to an alternative embodiment of the present invention, the functionality performed by each processor of FIG. 1 can be distributed across several HUBs. For example, HUB1 conducts all the preprocessing and scanning of incoming mail whereas HUB2 is responsible for the entry of all non-clinical data with HUB3 conducting only clinical order entry and/or verification. HUB4 would then execute the actual dispensing and shipping. Alternatively, the processing tasks can be distributed across HUBs based on front end and back end tasks. For example, a single HUB may execute all the order processing steps up until and including routing the order to a dispensing pharmacy or pharmacies whereas a second HUB would execute all the order dispensing and shipping steps.

Alternatively each HUB would receive and process orders from its assigned geographic region. For example, a New York HUB would receive and process orders from states in the Northeastern United States while a central California HUB would receive and process order from states in the Southwestern United States.

The present invention is not limited to applications involving the processing of medical prescriptions but can be applied to any situation in which a mail order industry desires to decrease its reliance on paper documents and manual document transmittal methods. The various processes and flow charts described herein may be modified and/or sequenced differently.

In general, it should be emphasized that the various components of embodiments of the present invention can be implemented in hardware, software, or a combination thereof. In such embodiments, the various components and steps would be implemented in hardware and/or software to perform the functions of the present invention. Any presently available or future developed computer software language and/or hardware components can be employed in such embodiments of the present invention. For example, at least some of the functionality mentioned above could be implemented using C or C++ programming languages.

Preferred and alternate embodiments of the present invention have now been described in detail. It is so noted, however, that this description of these specific embodiments is merely illustrative of the principles underlying the inventive concept. It is therefore, contemplated that various modifications of the disclosed embodiments will, without departing from the spirit and scope of the invention, be apparent to persons of ordinary skill in the art.

What is claimed is:

1. A system for processing orders for at least one medical prescription comprising:
    a computer network;
    a computer processor connected to the network;
    storage and memory connected to the computer processor for storing orders, images of orders, and software modules;
    at least one scanner connected to the computer processor for scanning documents;
    communication link connected to the computer processor for communicating with users;
    at least one display connected to the computer processor for displaying order images;
    at least one protocol resolving database connected to the computer network;
    at least one facsimile machine in communication with the network;
    an image quality control processing module, stored in a computer readable storage media, said image quality control processing module executable in said computer processor, said image quality control processing module configured to determine whether the order of the at least one medical prescription requires conversion to an image, monitor the quality of images captures, selectively accept and/or reject images captured by said at least one scanner responsive to the monitored quality;
    an order header processing module, stored in a computer readable storage media, said order header processing module executable in said computer processor, said order header processing module configured to review and receive non-clinical data associated with said order;
    an order completion processing module, stored in a computer readable storage media, said order completion processing module executable in said computer processor, said order completion processing module configured to review and receive clinical data associated with said order;
    a protocol resolution processing module, stored in a computer readable storage media, said protocol resolution processing module executable in said computer processor, said protocol resolution processing module configured to resolve applicable protocols associated with said order;
    a doctor calls processing module, stored in a computer readable storage media, said doctor calls processing module executable in said computer processor, said doctor calls processing module configured to receive and process information regarding said order and determine whether the order requires at least one of communicating and transmitting the information with a prescriber to resolve a protocol;
    a command and control processing module, stored in a computer readable storage media, said command and control processing module executable in said computer processor, said command and control processing module configured to monitor and receive input to said system and to determine whether a prescription remains in any one of a plurality of system queues longer than a predefined value, wherein an alert notification is generated upon exceeding the predefined value.

2. The system of claim 1, further comprising an order dispensing module, stored in a computer readable storage media, said order dispensing module executable in said computer processor, said order dispensing module configured to dispense said order.

3. The system of claim 1, further comprising a shipping processing module, stored in a computer readable storage media, said shipping processing module executable in said computer processor, said shipping processing module configured to generate shipping manifests for said order.

4. The system of claim 1, further comprising an incoming paperless order processing module, stored in a computer readable storage media, said incoming paperless order processing module executable in said computer processor, said incoming paperless order processing module configured to receive said order in electronic format.

5. A graphical user interface embodied on a non-transitory computer readable medium and implemented by a management computer for inputting, displaying and managing in real time a prescription order fulfillment system stored in a database, the prescription order fulfillment system comprising at least one queue for resolving at least one prescription order element, the graphical user interface comprising:
    at least one process control screen, wherein each at least one process control screen is connected to the management computer system and comprises at least one selectable icon or field or combination thereof where the at least one icon, field or combination thereof is selectable by the management computer system, and graphically depicting one of at least one prescription order element;
    at least one queue screen, wherein each at least one queue screen comprises at least one selectable icon or field or combination thereof, depicting, in at least one of graphical or table format, at least one prescription order element in aggregate in a system queue and wherein the at least one system queue is user selectable;

at least one production screen, wherein each at least one production screen comprises at least one selectable icon or field or combination thereof, graphically depicting at least one production element of at least one prescription order element;

at least one system resource screen, wherein each at least one system resource screen comprises at least one selectable icon or field or combination thereof, graphically depicting by the management computer system at least one system resource element in relation to at least one prescription order element and tracking system resource availability; and at least one status screen, wherein each at least one status screen displays receipt of the at least one prescription order element from a first system queue visually depicting a first status of a first order processing step from a plurality of order processing steps performed by the prescription management system to a second system queue visually depicting a second status of a second order processing step for a specific prescription order element, and the second system queue acknowledging the receipt of the at least one prescription order element from the first system queue.

6. The graphical user interface of claim 5, wherein each process control screen is a search template with a plurality of fields.

7. The graphical user interface of claim 5, wherein each process control screen comprises an icon for generating process control report screens.

8. The graphical user interface of claim 5, wherein each queue screen is a graphical representation of an instrument panel, wherein said instrument panel comprises gauges, wherein said gauges indicate the state of a plurality of system queues.

9. The graphical user interface of claim 8, wherein each gauge is selectable and selecting said selectable gauge drills down from a system queue level of detail screen to an individual order level of detail screen.

10. The graphical user interface of claim 8, wherein said gauges are selected from the queues consisting of: archive agent, conductor, dispensing, file room, administrative protocols, professional protocols, header entry, order completion, channel service, contact service, customer service, held orders, research, outbound calling application, purge agent, and queue resubmission.

11. The graphical user interface of claim 5, wherein queue screen is a bar graph, wherein said bar graph depicts the number of orders in each system queue.

12. The graphical user interface of claim 11, wherein each bar in said bar graph is selectable and selecting said selectable bar drills down from a system queue level of detail screen to an individual order level of detail screen.

13. The graphical user interface of claim 5, wherein each queue screen is a graphic of a table with rows and columns, wherein said table includes entries that comprises information about system queues.

14. The graphical user interface of claim 13, wherein said table includes selectable entries, wherein selecting said selectable entries drills down from a system queue level of detail screen to an individual order level of detail screen.

15. The graphical user interface of claim 13, wherein said columns and rows of said table are configurable by a user.

16. The graphical user interface of claim 15, wherein said configurable columns are configurable to display the length of time orders have been in a queue.

17. The graphical user interface of claim 5, wherein selecting an entry from said table links to a screen, wherein said screen comprises information associated with orders represented in selected table entry.

18. The graphical user interface of claim 5, further comprising at least one filter icon, wherein selecting said at least one filter icon filters out select information present in any one of at least one process control screen, at least one queue screen, at least one production screen, at least one system resource screen or combination thereof.

19. The graphical user interface of claim 18, wherein said filters are configurable and allow a user to view all the orders completed by another user of the system.

20. The system of claim 1, further comprising:
the command and control module providing a predetermined level of access to at least one of a plurality of queues by a user responsive to a profile assigned to the user.

21. The graphical user interface of claim 5, wherein the ordinate and abscissa of the displayed graphical format can be configured to represent prescription orders associated with the at least one system queue by variables comprising predetermined intervals to show the distribution of orders in the at least one system queue by time.

22. The graphical user interface of claim 5, wherein the columns and rows of the displayed table format can be configured to represent prescription orders associated with the at least one system queue by variables comprising predetermined intervals to show the distribution of orders in the at least one system queue by time.

23. The graphical user interface of claim 8, wherein the gauge of the instrument panel is indicative of the quantitative loads in the at least one system queue.

24. The graphical user interface of claim 23, wherein the gauge is color coded to be indicative of at least one of not overloaded, approaching a critical load point and overloaded.

25. The graphical user interface of claim 5, wherein each queue screen comprises information about system queues including the length of time orders have been in a queue.

26. The graphical user interface of claim 5, wherein the second system queue acknowledges the receipt of the at least one prescription order element from the first system queue and updates the second system queue responsive to the receipt of the at least one prescription order element from the first system queue.

27. The graphical user interface of claim 5, further comprising a user input screen receiving input from a user requesting the location of the at least one prescription order element, determining the location of the at least one prescription order element and displaying the location of the at least one prescription order element.

28. The graphical user interface of claim 5, further comprising a user input screen receiving input from a user requesting the location of the at least one prescription order element, determining the location of the at least one prescription order element, tracking the at least one prescription order element through the prescription order fulfillment system and displaying the location of the at least one prescription order element.

29. The graphical user interface of claim 28, wherein the user input screen receives the input comprising at least one of invoice number, prescription number, member number, and work order identifier from the user requesting the location of the at least one prescription order element, and determining the location of the at least one prescription order element responsive to the input received from the user.

30. The graphical user interface of claim 28, wherein the user input screen receives the input from the user, and determines at least one of: a queue in which the at least one prescription order element is currently located, a plurality of queues where the at least one prescription order element was processed, an amount of time the at least one prescription order element spent in each of the plurality of queues, and a total elapsed time that the at least one prescription order element has been in the prescription order fulfillment system.

* * * * *